(12) United States Patent
Andersen et al.

(10) Patent No.: US 9,375,496 B2
(45) Date of Patent: Jun. 28, 2016

(54) HALOGENATED COMPOUNDS FOR CANCER IMAGING AND TREATMENT AND METHODS FOR THEIR USE

(71) Applicants: The University of British Columbia, Vancouver (CA); British Columbia Cancer Agency Branch, Vancouver (CA)

(72) Inventors: Raymond John Andersen, Vancouver (CA); Carmen Adriana Banuelos, Richmond (CA); Javier Garcia Fernandez, Colunga (ES); Yusuke Imamura, Chiba (JP); Jian Kunzhong, Vancouver (CA); Nasrin R. Mawji, Burnaby (CA); Marianne Dorothy Sadar, West Vancouver (CA); Jun Wang, Surrey (CA); Amy (Hsing Chen) Tien, Vancouver (CA)

(73) Assignees: British Columbia Cancer Agency Branch (CA); The University of British Columbia (CA)

( * ) Notice: Subject to any disclaimer, the term of this patent is extended or adjusted under 35 U.S.C. 154(b) by 0 days.

(21) Appl. No.: 14/481,727

(22) Filed: Sep. 9, 2014

(65) Prior Publication Data
US 2015/0125389 A1    May 7, 2015

Related U.S. Application Data

(60) Provisional application No. 61/875,556, filed on Sep. 9, 2013.

(51) Int. Cl.
| | |
|---|---|
| *A61K 31/09* | (2006.01) |
| *A61K 31/225* | (2006.01) |
| *A61K 51/04* | (2006.01) |
| *C07C 69/63* | (2006.01) |
| *C07C 43/23* | (2006.01) |
| *A61K 45/06* | (2006.01) |
| *C07B 59/00* | (2006.01) |
| *C07C 57/58* | (2006.01) |
| *A61K 31/167* | (2006.01) |
| *A61K 31/275* | (2006.01) |
| *A61K 31/4166* | (2006.01) |

(52) U.S. Cl.
CPC .............. *A61K 51/04* (2013.01); *A61K 31/09* (2013.01); *A61K 31/167* (2013.01); *A61K 31/225* (2013.01); *A61K 31/275* (2013.01); *A61K 31/4166* (2013.01); *A61K 45/06* (2013.01); *C07B 59/001* (2013.01); *C07C 43/23* (2013.01); *C07C 57/58* (2013.01); *C07C 69/63* (2013.01); *C07B 2200/05* (2013.01)

(58) Field of Classification Search
CPC ..... A61K 31/09; A61K 31/336; A61K 45/06; C07C 43/23; C07C 43/215; C07C 2101/14; C07C 229/08

See application file for complete search history.

(56) References Cited

U.S. PATENT DOCUMENTS

| | | | |
|---|---|---|---|
| 2,571,217 A | 10/1951 | Davis et al. |
| 2,890,189 A | 6/1959 | Greenlee |
| 4,284,574 A | 8/1981 | Bagga |
| 4,369,298 A | 1/1983 | Kida et al. |
| 4,855,184 A | 8/1989 | Klun et al. |
| 4,904,760 A | 2/1990 | Gaku et al. |
| 5,043,375 A | 8/1991 | Henning et al. |

(Continued)

FOREIGN PATENT DOCUMENTS

| | | |
|---|---|---|
| CA | 2 339 775 A1 | 3/2000 |
| CA | 2 606 262 A1 | 11/2006 |

(Continued)

OTHER PUBLICATIONS

Anne Riu et al. Characterization of Novel Ligands of ERalpha, Erbeta, and PPARgama: The case of Halogenated Bisphenol A and Their Conjugated Metabolites, Toxicological Sciences, 122(2), 372-382, 2011.*

(Continued)

*Primary Examiner* — Michael G Hartley
*Assistant Examiner* — Jagadishwar Samala
(74) *Attorney, Agent, or Firm* — Cooley LLP

(57) ABSTRACT

Compounds having a structure of Formula I:

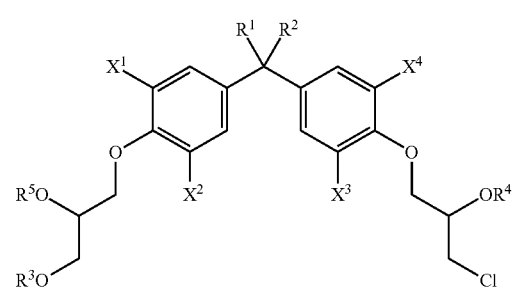

or a pharmaceutically acceptable salt, tautomer or stereoisomer thereof, wherein $R^1$, $R^2$, $R^3$, $R^4$, $R^5$, $X^1$, $X^2$, $X^3$ and $X^4$ are as defined herein, and wherein the compound comprises at least one F, Cl, Br, I or $^{123}$I moiety, are provided. Uses of such compounds for imaging diagnostics in cancer and therapeutics methods for treatment of subjects in need thereof, including prostate cancer as well as methods and intermediates for preparing such compounds are also provided.

23 Claims, 36 Drawing Sheets

(56) References Cited

U.S. PATENT DOCUMENTS

| | | | |
|---|---|---|---|
| 5,155,196 | A | 10/1992 | Kolb et al. |
| 5,362,615 | A | 11/1994 | Hagemann et al. |
| 5,403,697 | A | 4/1995 | Doessel et al. |
| 5,753,730 | A | 5/1998 | Nagata et al. |
| 5,998,674 | A | 12/1999 | Taketani et al. |
| 6,218,430 | B1 | 4/2001 | Allegretto et al. |
| 6,245,117 | B1 | 6/2001 | Nishikawa et al. |
| 7,183,323 | B2 | 2/2007 | Chinn et al. |
| 7,674,795 | B2 | 3/2010 | Mailliet et al. |
| 8,686,050 | B2 | 4/2014 | Sadar et al. |
| 9,173,939 | B2 | 11/2015 | Andersen et al. |
| 2003/0092724 | A1 | 5/2003 | Kao et al. |
| 2003/0105268 | A1 | 6/2003 | Boriack et al. |
| 2004/0049004 | A1 | 3/2004 | Boriack et al. |
| 2004/0243316 | A1 | 12/2004 | Weinmann et al. |
| 2008/0153837 | A1 | 6/2008 | Mailliet et al. |
| 2008/0193380 | A1 | 8/2008 | Dalton et al. |
| 2008/0255395 | A1 | 10/2008 | Dai et al. |
| 2009/0105349 | A1 | 4/2009 | Barvian et al. |
| 2011/0230556 | A1* | 9/2011 | Sadar et al. ............ 514/548 |
| 2013/0045204 | A1 | 2/2013 | Sadar et al. |
| 2013/0109758 | A1 | 5/2013 | Sadar et al. |
| 2013/0131167 | A1 | 5/2013 | Sadar et al. |
| 2013/0245129 | A1 | 9/2013 | Sadar et al. |
| 2013/0336962 | A1 | 12/2013 | Andersen et al. |
| 2014/0248263 | A1 | 9/2014 | Andersen et al. |
| 2014/0335080 | A1 | 11/2014 | Andersen et al. |
| 2015/0010469 | A1 | 1/2015 | Andersen et al. |

FOREIGN PATENT DOCUMENTS

| | | |
|---|---|---|
| EP | 0056175 A1 | 7/1982 |
| EP | 0 293 768 A1 | 12/1988 |
| EP | 0515128 A1 | 11/1992 |
| FR | 1389005 | 2/1965 |
| JP | B-S45-008432 | 3/1970 |
| JP | 63-196675 | 8/1988 |
| JP | H01-503541 | 11/1989 |
| JP | H02-4815 | 1/1990 |
| JP | 6-049473 A2 | 4/1994 |
| JP | 9-176240 A | 7/1997 |
| JP | A-H10-316803 | 12/1998 |
| JP | 11-166087 A2 | 6/1999 |
| JP | 2000-072705 A2 | 3/2000 |
| JP | 2005-325301 A | 11/2005 |
| JP | 2006-208607 A | 8/2006 |
| JP | 2006-265351 A2 | 10/2006 |
| JP | 2007-290980 | 11/2007 |
| PL | 135932 | 9/1984 |
| PL | 141793 B1 | 8/1987 |
| WO | WO 88/09782 | 12/1988 |
| WO | WO 98/34930 A1 | 8/1998 |
| WO | WO 00/01813 A2 | 1/2000 |
| WO | WO 00/10958 A1 | 3/2000 |
| WO | WO 01/88013 A2 | 11/2001 |
| WO | WO 02/05813 A2 | 1/2002 |
| WO | WO 03/004481 A1 | 1/2003 |
| WO | WO 2005/042464 A1 | 5/2005 |
| WO | WO 2005/077967 A1 | 8/2005 |
| WO | WO 2008/101806 A2 | 8/2008 |
| WO | WO 2010/000066 A1 | 1/2010 |
| WO | WO 2011/082487 A1 | 7/2011 |
| WO | WO 2011/082488 A1 | 7/2011 |
| WO | WO 2012/139039 A2 | 10/2012 |
| WO | WO 2012/145328 A1 | 10/2012 |
| WO | WO 2012/145330 A1 | 10/2012 |
| WO | WO 2013/028572 A1 | 2/2013 |
| WO | WO 2013/028791 A1 | 2/2013 |
| WO | WO 2014/179867 A1 | 11/2014 |

OTHER PUBLICATIONS

Anderson, R. et al., "Regression of Castrate-Recurrent Prostate Cancer by a Small-Molecule Inhibitor of the Amino-Terminus Domain of the Androgen Receptor", *Cancer Cell*, 17:535-546 (2010).

Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), Ref. No. 13510 and 39700 (EFSA-Q-2003-178), *The EFSA Journal*, 86:1-40 (2004).

Auzou et al., *European Journal of Medicinal Chemistry*, 9(5):548-554 (1974) (and English Abstract).

Balbay, M.D. et al., "Highly Metastatic Human Prostate Cancer Growing within the Prostate of Athymic Mice Overexpresses Vascular Endothelial Growth Factor", *Clinical Cancer Research*, 5:783-789 (1999).

Bao, B. et al., "Androgen signaling is required for the vitamin D-mediated growth inhibition in human prostate cancer cells", *Oncogene*, 23:3350-3360 (2004).

Berge, S.M. et al., "Pharmaceutical Salts", *Pharmaceutical Sciences*, 66(1):1-19 (1977).

Berger, U. et al., "Identification of Derivatives of Bisphenol a Diglycidyl Ether and Novolac Glycidyl Ether in Can Coatings by Liquid Chromatography/Ion Trap Mass Spectrometry," Journal of AOAC International, *Food Chemical Contaminants*, 83(6):1367-1376 (2000).

Biles, J.E. et al., "Determination of the Diglycidyl Ether of Bisphenol A and its Derivatives in Canned Foods", *J. Agric. Food Chem.*, 47:1965-1969 (1999).

Bisson, W.H. et al., "Discovery of antiandrogen activity of nonsteroidal scaffolds of marketed drugs", *PNAS*, 104(29):11927-11932 (2007).

Blaszczyk, N. et al., "Osteoblast-Derived factors Induce Androgen-Independent Proliferation and Expression of Prostate-Specific Antigen in Human Prostate Cancer Cells", *Clin. Cancer Res.*, 10:1860-1869 (2004).

Bohler, Paul et al., "Identification of Migrants from Coatings of Food Cans and Tubes: Reaction Products of Bisphenol-A-Diglycidyl Ether (BADGE) with Phenols and Solvents", *Mitt. Gebiete Lebensm. Hyg.*, 89:529-547 (1998).

Brzozowski, Z. et al., "Precursors for bisphenolic resins", CAPLUS Database Accession No. 1990:36690, Document No. 112:33690, (1987), 1 page (Abstract).

Bruckheimer, E.M. et al., "Apoptosis in prostate carcinogenesis A growth regulator and a therapeutic target", *Cell Tissue Res*, 301:153-162 (2000).

Chang, C. et al., "Development of Peptide Antagonists for the Androgen Receptor Using Combinatorial Peptide Phage Display", *Molecular Endocrinology*, 19(10):2478-2490 (2005).

Choi, K. M. et al., "New Families of Photocurable Oligomeric Fluoromonomers for Use in Dental Composites", *Chemistry of Materials*, 8(12):2704-2707 (1996).

Clinton, G.M. et al., "Estrogen action in human ovarian cancer", *Critical Reviews in Oncology/Hematology*, 25:1-9 (1997).

Crivello, J. V. et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.

Crivello, J. V. et al., "Synthesis and photopolymerization of multifunctional propenyl ether monomers", *Journal of Macromolecular Science, Pure and Applied Chemistry*, A31(9):1105-1119 (1994).

Cook, W. D., "Fracture and Structure of Highly Crosslinked Polymer Composites", *Journal of Applied Polymer Science*, 42:1259-1269 (1991).

Culig, Zoran et al., "Androgen Receptor Activation in Prostatic Tumor Cell Lines by Insulin-like Growth Factor-I, Keratinocyte Growth Factor, and Epidermal Growth Factor", *Cancer Research*, 54:5474-5478 (1994).

Danquah, M. et al., "Micellar Delivery of Bicalutamide and Embelin for Treating Prostate Cancer", *Pharmaceutical Research*, 26:2081-2092 (2009).

Das, Debasish et al., "Sulfonic acid functionalized mesoporous MCM-41 silica as a convenient catalyst for Bisphenol-A synthesis", *Chemical Communications*, pp. 2178-2179 (2001).

(56) References Cited

OTHER PUBLICATIONS

Dehm, S. et al., "Ligand-independent Androgen Receptor Activity is Activation Function-2-independent and Resistant to Antiandrogens in Androgen Refractory Prostate Cancer Cells", *The Journal of Biological Chemistry*, 281(38):27882-27893 (2006).

Dehm, S. et al., "Splicing of a Novel Androgen Receptor Exon Generates a Constitutively Active Androgen Receptor that Mediates Prostate Cancer Therapy Resistance", *Cancer Research*, 68:5469-5477 (2008).

Edmondson, J. M. et al., "The human ovarian surface epithelium is an androgen responsive tissue", *British Journal of Cancer*, 86:879-885 (2002).

Estebanez-Perpi,ñá, E. et al., "A surface on the androgen receptor that allosterically regulates coactivator binding," *PNAS*, 104 (41):16074-16079 (2007).

Estebanez-Perpiñá, E. et al., "The Molecular Mechanisms of Coactivator Utilization in Ligand-dependent Transactivation by the Androgen Receptor," *The Journal of Biological Chemistry*, 280(9):8060-8068 (2005).

Fehlberg S. et al., "Bisphenol A diglycidyl ether induces apoptosis in tumor cells independently of peroxisome proliferator-activated receptor-y, in caspase-dependent and -independent manners," *Biochem. J.*, 362:573-578 (2002).

Gallart-Ayala, H. et al., "The analysis of bisphenol A-diglycidyl ether (BADGE), bisphenol F-diglycidyl ether (BFDGE) and their derivatives in canned food and beverages by LC-MS/MS", *Thermo Fisher Scientific Inc.*, 4 pages (2011).

Garuti, L., et al., "Irreversible Protein Kinase Inhibitors", *Current Medicinal Chemistry*, 18:2981-2994 (2011).

Gleave, Martin et al., "Acceleration of Human Prostate Cancer Growth in Vivo by Factors Produced by Prostate and Bone Fibroblasts", *Cancer Research*, 51:3753-3761 (1991).

Gregory, Christopher et al., "Epidermal Growth Factor Increases Coactivation of the Androgen Receptor in Recurrent Prostate Cancer", *The Journal of Biological Chemistry*, 279(8):7119-7130 (2004).

Guinan, P.D. et al., "Impotence Therapy and Cancer of the Prostate", *The American Journal of Surgery*, 131:599-600 (1976).

Guo, Zhiyong et al., "A Novel Androgen Receptor Splice Variant Is Up-regulated during Prostate Cancer Progression and Promotes Androgen Depletion—Resistant Growth", *Cancer Research*, 69:2305-13 (2009).

Haggstrom, Stina et al., "Testosterone Induces Vascular Endothelial Growth Factor Synthesis in the Ventral Prostate in Castrated Rats", *The Journal of Urology*, 161:1620-1625 (1999).

Harper et al., "Expression of Androgen Receptor and Growth Factors in Premalignant Lesions of the Prostate", *Journal of Pathology*, 186:169-177 (1998).

He, B. et al., "Activation Function 2 in the Human Androgen Receptor Ligand Binding Domain Mediates Interdomain Communication with the $NH_2$-terminal Domain", *The Journal of Biological Chemistry*, 274(52):37219-37225 (1999).

He, B. et al., "Structural Basis for Androgen Receptor Interdomain and Coactivator Interactions Suggests a Transition in Nuclear Receptor Activation Function Dominance", *Molecular Cell*, 16:425-438 (2004).

Heinlein, Cynthia A., et al., "Androgen Receptor in Prostate Cancer", *Endocrine Reviews*, 25(2):276-308 (2004).

Helzlsouer, Kathy J., et al., "Serum Gonadotropins and Steroid Hormones and the Development of Ovarian Cancer", *JAMA*, 274(24):1926-1930 (1995).

Horoszewicz, J.S. et al., "LNCaP Model of Human Prostatic Carcinoma", *Cancer Research*, 43:1809-1818 (1983).

Hu, R. et al., "Ligand-Independent Androgen Receptor Variants Derived from Splicing of Cryptic Exons Signify Hormone-Refractory Prostate Cancer", *Cancer Research*, 69:16-22 (2009).

Huber, P.R. et al., "Prostate Specific Antigen. Experimental and Clinical Observations", *Scand. J. Urol Nephrol.*, 104:33-39 (1987).

Hur, E. et al., "Recognition and Accommodation at the Androgen Receptor Coactivator Binding Interface", *PLoS Biology*, 2(9)(e274):1303-1312 (2004).

Isaacs, J.T., et al., "New Biochemical Methods to Determine Androgen Sensitivity of Prostatic Cancer: The Relative Enzymatic Index (REI)", *Prostate Cancer and Hormone Receptors*, pp. 133-144 (1979).

Isaacs, J.T., "Antagonistic Effect of Androgen on Prostatic Cell Death", *The Prostate*, 5:545-557 (1984).

Jackson, J. A. et al., "Prostatic Complications of Testosterone Replacement Therapy", *Arch Intern Med.*, 149:2365-2366 (1989).

Jenster, G. et al., "Domains of the Human Androgen Receptor Involved in Steroid Binding, Transcriptional Activation, and Subcellular Localization", *Molecular Endocrinology*, 5:1396-404 (1991).

Jia, L. et al., "Androgen Receptor Signaling: Mechanism of Interleukin-6 Inhibition", *Cancer Research*, 64:2619-2626 (2004).

Jia, L. et al., "Androgen Receptor-Dependent PSA Expression in Androgen-Independent Prostate Cancer Cells Does Not Involve Androgen Receptor Occupancy of the PSA Locus", *Cancer Research*, 65:8003-8008 (2005).

Kaighn, M.E. et al., "Prostate Carcinoma: Tissue Culture Cell Lines", *National Cancer Institute Monograph No. 49*, pp. 17-21 (1978).

Kemppainen, J. A. et al., "Distinguishing Androgen Receptor Agonists and Antagonists: Distinct Mechanisms of Activation by Medroxyprogesterone Acetate and Dihydrotestosterone", *Mol. Endocrinol.*, 13:440-454 (1999).

Kim, D. et al., "Androgen Receptor Expression and Cellular Proliferation During Transition from Androgen-Dependent to Recurrent Growth after Castration in the CWR22 Prostate Cancer Xenograft", *American Journal of Pathology*, 160(1):219-226 (2002).

Kolbel, M. et al., "Design of Liquid Crystalline Block Molecules with Nonconventional Mesophase Morphologies: Calamitic Bolaamphiphiles with Lateral Alkyl Chains", *J. Am. Chem. Soc.*,123:6809-6818 (2001).

Kumar, S. et al., "Synthesis of new crown analogs derived from bisphenol," *Indian Journal Chemistry*, 36B:656-661 (1997).

L'Heureux, A. et al., "Aminodifluorosulfinium Salts: Selective Fluorination Reagents with Enhanced Thermal Stability and Ease of Handling", *J. Org. Chem*, 75:3401-3411 (2010).

Langley, E. et al., "Evidence for an Anti-parallel Orientation of the Ligand-activated Human Androgen Receptor Dimer", *The Journal of Biological Chemistry*, 270(50):29983-29990 (1995).

Lannoye, G.S. et al., "N-Fluoroalkylated and N-alkylated analogs of the dopaminergic D-2 receptor antagonist raclopride", *J. Med. Chem.*, 33(9):2430-2437 (1990).

Loren, J.C. et al., "Synthesis of achiral and racemic catenanes based on terpyridine and a directionalized terpyridine mimic, pyridyl-phenanthroline", *Org. Biomol. Chem.*, 3(17):3105-3116 (2005).

Louie, M.C. et al., "Androgen-induced recruitment of RNA polymerase II to a nuclear receptor—p160 coactivator complex", *PNAS*, 100(5)2226-2230 (2003).

Martin, S.J. et al., "A new precursor for the radiosynthesis of [$^{18}$F]FLT", *Nuclear Medicine and Biology*, 29:263-273 (2002).

Masiello, D. et al., "Bicalutamide Functions as an Androgen Receptor Antagonist by Assembly of a Transcriptionally Inactive Receptor", *The Journal of Biological Chemistry*, 277(29):26321-26326 (2002).

Melnyk, O. et al., "Neutralizing Ant-Vascular Endothelial Growth Factor Antibody Inhibits Further Growth of Established Prostate Cancer and Metastases in a Pre-Clinical Model", *The Journal of Urology*, 161:960-963 (1999).

Miller, J.I. et al., "The Clinical Usefulness of Serum Prostate Specific Antigen After Hormonal Therapy of Metastatic Prostate Cancer", *The Journal of Urology*, 147:956-961 (1992).

Mitsiades, C.S. et al., "Molecular biology and cellular physiology of refractoriness to androgen ablation therapy in advanced prostate cancer", *Expert Opin. Investig. Drugs*,10(6):1099-1115 (2001).

Myung, J-K et al., "An androgen receptor N-terminal domain antagonist for treating prostate cancer", *The Journal of Clinical Investigation*, 123(7):2948-2960 (2013).

Nakazawa, H. et al., "In vitro assay of hydrolysis and chlorohydroxy derivatives of bisphenol A diglycidyl ether for estrogenic activity", *Food and Chemical Toxicology*, 40:1827-1832 (2002).

(56) References Cited

OTHER PUBLICATIONS

Nazareth, L.V. et al, "Activation of the Human Androgen Receptor through a Protein Kinase A Signaling Pathway", *The Journal of Biological Chemistry*, 271(33):19900-19907 (1996).
Nedolya, N. A. et al., Zhurnal Organicheskoi Khimii, 30(8):1163-1166 (1994).
Noble, R. L., "The development of prostatic adenocarcinoma in Nb Rats following prolonged sex hormone administration", *Cancer Research*, 37:1929-1933 (1977).
Noble, R. L., "Sex steroids as a cause of adenocarcinoma of the dorsal prostate in Nb Rats, and their influence on the growth of transplants", *Oncology*, 34:138-141 (1977).
Ogawa, Y. et al., "Estrogenic activities of chemicals related to food contact plastics and rubbers tested by the yeast two-hybrid assay," *Food Additives and Contaminants*, 23:4, 422-430 (2006).
Paris, F. et al., "Phenylphenols, biphenols, bisphenol-A and 4-tert-octyphenol exhibit α and β estrogen activities and antiandrogen activity in reporter cell lines," *Molecular and Cellular Endocrinology*, 193:43-49 (2002).
Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," Polimery, (Warsaw), 40(5):274-2777 (1995).
Poustka, J. et al., "Determination and occurrence of bisphenol A, bisphenol a diglycidyl ether, and bisphenol F diglycidyl ether, including their derivatives, in canned foodstuffs' from the Czech retail market," *Czech J. Food Sci.*, 25(4):221-229 (2006).
Quayle, S. et al., "Androgen receptor decoy molecules block the growth of prostate cancer", *PNAS*, 104(4):1331-1336 (2007).
Rao, B.R. et al., "Endocrine Factors in Common Epithelial Ovarian Cancer", *Endocrine Reviews*, 12(1):14-26 (1991).
Reader, C. E. L., "Epoxy Resin Derivatives for Stoving Systems", Surface Coatings Australia, 25(10):6-9 (1988).
Reid, J. et al., "Conformational Analysis of the Androgen Receptor Amino-terminal Domain Involved in Transactivation," *The Journal of Biological Chemistry*, 277:20079-20086 (2002).
Risch, H.A., "Hormonal Etiology of Epithelial Ovarian Cancer, With a Hypothesis Concerning the Role of Androgens and Progesterone", *Journal of the National Cancer Institute*, 90(23):1774-1786 (1998).
Roberts, J. T. et al., "Adenocarcinoma of Prostate in 40-Year-Old Body-Builder", *Lancet*, 2:742 (1986).
Rokicki, G. et al., "Reactions of 4-chloromethyl-1,3-dioxolan-2-one with phenols as a new route to polyols and cyclic carbonates", *Journal f. prakt. Chemie.*, 327:718-722 (1985).
Ross, R.K. et al., "Androgen Metabolism and Prostate Cancer: Establishing a Model of Genetic Susceptibility", *European Urology*, 35:355-361 (1999).
Rusu, E. et al.: "Photosensitive compounds with chloromethyl groups", *Revue Roumaine de Chimie*, 45(5):451-456 (2000).
Sadar, M., "Androgen-independent Induction of Prostate-specific Antigen Gene Expression via Cross-talk between the Androgen Receptor and Protein Kinase A signal Transduction Pathways," *The Journal of Biological Chemistry*, 274(12):7777-7783 (1999).
Sadar, M. et al., "Prostate cancer: molecular biology of early progression to androgen independence", *Endocrine-Related Cancer*, 6:487-502 (1999).
Sadar, M.D. et al., "Characterization of a New in Vivo Hollow Fiber Model for the Study of Progression of Prostate Cancer to Androgen Independence", *Molecular Cancer Therapeutics*, 1:629-637 (2002).
Sato, N. et al., "Intermittent Androgen Suppression Delays Progression to Androgen-independent Regulation of Prostate-specific Antigen Gene in the LNCaP Prostate Tumour Model", *J. Steroid Biochem. Mol. Biol.*, 58:139-146 (1996).
Sato, N. et al., "A Metastatic and Androgen-sensitive Human Prostate Cancer Model Using Intraprostatic Inoculation of LNCaP Cells in SCID Mice", *Cancer Research*, 57:1584-1589 (1997).
Satoh, K. et al., "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen", *Food and Chemical Toxicology*, 42:983-993 (2004).
Schaefer, A. et al, "Migration from can coatings: Part 3. Synthesis, identification and quantification of migrating epoxy-based substances below 1000 Da", *Food Additives and Contaminants*, 21(4):390-405 (2004).
Silverman, R. B., The Organic Chemistry of Drug Design and Drug Action, Academic Press, Inc., Harcourt Brace Jovanovich, pp. 15-20, 9 pages (1992).
Snoek, R. et al., "Induction of Cell-free, In Vitro Transcription by Recombinant Androgen Receptor Peptides", *J. Steroid Biochem. Mol. Biol.*, 59:243-250 (1996).
Still, W. C. et al., "Rapid Chromatographic Technique for Preparative Separations with Moderate Resolution", *J. Org. Chem.*, 43(14):2923-2925 (1978).
Sun, S. et al., "Castration resistance in human prostate cancer is conferred by a frequently occurring androgen receptor splice variant", *The Journal of Clinical Investigation*, 120(8):2715-30 (2010).
Tanji, N. et al., "Growth Factors: Rules in Andrology", *Archives of Andrology*, 47:1-7 (2001).
Taplin, M.E. et al., "Selection for Androgen Receptor Mutations in Prostate cancers Treated with Androgen Antagonist", *Cancer Research*, 59:2511-2515 (1999).
Taskeen, A. et al., "Analysis of bisphenol A in canned food: A mini review", *Asian Journal of Chemistry*, 22(5):4133-4135 (2010).
Thomson, A.A., "Role of androgens and fibroblast growth factors in prostatic development", *Reproduction*, 121:187-195 (2001).
Ueda, T. et al., "Activation of the Androgen Receptor N-terminal Domain by Interleukin-6 via MAPK and STAT3 Signal Transduction Pathways", *The Journal of Biological Chemistry*, 277(9):7076-7085 (2002).
Ueda, T. et al., "Ligand-independent Activation of the Androgen Receptor by Interleukin-6 and the Role of Steroid Receptor Coactivator-1 in Prostate cancer Cells", *The Journal of Biological Chemistry*, 277(41):38087-38094 (2002).
Uematsu, Y. et al., "Chlorohydrins of bisphenol a diglycidyl ether (BADGE) and bisphenol F diglycidyl ether (BFDGE) in canned foods and ready-to-drink coffees from the Japanese market", *Food Additives and Contaminants*, 18(2):177-185 (2001).
Van Der Kwast, T.H. et al., "Androgen Receptors in Endocrine-Therapy-Resistant Human Prostate Cancer", *Inter. J. Cancer*, 48:189-193 (1991).
Van Scherpenzeel, M. et al., "Nanomolar affinity, iminosugar-based chemical probes for specific labeling of lysosomal glucocerebrosidase", *Bioorganic & Medicinal Chemistry*, 18:267-273 (2010).
Wang, G. et al., "Identification of genes targeted by the androgen and PKA signaling pathways in prostate cancer cells", *Oncogene*, 25:7311-7323 (2006).
Wang, Q. et al., "Spatial and Temporal Recruitment of Androgen Receptor and Its Coactivators Involves Chromosomal Looping and Polymerase Tracking", *Molecular Cell*, 19:631-642 (2005).
Wetherill, Y. B. et al., "In vitro molecular mechanisms of bisphenol A action," *Reproductive Toxicology*, 24:178-198 (2007).
Wilding, G., "The Importance of Steroid Hormones in Prostate Cancer", *Cancer Surveys*, 14:113-130 (1992).
Wilson, J.D. et al., "Long-Term Consequences of Castration in Men: Lessons from the Skoptzy and the Eunuchs of the Chinese and Ottoman Courts", *The Journal of Clinical Endocrinology & Metabolism*, 84:4324-4331 (1999).
Wong, C. et al., "Steroid Requirement for Androgen Receptor Dimerization and DNA Binding", *J. Biol. Chem.*, 268(25):19004-19012 (1993).
Xu, X. et al, "Synthesis and Stability Study of Dental Monomers Containing Methacrylamidoethyl Phosphonic Acids", *Journal of Polymer Science: Part A Polymer Chemistry*, 45:99-110 (2007).
Ye, Deyong, "An Introduction to Computer-Aided Drug Design", 3 pages, Jan. 31, 2004 decision.

(56) References Cited

OTHER PUBLICATIONS

Zuhayra, M. et al., "New approach for the synthesis of [$^{18}$F]fluoroethyltyrosine for cancer imaging: Simple, fast, and high yielding automated synthesis", *Bioorganic & Medicinal Chemistry*, 17:7441-7448 (2009).
Supplementary European Search Report in EP Application No. 09771876.1 dated Jun. 20, 2011, 5 pages.
Supplementary European Search Report in EP Application No. 11731645.5 dated mailed Jun. 2, 2013, 11 pages.
Decision of Refusal for Japanese Application No. 2011-515039, mailed Dec. 2, 2014, 18 pages (English translation).
International Preliminary Report on Patentability for PCT/CA2009/000902 issued Jan. 5, 2011, 7 pages.
International Search Report for PCT/CA2009/000902 mailed Sep. 1, 2009, 4 pages.
Written Opinion for PCT/CA2009/000902 mailed Sep. 1, 2009, 6 pages.
International Preliminary Report on Patentability for PCT/US2012/032584 issued Oct. 8, 2013, 6 pages.
International Search Report for PCT/US2012/032584 mailed Jul. 31, 2012, 3 pages.
Written Opinion for PCT/US2012/032584 mailed Jul. 31, 2012, 5 pages.
International Preliminary Report on Patentability for PCT/US2012/033959 dated Oct. 22, 2013, 8 pages.
International Search Report for PCT/US2012/033959 mailed Jul. 18, 2012, 3 pages.
Written Opinion for PCT/US2012/033959 mailed Jul. 18, 2012, 7 pages.
International Preliminary Report on Patentability for PCT/US2012/033957 dated Oct. 22, 2013, 6 pages.
International Search Report for PCT/US2012/033957 mailed Jul. 18, 2012, 3 pages.
Written Opinion for PCT/US2012/033957 mailed Jul. 18, 2012, 5 pages.
International Preliminary Report on Patentability for PCT/CA2011/000019 dated Jul. 10, 2012, 8 pages.
International Search Report for PCT/CA2011/000019 mailed Mar. 21, 2011, 7 pages.
Written Opinion for PCT/CA2011/000019 mailed Mar. 21, 2011, 7 pages.
International Preliminary Report on Patentability for PCT/CA2011/000021 dated Jul. 10, 2012, 8 pages.
International Search Report for PCT/CA2011/000021 mailed Apr. 11, 2011, 8 pages.
Written Opinion for PCT/CA2011/000021 mailed Apr. 11, 2011, 7 pages.
International Preliminary Report on Patentability for PCT/US2012/051481 dated Feb. 25, 2014, 8 pages.
International Search Report for PCT/US2012/051481 mailed Nov. 26, 2012, 4 pages.
Written Opinion for PCT/US2012/051481 mailed Nov. 26, 2012, 7 pages.
International Preliminary Report on Patentability for PCT/US2012/051923 dated Feb. 25, 2014, 9 pages.
International Search Report for PCT/US2012/051923 mailed Jan. 28, 2013, 4 pages.
Written Opinion for PCT/US2012/051923 mailed Jan. 28, 2013, 8 pages.
Extended European Search Report in Application No. EP 12768410.8 dated Sep. 22, 2014, 10 pages.
International Search Report and Written Opinion for PCT/CA2014/000414 mailed Dec. 4, 2014, 6 pages.
International Search Report and Written Opinion for PCT/CA2014/000685 mailed Dec. 4, 2014, 13 pages.
Petersen, H. et al., "Determination of bisphenol A diglycidyl ether (BADGE) and its derivatives in food: identification and quantification by internal Standard", *Eur. Food Res. Technol.*, 216:355-364 (2003).
Poouthree, K. et al., "Comparison of resolution in microemulsion EKC and MEKC employing suppressed electroosmosis: Application to bisphenol-A-diglycidyl ether and its derivatives", *Electrophoresis*, 28(20):3705-3711 (2007).
Patani and LaVoie, "Bioisosterism: A Rational Approach in Drug Design", Chem. Rev., 96: 3147-3176 (1996).
Strub and McKim, "Dimethyl Sulfoxide USP, PhEur in Approved Pharmaceutical Products and Medical Devices", PharmaTech.com, 6 pages (2008). http://www.pharmtech.com/print/224268 ?page=full &rel=canonical.
Alvarez, C. et al., "Confirmational and Experimental Studies on the Dipole Moments of Models of Comblike Polymers", Macromolecules, 30(20): 6369-6375 (1997).
Henke, H., "Selektive präparative gelchromatographische Trennung niedermolekularer Verbindungen an Sephadex LH-20", Journal of Chromatography, 254: 296-308 (1983).
Riu, A. et al., "Characterization of Novel Ligands of ERα, Erβ, and PPARγ: The Case of Halogenated Bisphenol A and Their Conjugated Metabolites", Toxicology Sciences, 122(2): 372-382 (2011).
Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).
International Preliminary Report on Patentability for PCT/CA2014/000414 mailed Nov. 10, 2015, 7 pages.

* cited by examiner

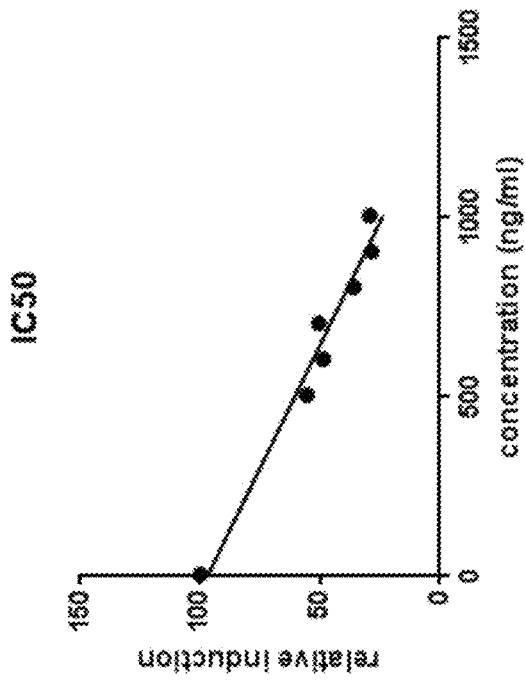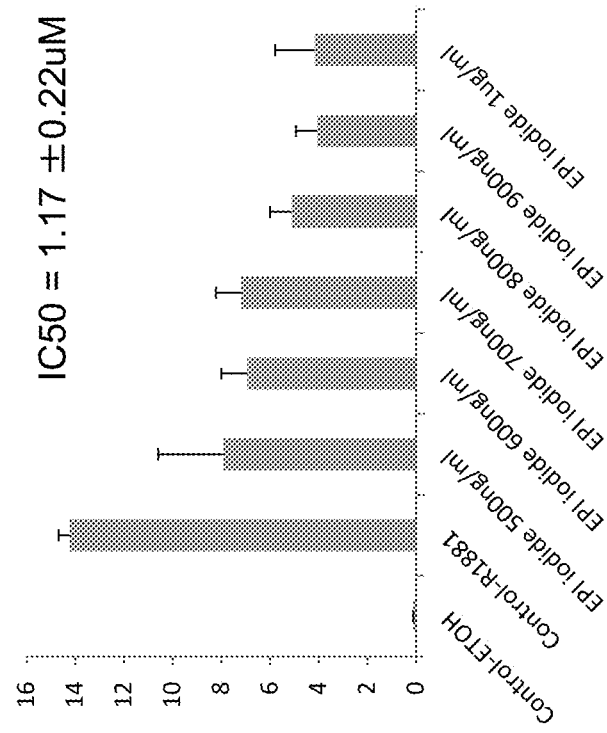
FIG. 1A
FIG. 1B

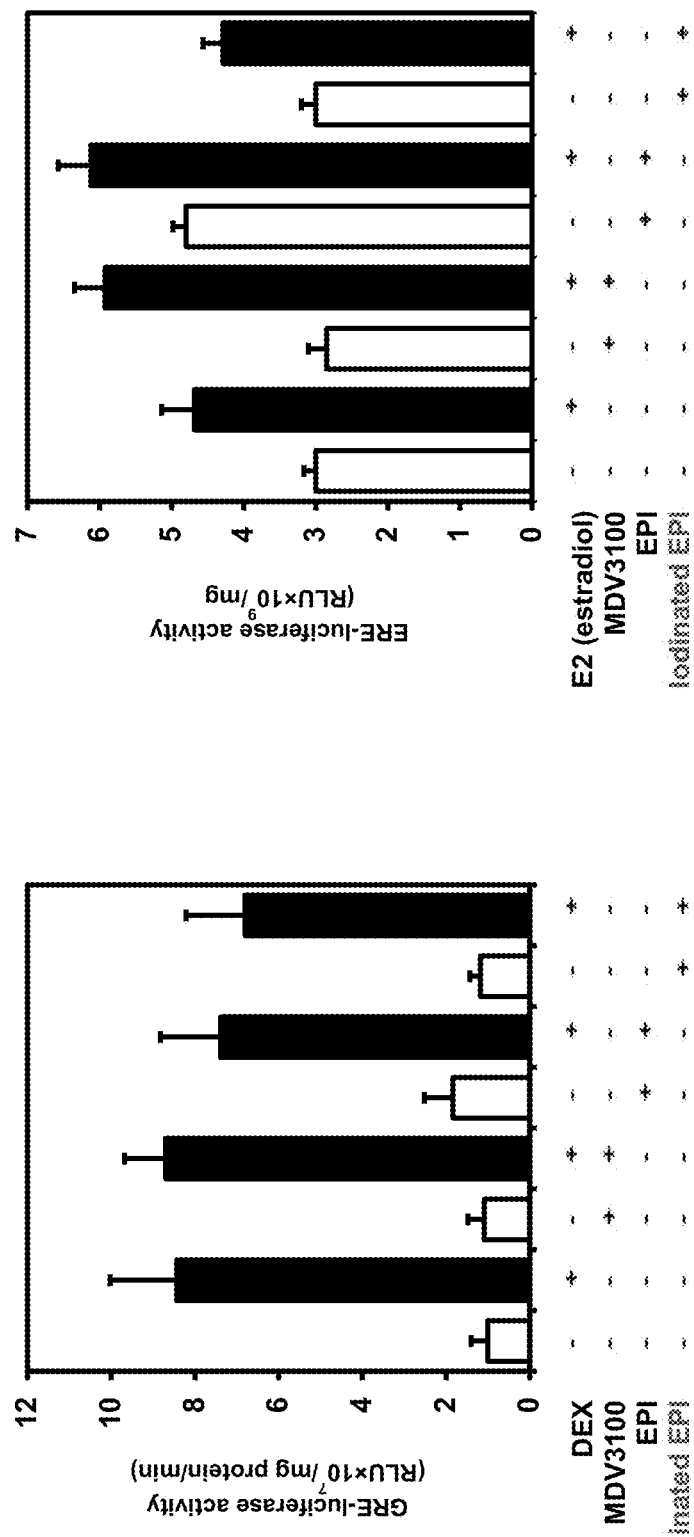

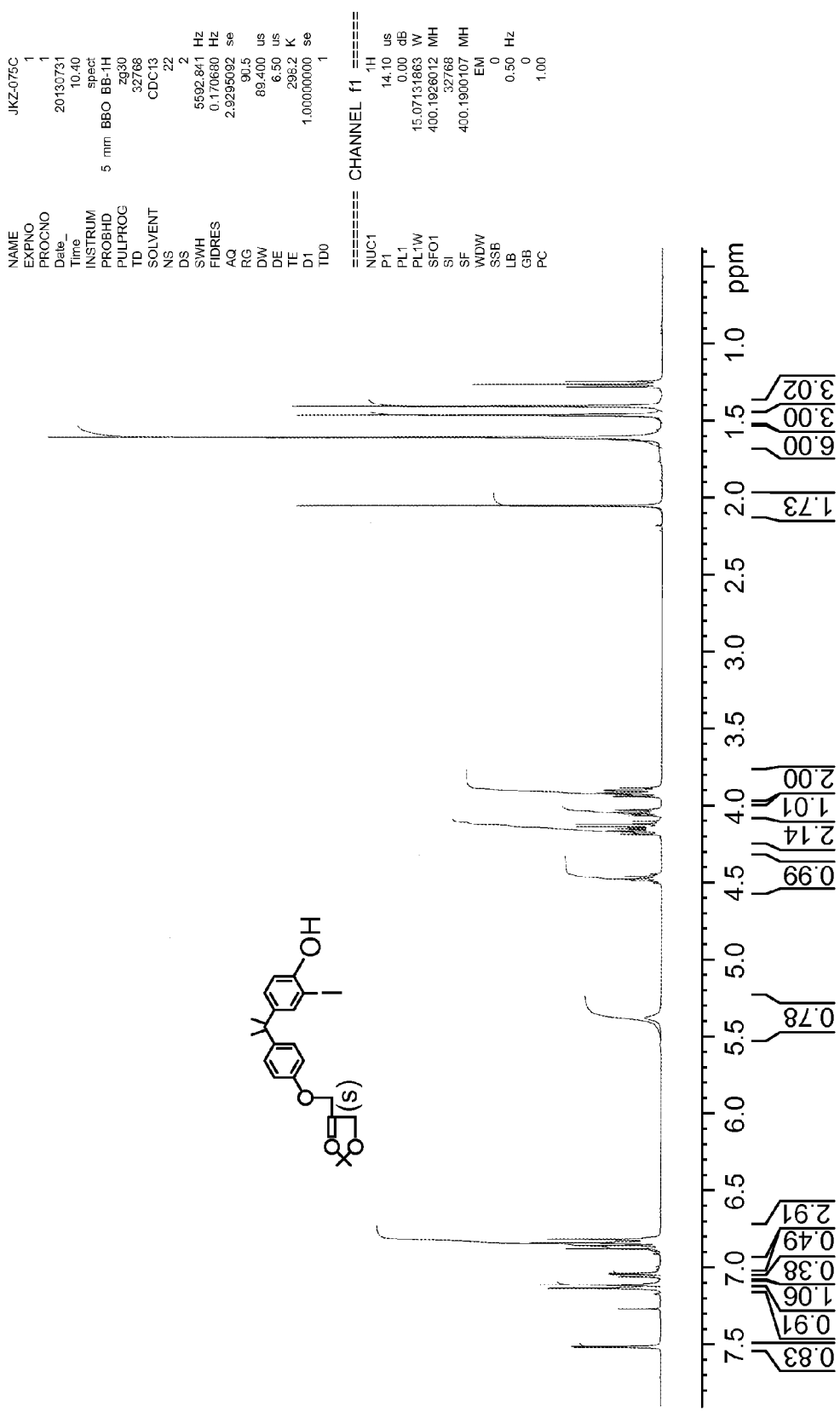
FIG. 3A  Compound iii-1, H NMR

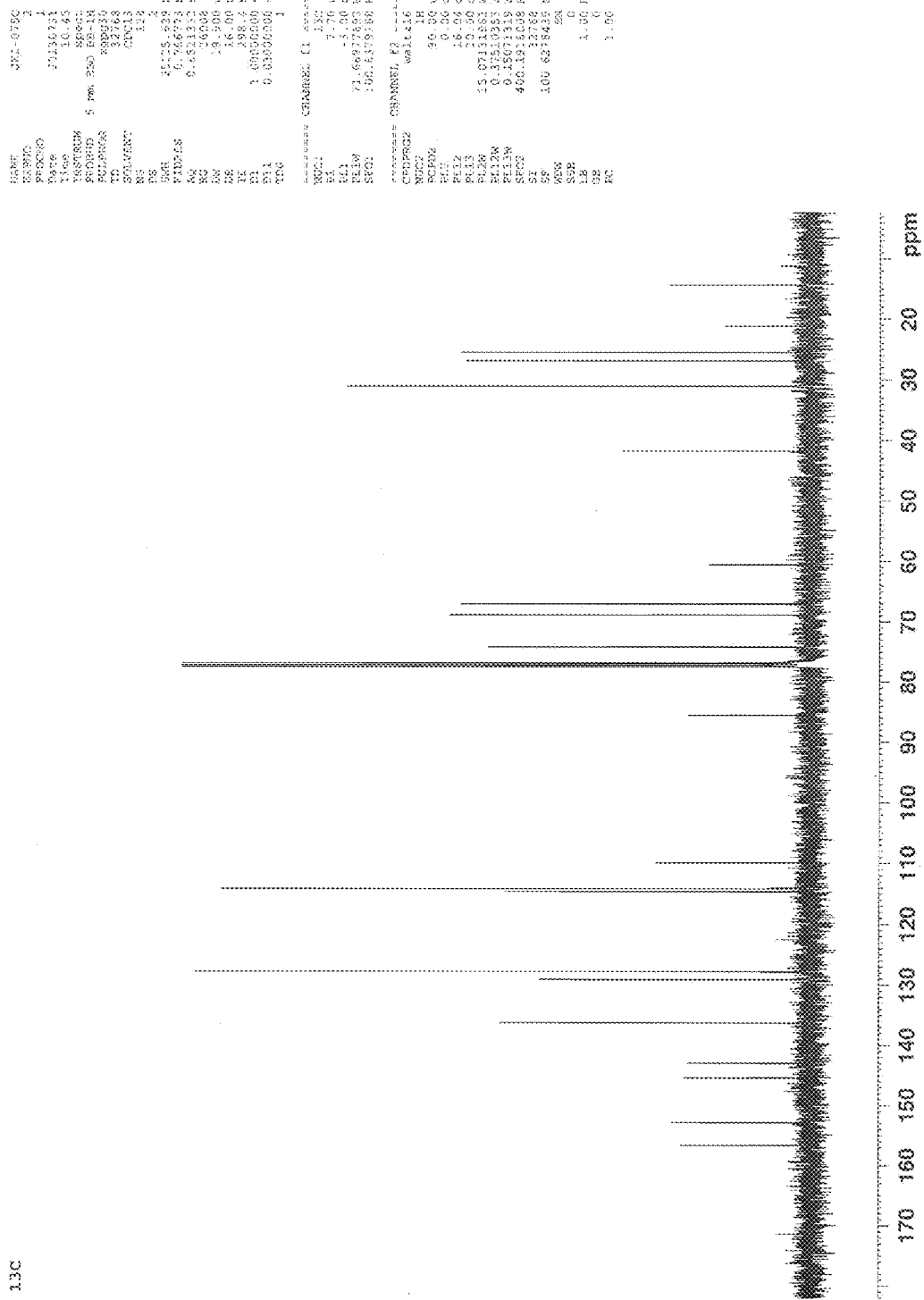
FIG. 3B Compound iii-1, C NMR

Mass Spec Report:
File:Andersen97-1   Sample: 1   Date:31-Jul-2013
Time:13:00:06   Group Name:Andersen   Method:C:\MassLynx\OALogin\OAMethods\MEOH_FIA_ES_1.olp
User Sample ID:JKZ-075C   OAMS#:Andersen97-1   Vial:1:24

Printed: Wed Jul 31 13:08:16 2013

Sample Report:

Sample 1 Instrument Method C:\MassLynx\OALogin\OAMethods\MEOH_FIA_ES_1.olp

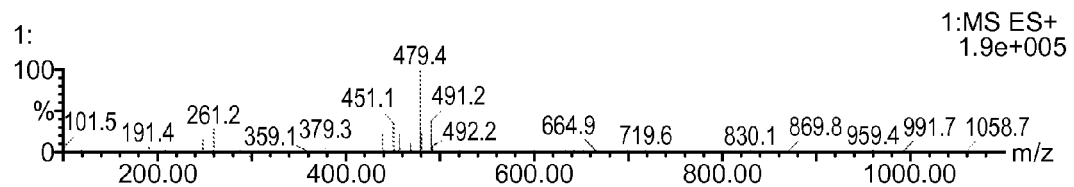

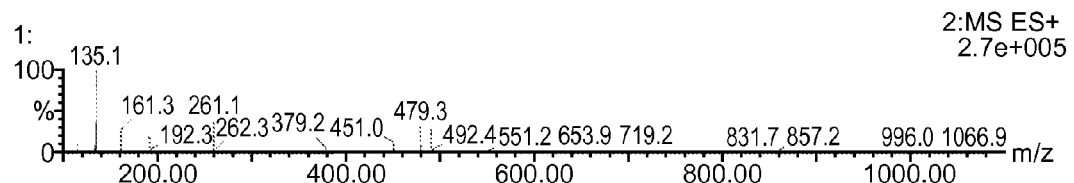

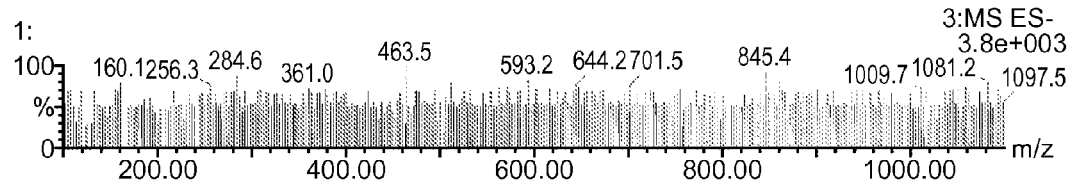

No element were found.

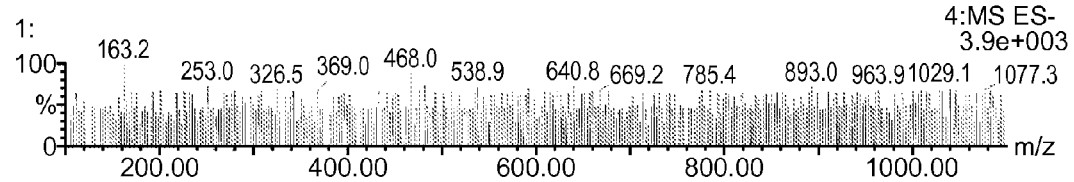

No elements were found.

Sample 2 Instrument Method C:\MassLynx\OALogin\OAMethods\MEOH_FIA_ES_1.olp

*FIG. 3C*     *Compound iii-I, MS*

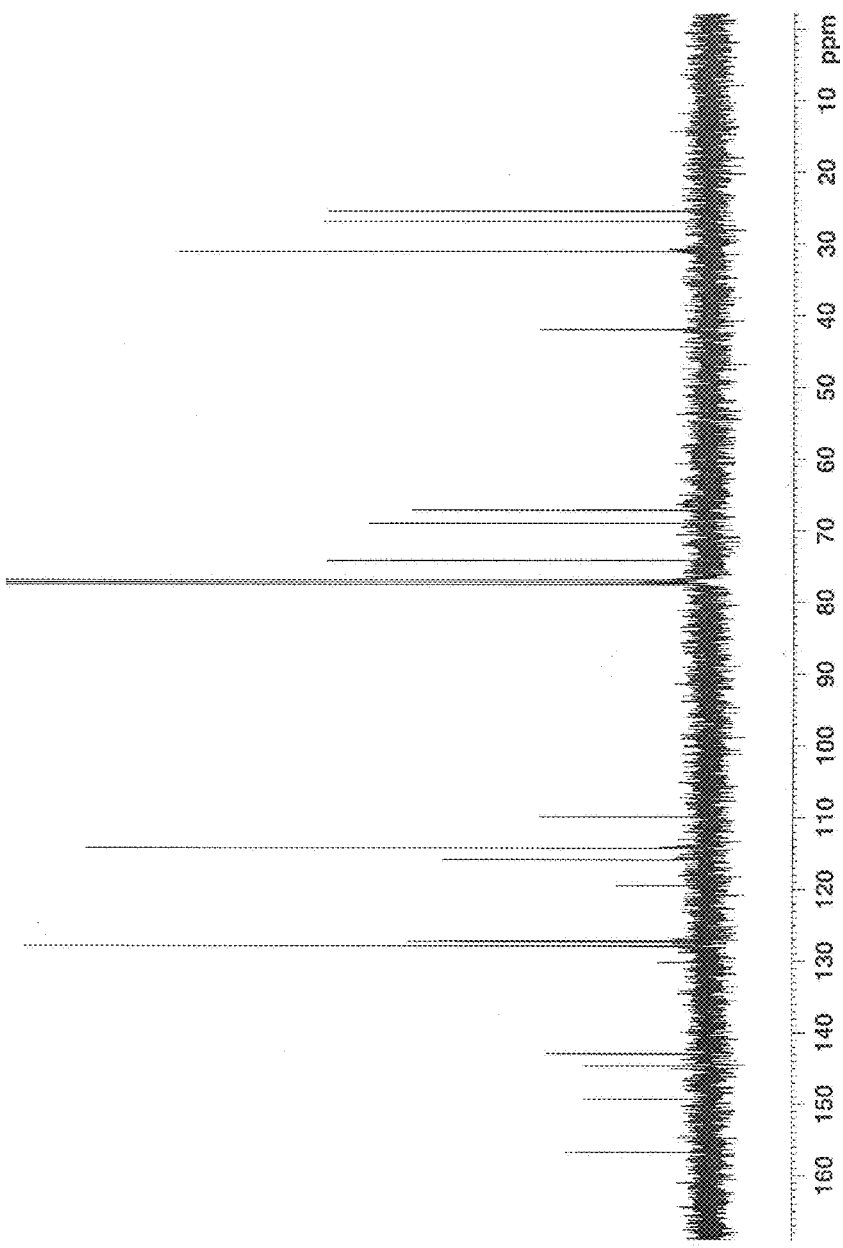
FIG. 4B  Compound iii-Br, C NMR

Mass Spec Report:
File:Andersen100-1  Sample: 1  Date:14-Aug-2013
Time:12:12:43  Group Name:Andersen  Method:C:\MassLynx\OALogin\OAMethods\MEOH_FIA_ES_1.olp
User Sample ID:JKZ-079  OAMS#:Andersen100-1  Vial:1:6

Printed: Wed Aug 14 12:26:38 2013

Sample Report:

Sample 1 Instrument Method C:\MassLynx\OALogin\OAMethods\MEOH_FIA_ES_1.olp

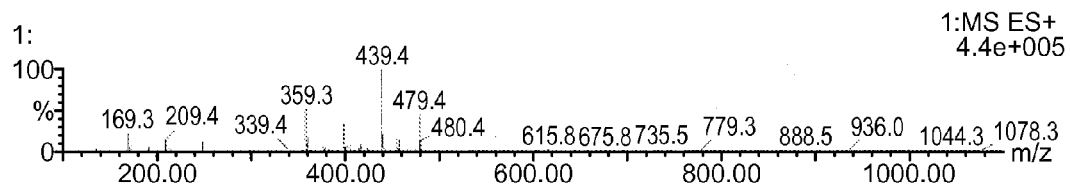

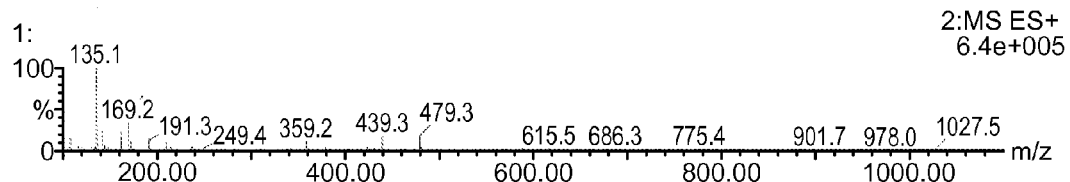

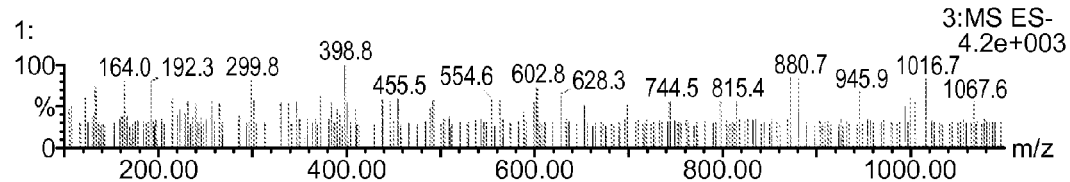

No elements were found.

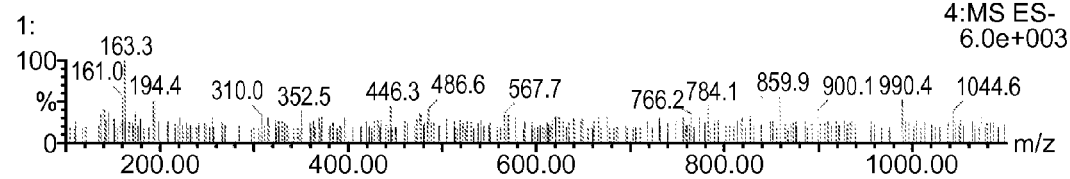

Sample 2 Instrument Method C:\MassLynx\OALogin\OAMethods\MEOH_FIA_ES_1.olp

*FIG.4C*  Compound iii-BR, MS

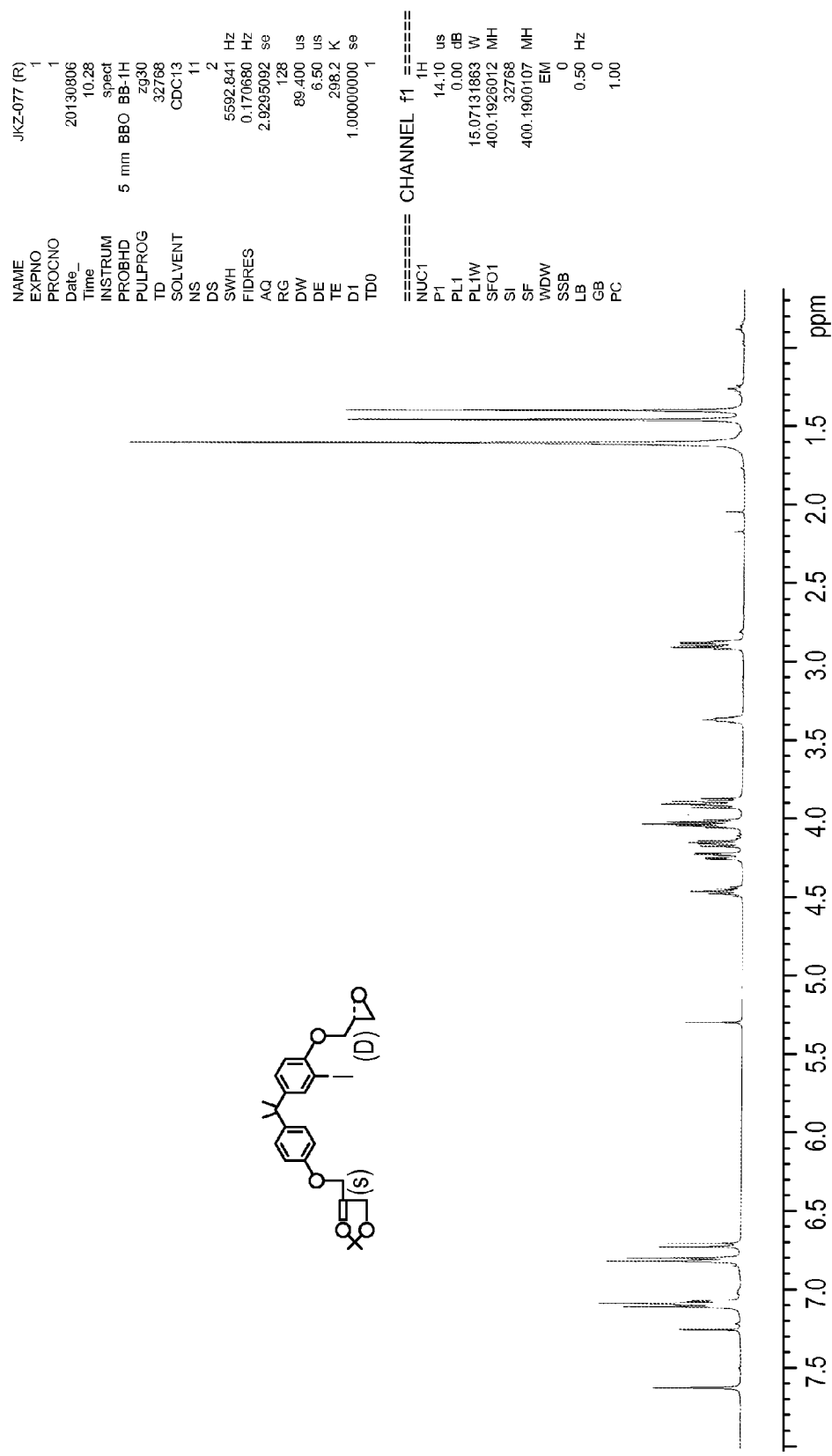
FIG.6A  Compound iv-I, H NMR

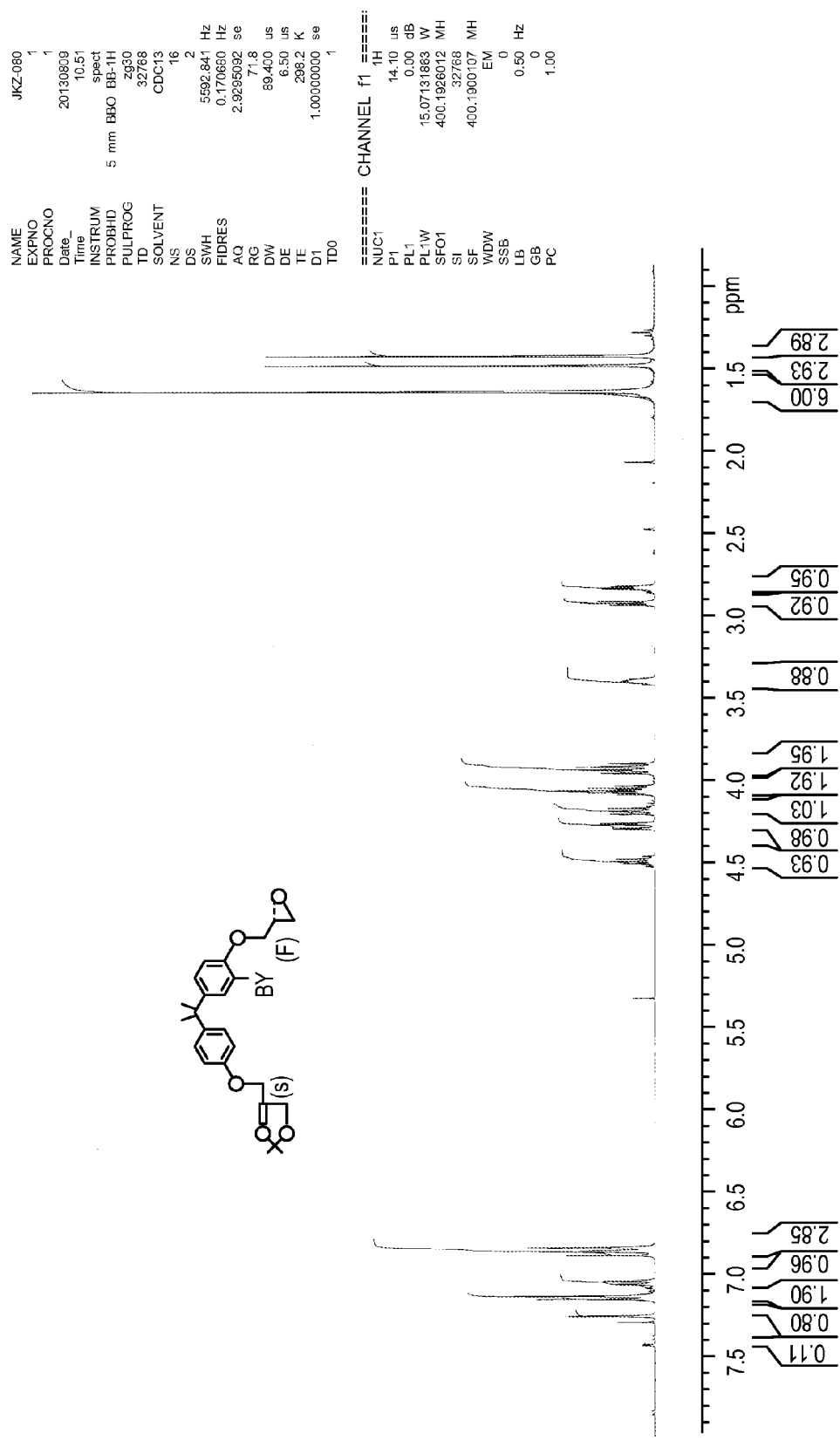
FIG. 7A Compound iv-Br, H NMR

Compound iv-Br, C NMR

*Compound iv-Br, MS*

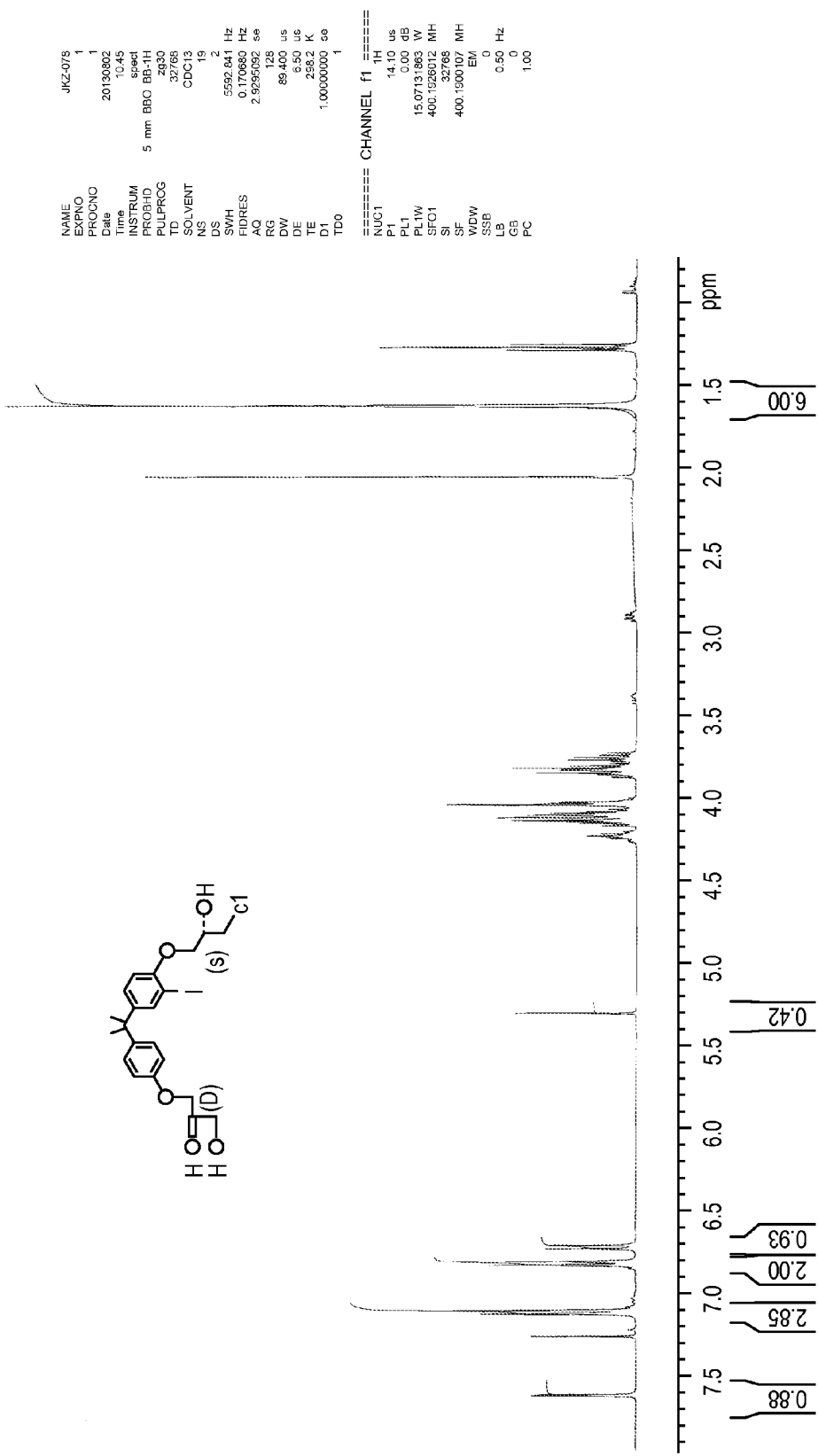
FIG. 8A Compound 8d, H NMR

Compound 8d, C NMR

Mass Spec Report:
File:Andersen98-1   Sample: 1   Date:02-Aug-2013
Time:12:59:23   Group Name:Andersen   Method:C:\MassLynx\OALogin\OAMethods\MEOH_FIA_ES_1.olp
User Sample ID:JKZ-078   OAMS#:Andersen98-1   Vial:1:28

Printed: Fri Aug 02 13:07:58 2013

Sample Report:

Sample 1 Instrument Method C:\MassLynx\OALogin\OAMethods\MEOH_FIA_ES_1.olp

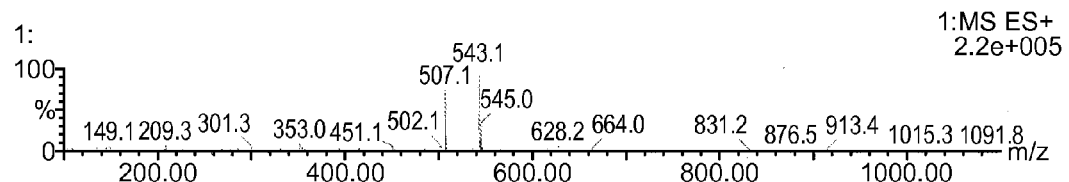

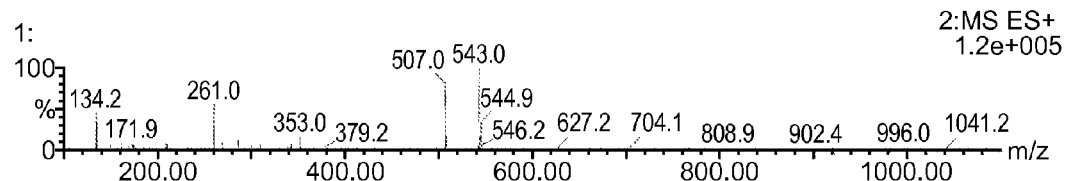

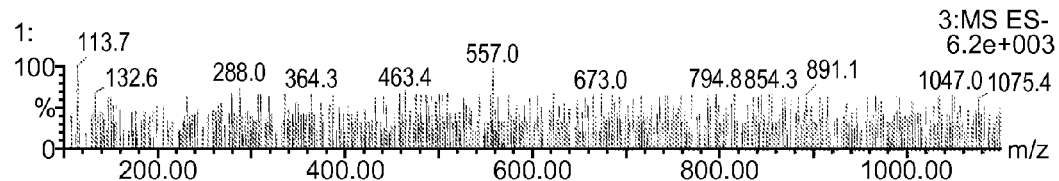

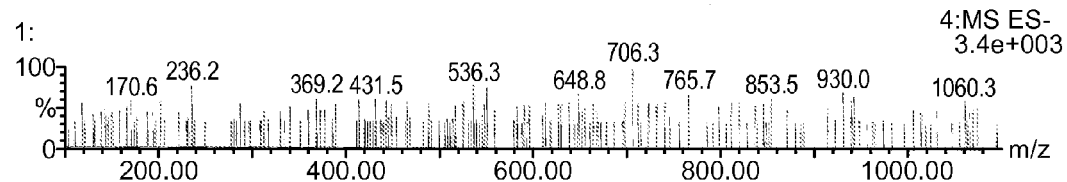

No elements were found.

Sample 2 Instrument Method C:\MassLynx\OALogin\OAMethods\MEOH_FIA_ES_1.olp

*FIG. 8C*                                                               *Compound 8d, MS*

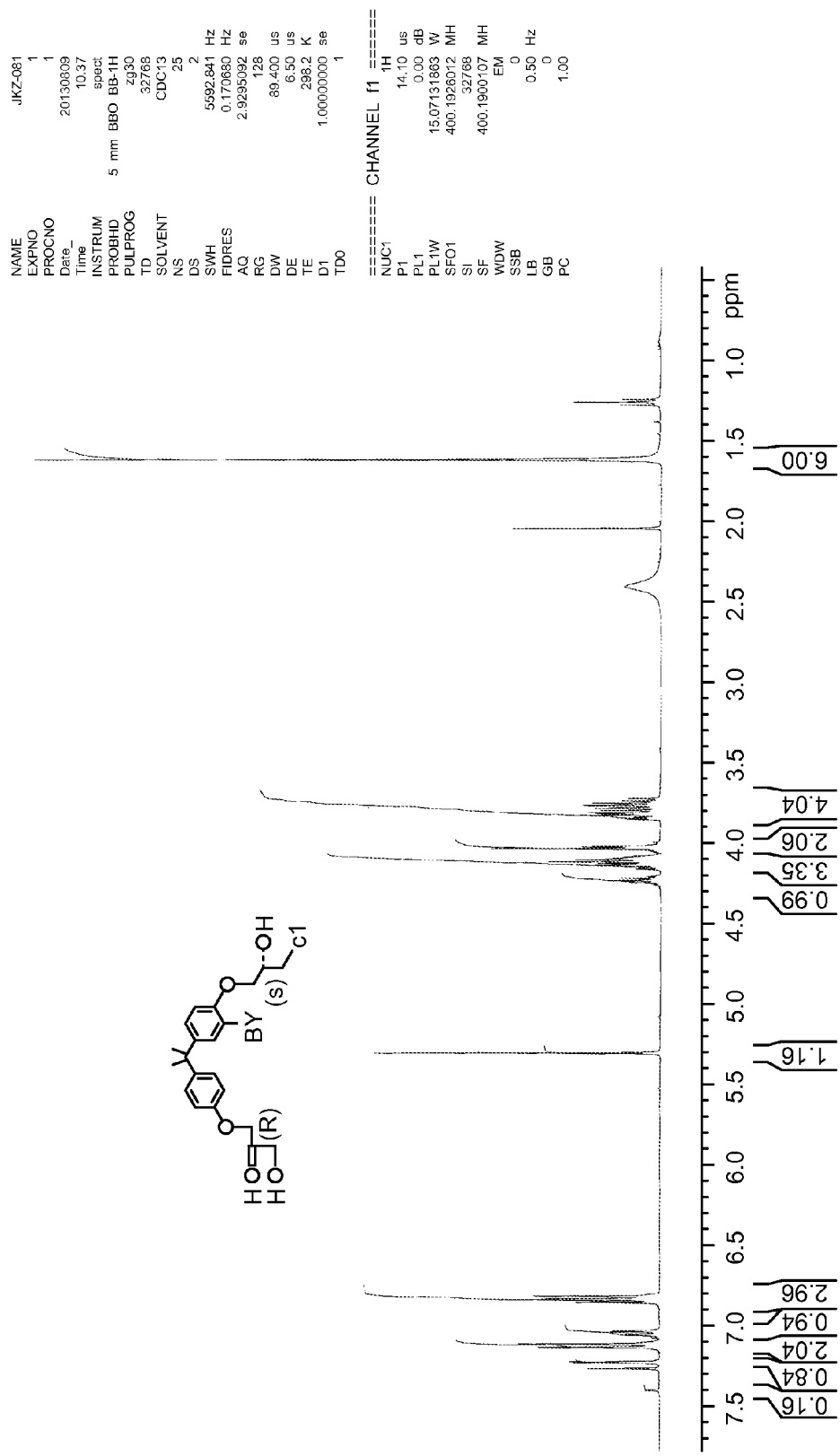
FIG. 9A Compound 9d, H NMR

Compound 9d, C NMR

Mass Spec Report:
File:Andersen100-3  Sample: 3  Date:14-Aug-2013
Time:12:20:49  Group Name:Andersen  Method:C:\MassLynx\OALogin\OAMethods\MEOH_FIA_ES_1.olp
User Sample ID:JKZ-081  OAMS#:Andersen100-3  Vial:1:8
Printed: Wed Aug 14 12:26:38 2013
Sample Report (continued):
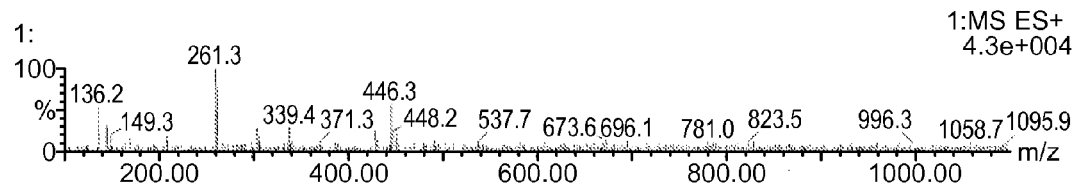
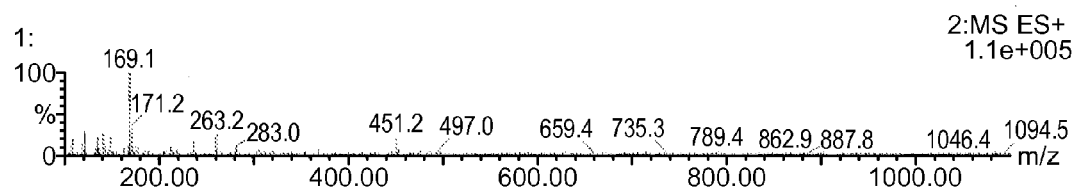
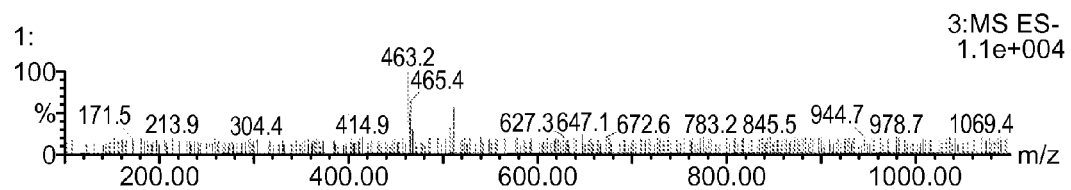
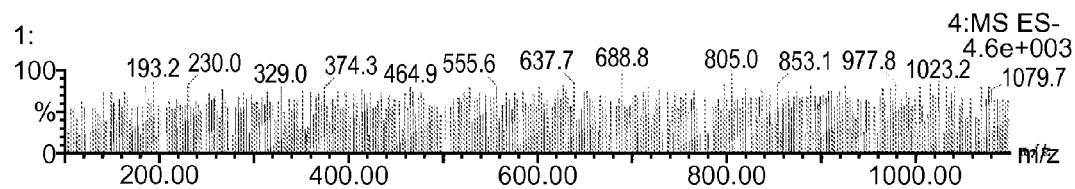
No elements were found.
*Compound 9d, MS*
*FIG. 9C*

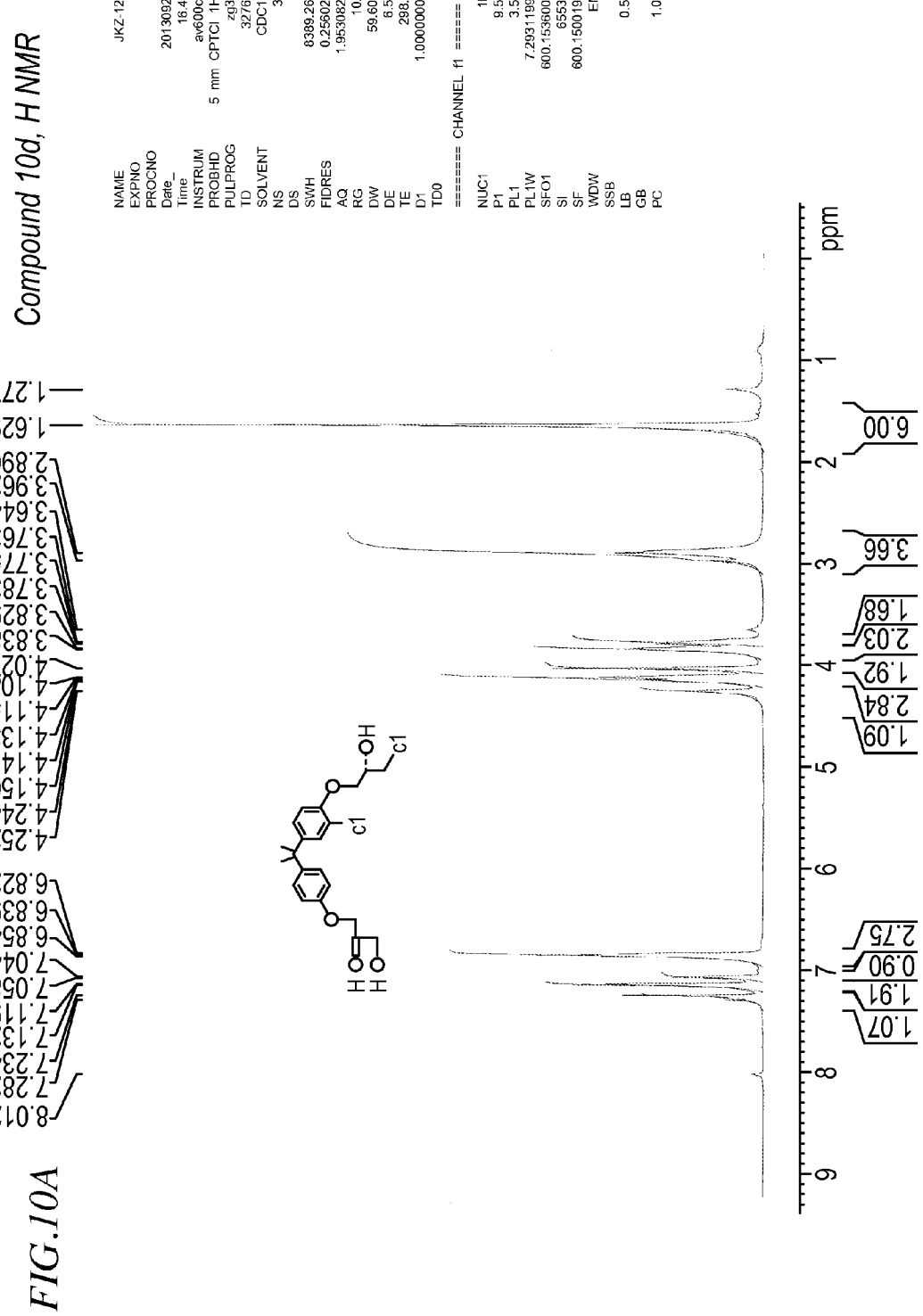
FIG. 10A Compound 10d, H NMR

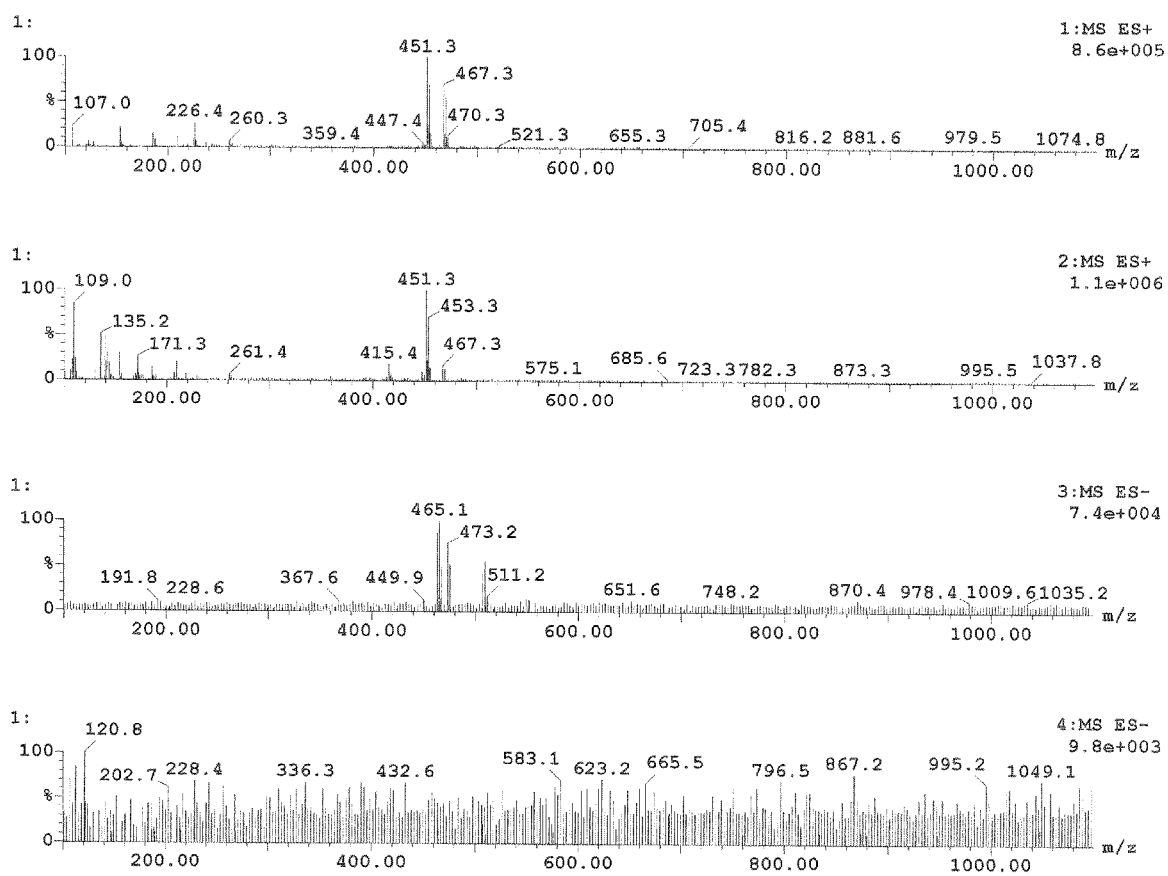
FIG. 10C  Compound 10d, MS

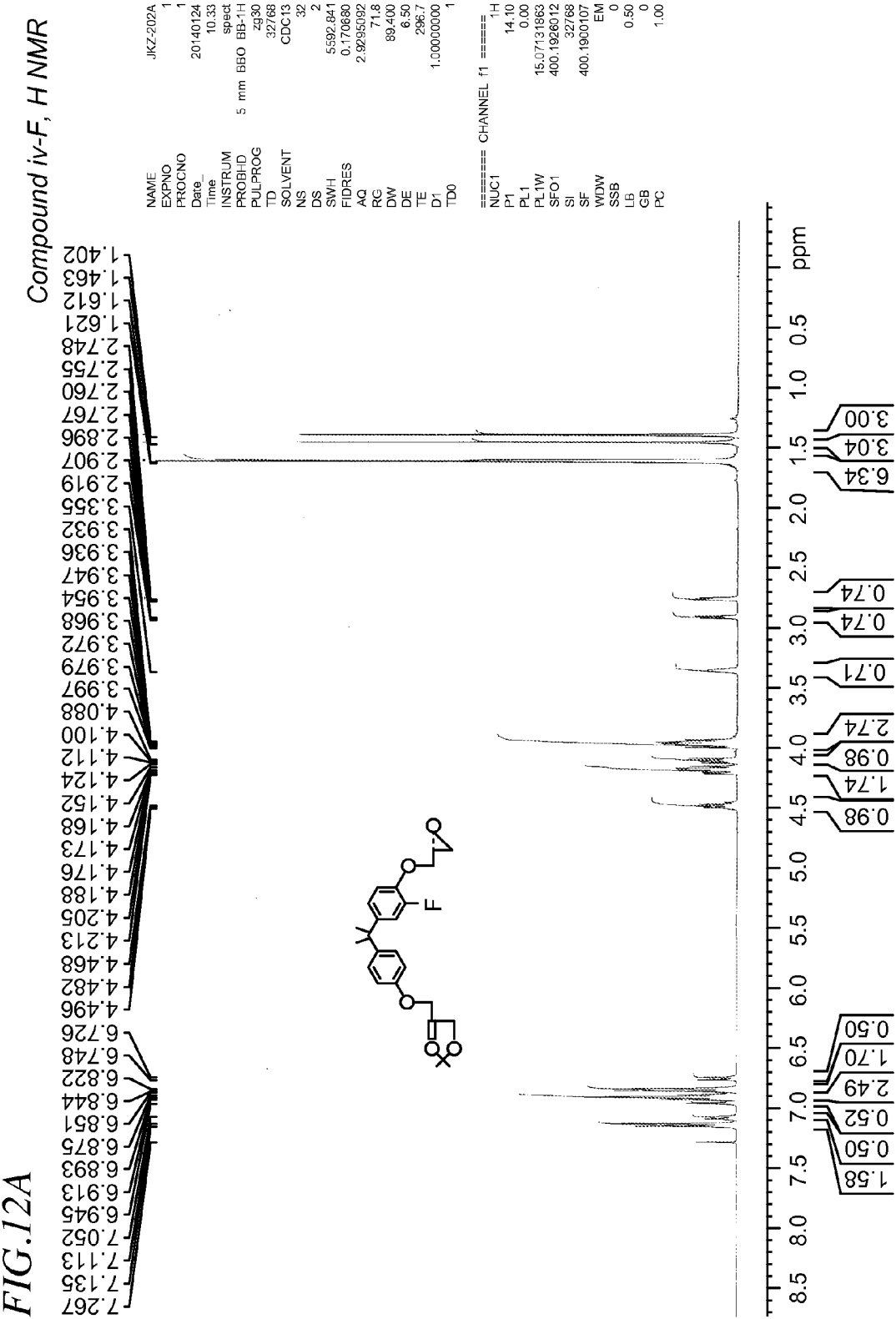
FIG. 12A Compound iv-F, H NMR

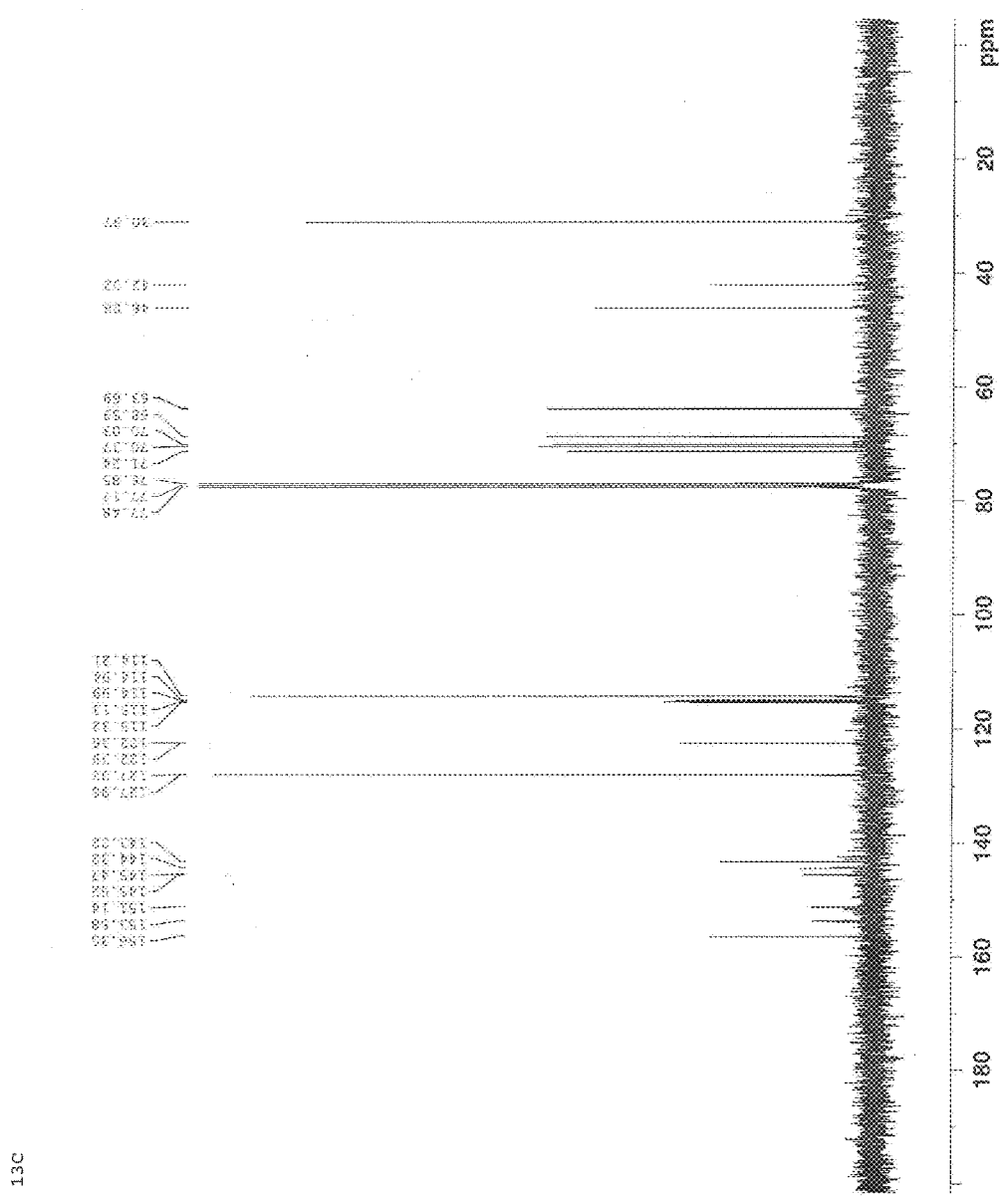
FIG. 13B Compound 11d, H NMR

Mass Spec Report:
File: Andersen179-1  Sample: 1  Date: 27-Jan-2014
Time: 11:30:11  Group Name: Andersen  Method: C:\MassLynx\OALogin\OAMethods\MEOH_FIA_ES_1.olp
User Sample ID: JKZ-203  OAMS#: Andersen179-1  Vial: 1:114
Printed: Mon Jan 27 11:34:34 2014
Sample Report:
Sample 1 Instrument Method C:\MassLynx\OALogin\OAMethods\MEOH_FIA_ES_1.olp
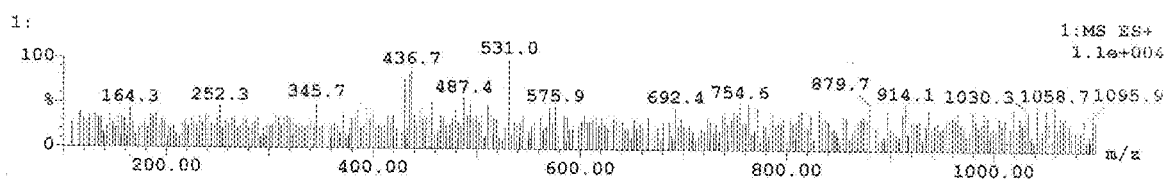
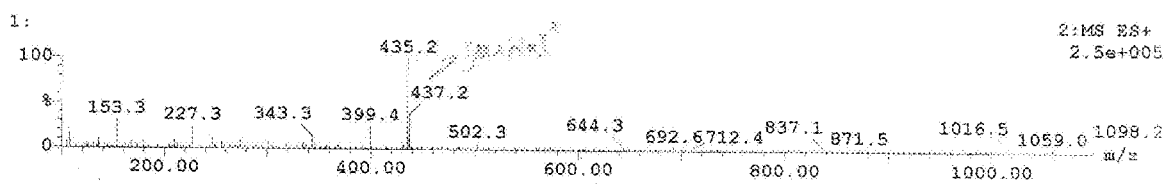
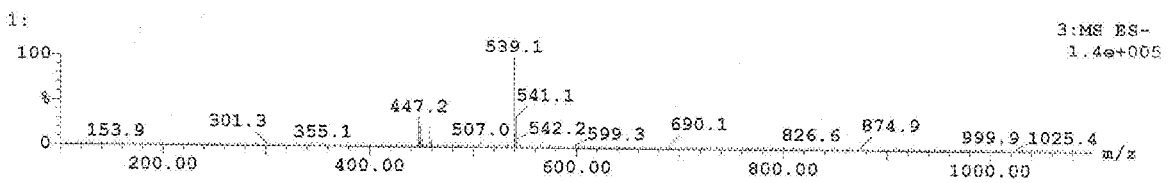
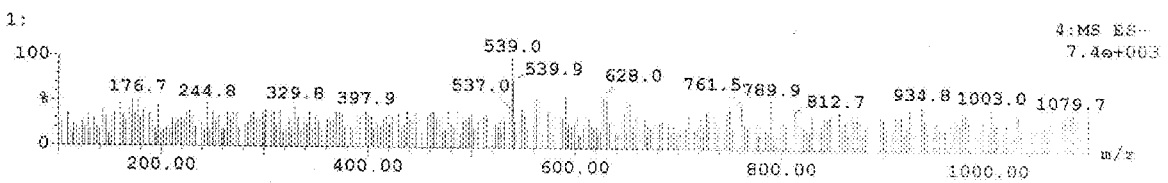
*FIG. 13C*　　　　　　　　　　　　　　　　　　　Compound 11d, MS

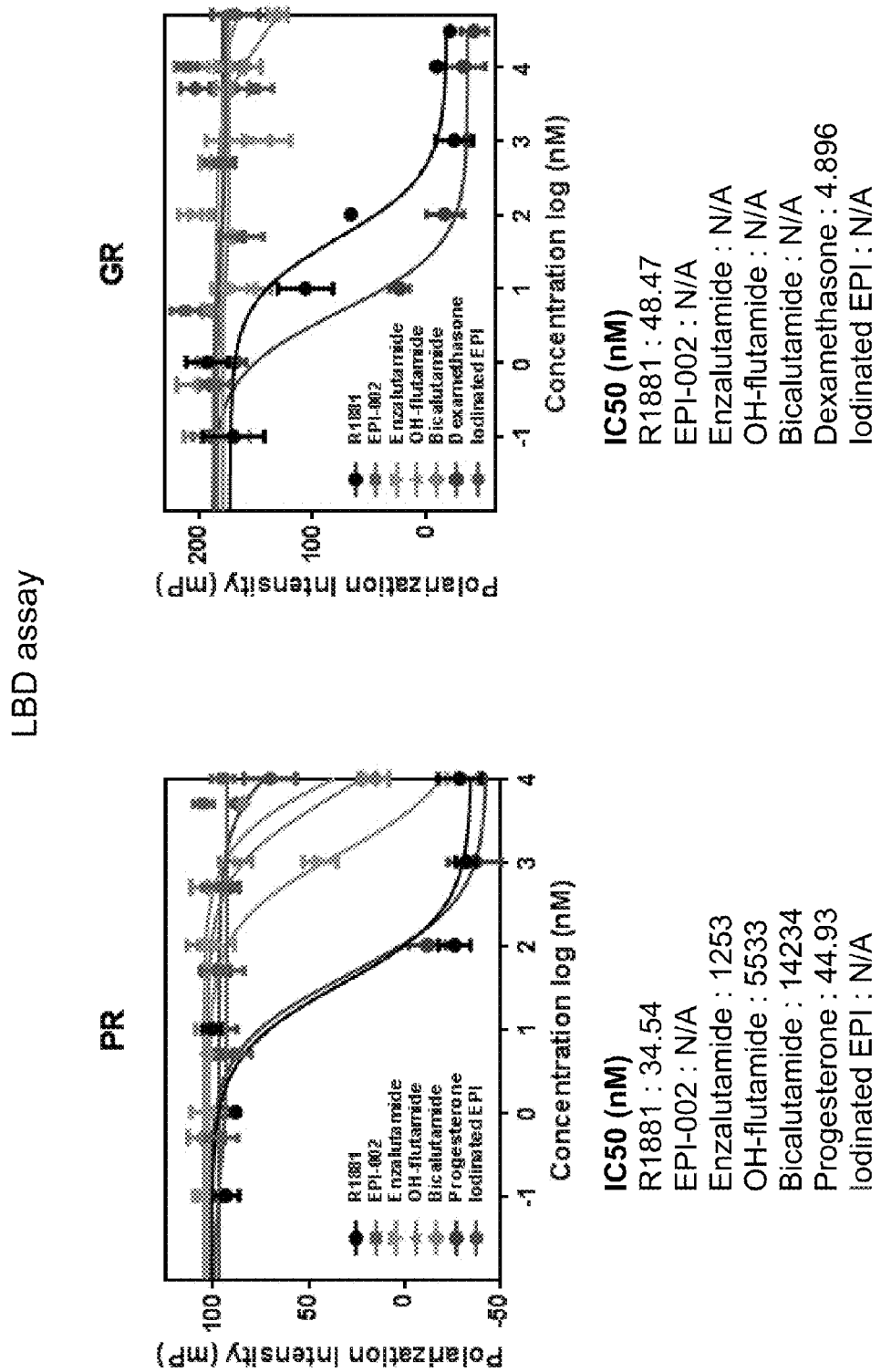

HALOGENATED COMPOUNDS FOR CANCER IMAGING AND TREATMENT AND METHODS FOR THEIR USE

PRIORITY INFORMATION

This application claims the benefit of U.S. Provisional Application No. 61/875,556, filed on Sep. 9, 2013, and which is incorporated herein be reference in its entirety.

STATEMENT OF GOVERNMENT INTEREST

This invention was made in part with government support under Grant No. 2R01 CA105304 awarded by the National Cancer Institute. The United States Government has certain rights in this invention.

BACKGROUND

1. Technical Field

This invention generally relates to radiolabeled compounds and their use in methods for imaging the prostate gland. For example, in certain embodiments the compounds are useful for imaging benign prostate diseases such as benign prostate hyperplasia. In other embodiments, the compounds are useful for imaging cancerous prostate diseases, such as prostate cancer tumors. In certain embodiments the invention relates to radioactive $^{123}$I compounds and their use as an imaging tool in prostate cancer and benign prostate diseases. The disclosed compounds find utility in any number of imaging applications, including imaging of androgen receptor (AR) splice variants in prostate cancers, including all stages and androgen dependent, androgen-sensitive and castration-resistant prostate cancers (also referred to as hormone refractory, androgen-independent, androgen deprivation resistant, androgen ablation resistant, androgen depletion-independent, castration-recurrent, anti-androgen-recurrent).

2. Description of the Related Art

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration (androgen ablation).

Androgens also play a role in female diseases such as polycystic ovary syndrome as well as cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). The AR has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate epithelial cells. Androgen ablation therapy causes a temporary reduction in tumor burden concomitant with a decrease in serum prostate-specific antigen (PSA). Unfortunately prostate cancer can eventually grow again in the absence of testicular androgens (castration-resistant disease) (Huber et al 1987 *Scand J. Urol Nephrol.* 104, 33-39). Castration-resistant prostate cancer is biochemically characterized before the onset of symptoms by a rising titre of serum PSA (Miller et al 1992 *J. Urol.* 147, 956-961). Once the disease becomes castration-resistant most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains one or more transcriptional activation domains. Binding of androgen (ligand) to the LBD of the AR results in its activation such that the receptor can effectively bind to its specific DNA consensus site, termed the androgen response element (ARE), on the promoter and enhancer regions of "normally" androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J. Biol. Chem.* 271, 19900-19907; Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The mechanism of ligand-independent transformation of the AR has been shown to involve: 1) increased nuclear AR protein suggesting nuclear translocation; 2) increased AR/ARE complex formation; and 3) the AR-NTD (Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The AR may be activated in the absence of testicular androgens by alternative signal transduction pathways in castration-resistant disease, which is consistent with the finding that nuclear AR protein is present in secondary prostate cancer tumors (Kim et al 2002 *Am. J. Pathol.* 160, 219-226; and van der Kwast et al 1991 *Inter. J. Cancer* 48, 189-193).

Available inhibitors of the AR include nonsteroidal antiandrogens such as bicalutamide (Casodex™), nilutamide, flutamide, enzulutamide and investigational drug ARN-509 and steroidal antiandrogens, such as cyproterone acetate. These antiandrogens target the LBD of the AR and predominantly fail presumably due to poor affinity and mutations that lead to activation of the AR by these same antiandrogens (Taplin, M. E., Bubley, G. J., Kom Y. J., Small E. J., Uptonm M., Rajeshkumarm B., Balkm S. P., *Cancer Res.*, 59, 2511-2515 (1999)).

These antiandrogens would also have no effect on the recently discovered AR splice variants that lack the ligand-binding domain (LBD) to result in a constitutively active receptor which promotes progression of castration recurrent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009; Hu et al 2009 Cancer Res. 69, 16-22; Sun et al 2010 J Clin Invest. 2010 120, 2715-30).

Conventional therapy has concentrated on androgen-dependent activation of the AR through its C-terminal domain. Studies developing antagonists to the AR have concentrated on the C-terminus and specifically: 1) the allosteric pocket and AF-2 activity (Estébanez-Perpiñá et al 2007, *PNAS* 104, 16074-16079); 2) in silico "drug repurposing" procedure for identification of nonsteroidal antagonists (Bisson et al 2007, *PNAS* 104, 11927-11932); and coactivator or corepressor interactions (Chang et al 2005, *Mol Endocrinology* 19, 2478-2490; Hur et al 2004, *PLoS Biol* 2, E274; Estébanez-Perpiñá et al 2005, *JBC* 280, 8060-8068; He et al 2004, *Mol Cell* 16, 425-438).

The AR-NTD is also a target for drug development (e.g. WO 2000/001813), since the NTD contains Activation-Function-1 (AF-1) which is the essential region required for AR transcriptional activity (Jenster et al 1991. Mol Endocrinol. 5, 1396-404). The AR-NTD importantly plays a role in activation of the AR in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104, 1331-1336).

While the crystal structure has been resolved for the AR C-terminus LBD, this has not been the case for the NTD due to its high flexibility and intrinsic disorder in solution (Reid et al 2002 *J. Biol. Chem.* 277, 20079-20086) thereby hampering virtual docking drug discovery approaches. Compounds that modulate AR include the bis-phenol compounds disclosed in published PCT Nos: WO 2010/000066, WO 2011/082487; WO 2011/082488; WO 2012/145330; WO 2012/139039; WO 2012/145328; WO 2013/028572 and WO 2013/028791, which are hereby incorporated by reference in their entireties, to the British Columbia Cancer Agency Branch and The University of British Columbia.

In addition to compounds which modulate AR, compounds and methods for imaging the prostate are useful research, diagnostic and prognostic tools. Such compounds are useful in many applications, including imaging of benign and/or malignant prostate cells and tissue. In this regard, positron emission tomography (PET) is an often used imaging technique for non-invasive identification of pathological state and tumors. In PET imaging, the distribution of a radioisotope (e.g., $^{18}F$) in the body can be determined. Thus incorporating $^{18}F$ into compounds which concentrate in tumor sites (see e.g., WO 2013/028791) offers potential for diagnosis, staging, and monitoring treatment of cancers. However, improved methods for imaging are needed, for example methods which employ $^{123}I$ and single photon emission coupled tomography (SPECT) techniques have potential to improve methods for imaging AR-rich tissues such as the benign prostate, and in particular prostate cancers and AR splice variants in castrate recurrent prostate cancers.

While significant advances have been made in this field, there remains a need for improved imaging agents In particular, methods and compounds suitable for imaging benign and malignant prostate tissues and cells are needed. The present invention fulfills these needs, and provides other related advantages.

BRIEF SUMMARY

Some embodiments of the compounds described herein may be used for diagnostic purposes to investigate diseases of the prostate, including cancer. In particular embodiments, the compounds are useful for imaging diagnostics in cancer. In some embodiments, such imaging allows for the detection and/or location of cancer sites (e.g., tumor sites). Furthermore, these compounds may be used individually or as part of a kit for such purposes.

The present disclosure is based in part on the surprising discovery that the compounds described herein, may be used to modulate AR activity either in vivo or in vitro for both research and therapeutic uses. Accordingly, embodiments of the compounds are useful for imaging the prostate. The imaging may be for any number of diagnostic purposes. For example, in certain embodiments the compounds are useful for imaging benign prostate cancer diseases. In other embodiments, the compounds find utility for imaging of certain cancers, including prostate cancer since certain embodiments of the compounds localize in prostate tumor sites. Other imaging agents are androgen mimics; however, in one embodiment, the compounds are useful for imaging AR splice variants or any AR species (ie., those mutated in other domains or regions). The AR may be mammalian. For example, the AR may be human. The prostate cancer may be castration-resistant prostate cancer. The prostate cancer may be androgen-dependent prostate cancer.

In accordance with one embodiment, there is provided a compound having a structure of Formula I:

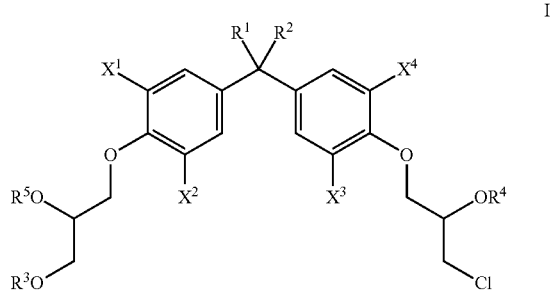

or a pharmaceutically acceptable salt, tautomer or stereoisomer thereof, wherein $R^1$, $R^2$, $R^3$, $R^4$, $R^5$, $X^1$, $X^2$, $X^3$ and $X^4$ are as defined herein, and wherein the compound comprises at least one F, Cl, Br, I or $^{123}I$ moiety, are provided.

In other embodiments pharmaceutical compositions comprising a compound of structure (I) are provided. Methods employing such pharmaceutical compositions for imaging cancer are also provided. Methods for modulating AR activity employing the present compounds and pharmaceutical compositions are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

FIGS. 1A and 1B are graphs showing dose response of a representative compound (8d) of the invention.

FIGS. 2A-2D shows specificity of a representative compound (8d) relative to comparative compounds.

FIGS. 3A-3C show the characterization data for compound iii-I.

FIGS. 4A-4C show the characterization data for compound iii-Br.

FIGS. 6A and 6B show the characterization data for compound iv-I.

FIGS. 7A-7C show the characterization data for compound iv-Br.

FIGS. 8A-8C show the characterization data for compound 8d.

FIGS. 9A-9C show the characterization data for compound 9d.

FIGS. 10A-10C show the characterization data for compound 10d.

FIGS. 12A and 12B show the characterization data for compound iv-F.

FIGS. 13A-13C show the characterization data for compound 11d.

FIGS. 14A-14E show competitive ligand-binding assay of 8d and representative ligands from recombinant ligand binding domains.

DETAILED DESCRIPTION

I. Definitions

Figures 2A, 2B:
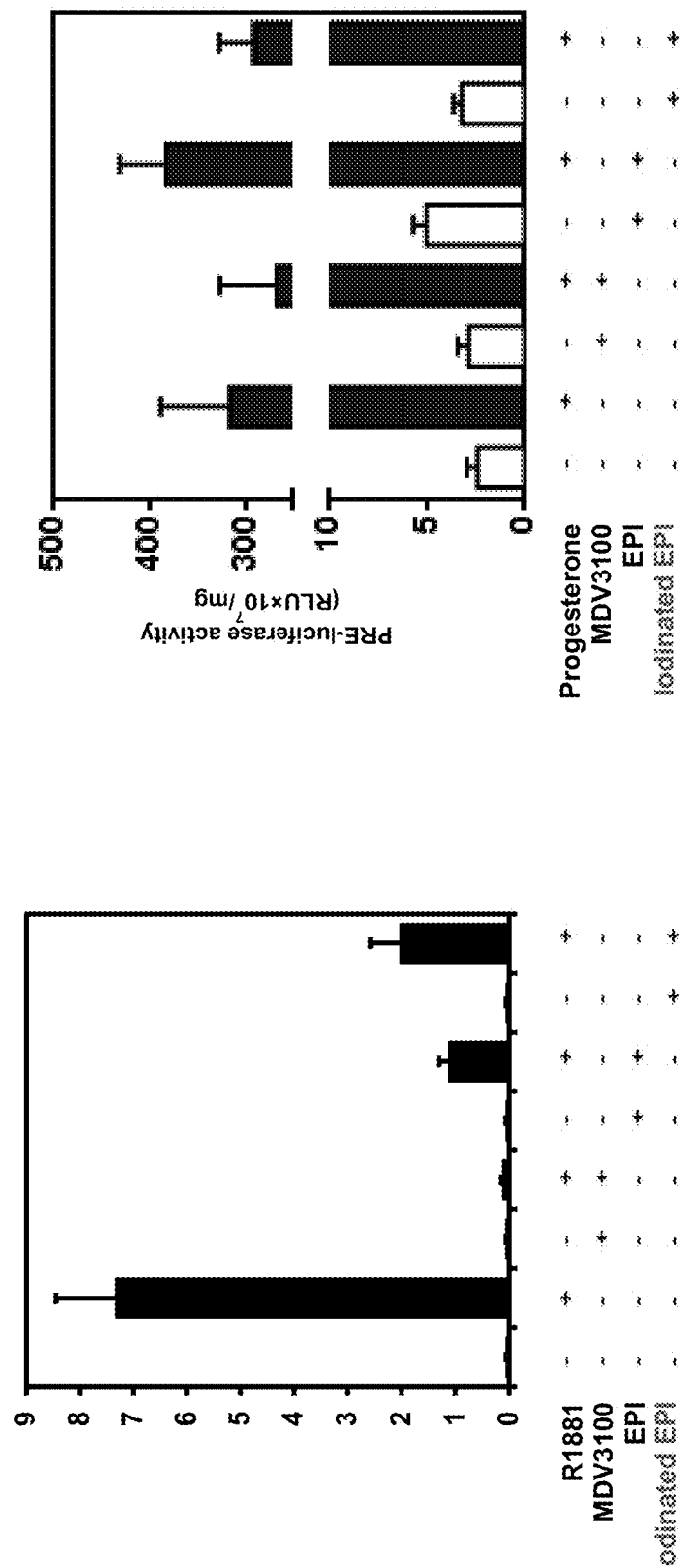
Figure 4A:
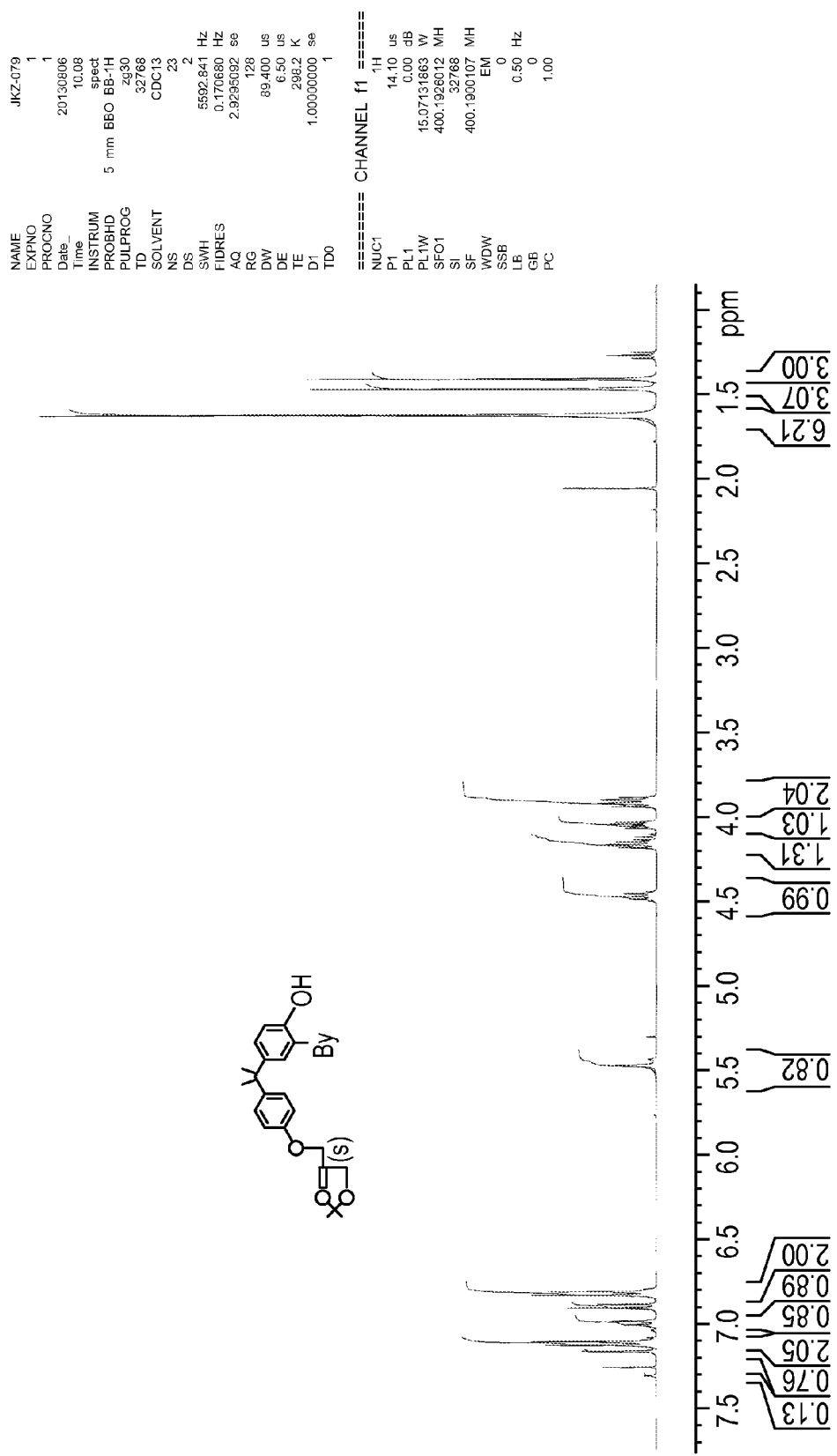
Figure 5A:
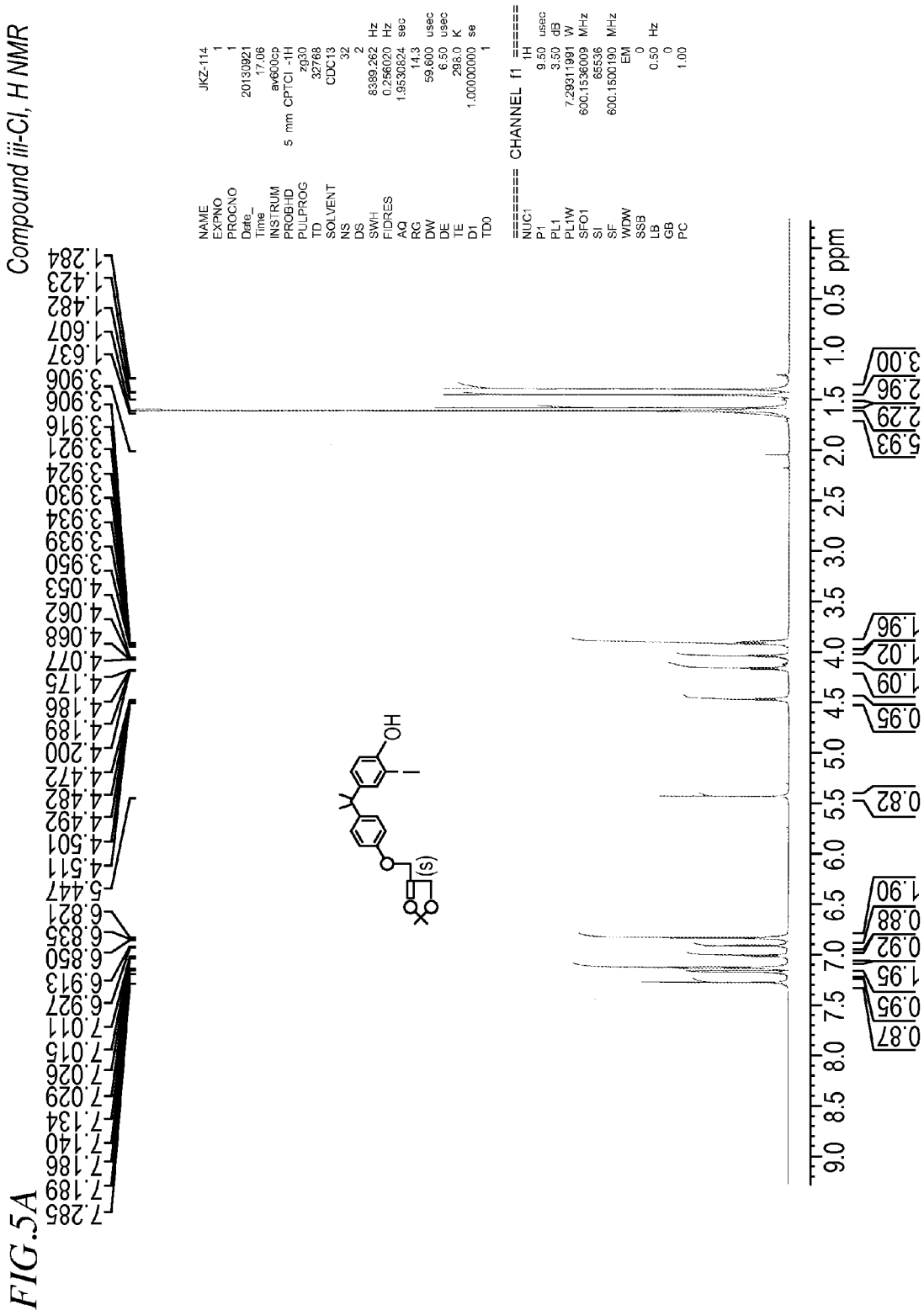
FIGS. 5A and 5B show the characterization data for compound iii-Cl.
Figure 5B:
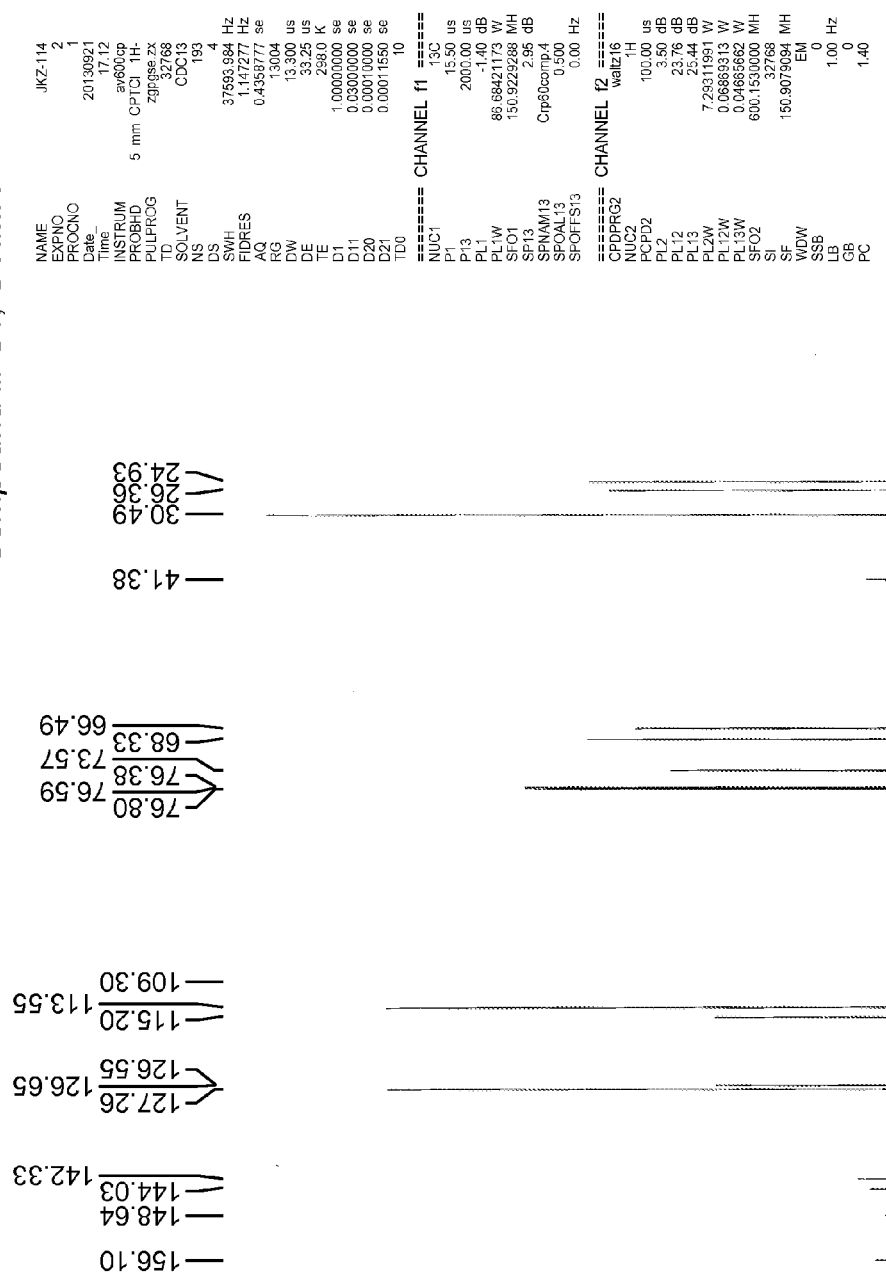
Figure 6B:
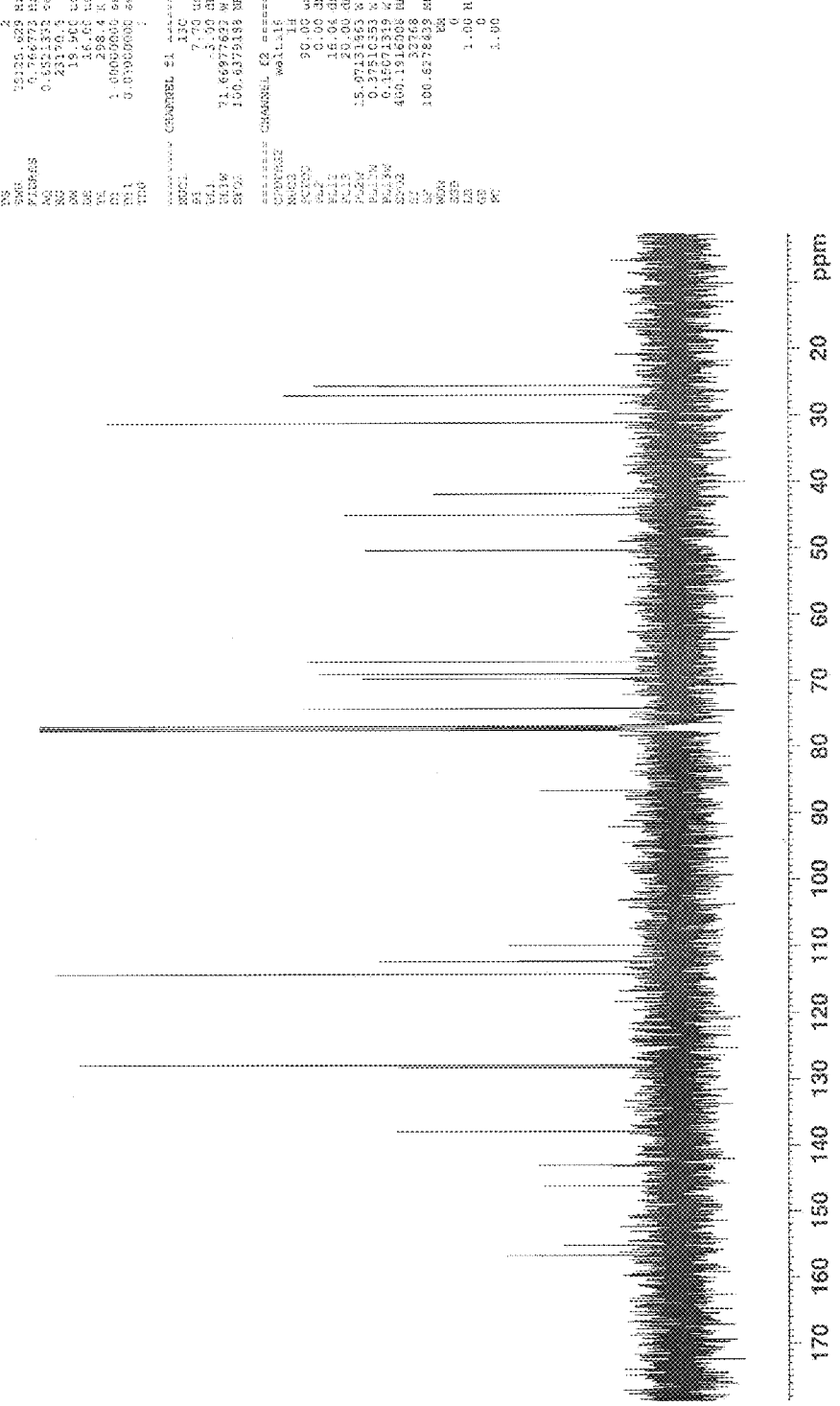
Figure 7B:
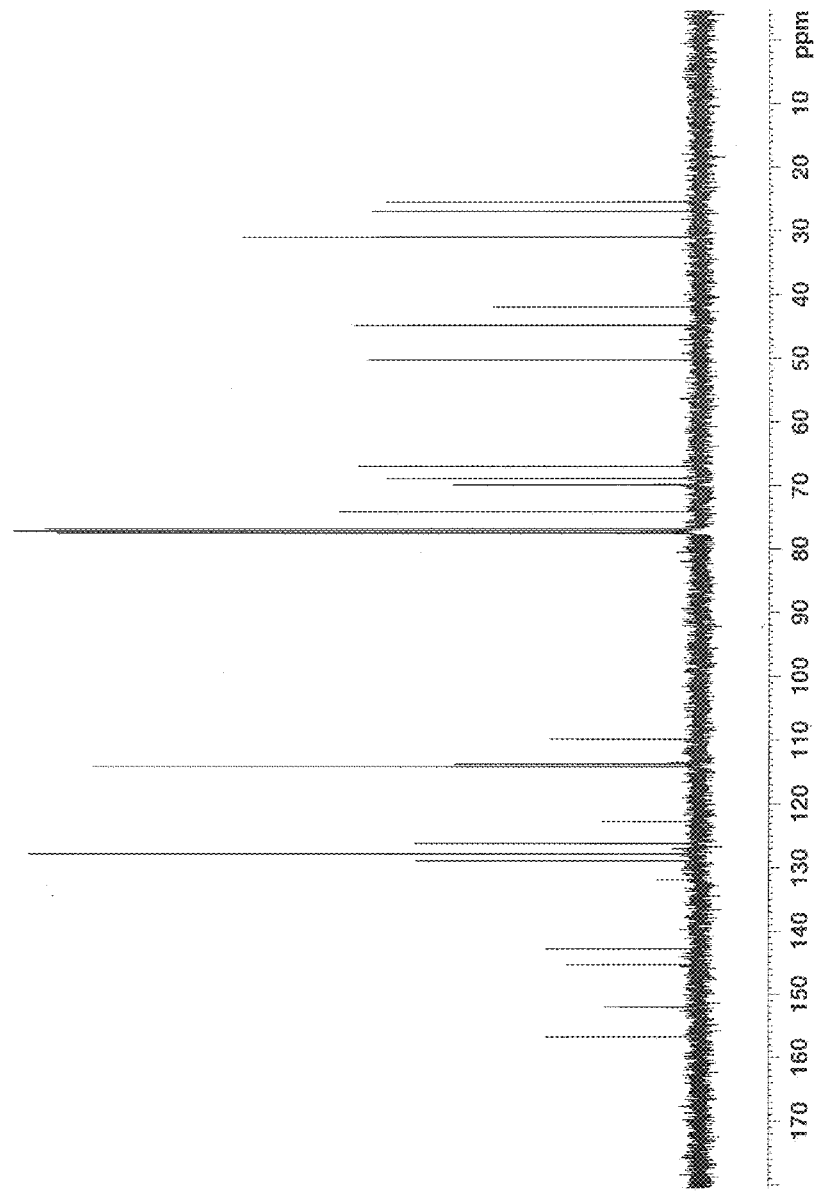
Figure 7C:
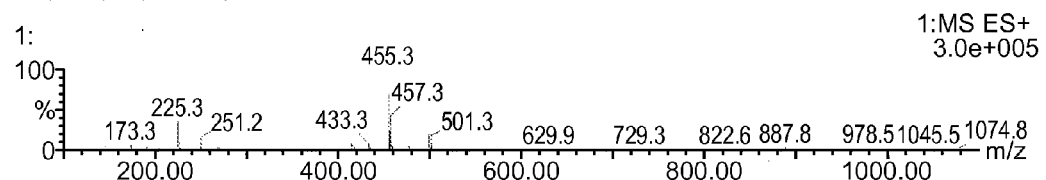
Figure 8B:
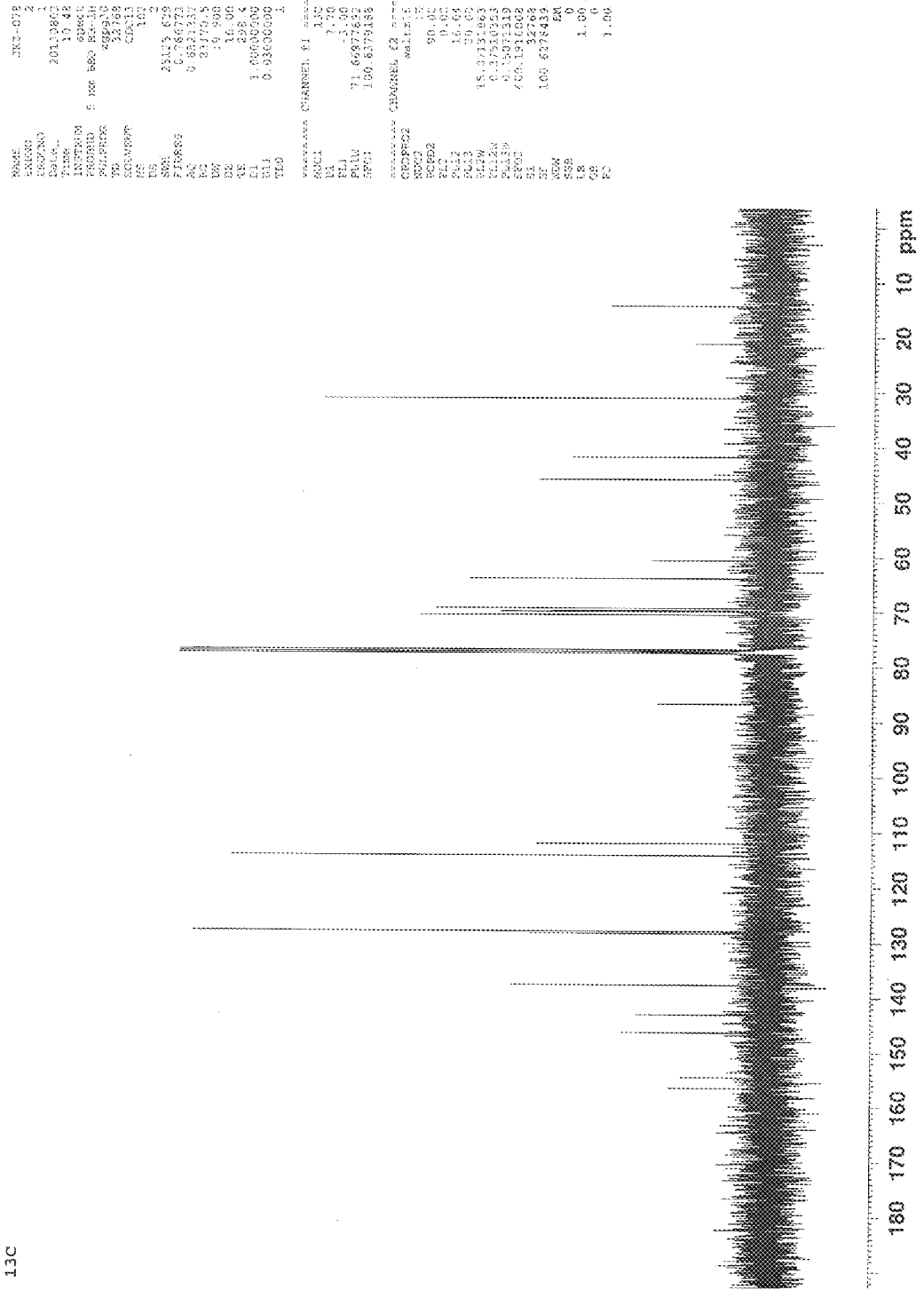
Figure 9B:
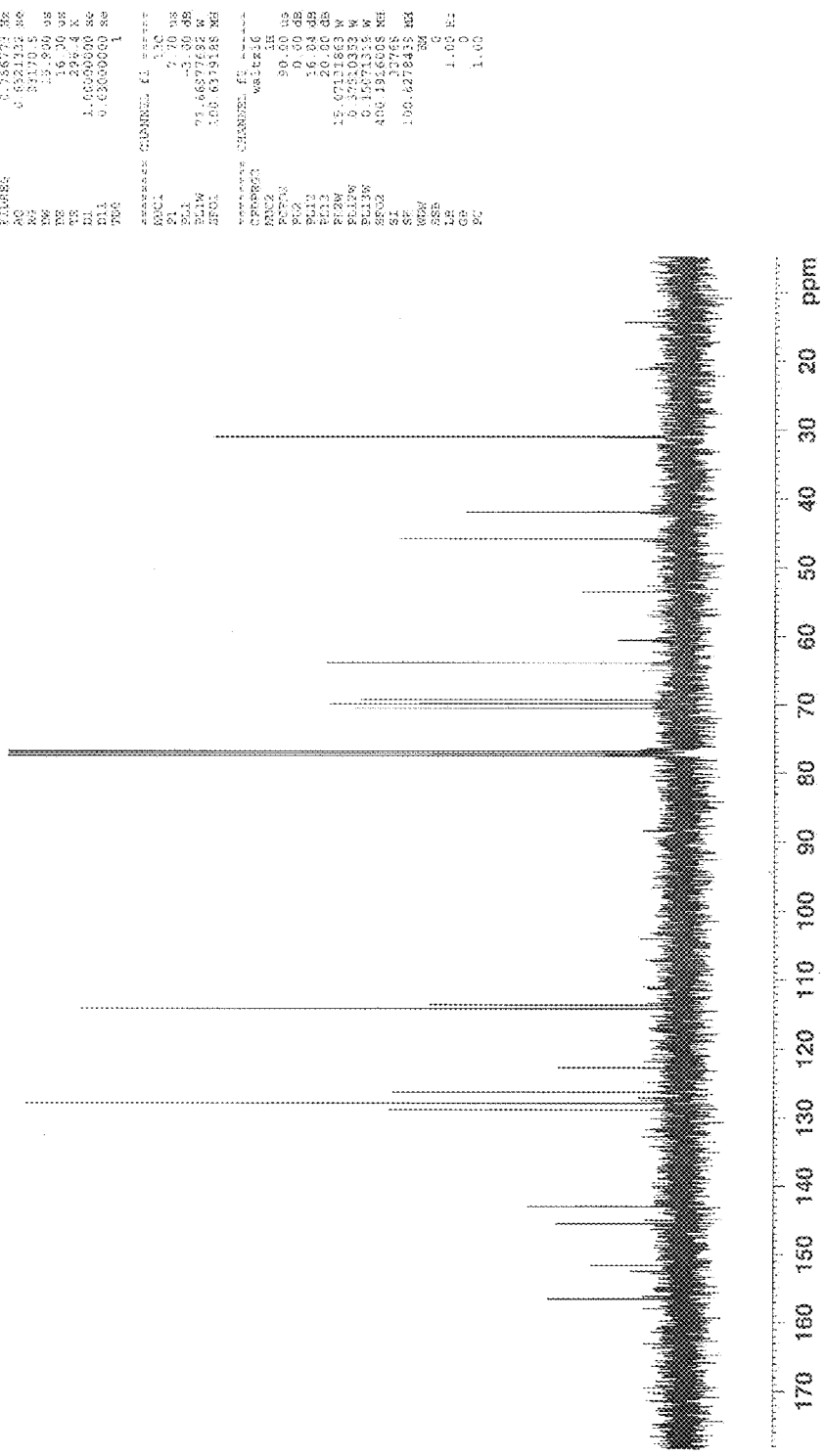
Figure 10B:
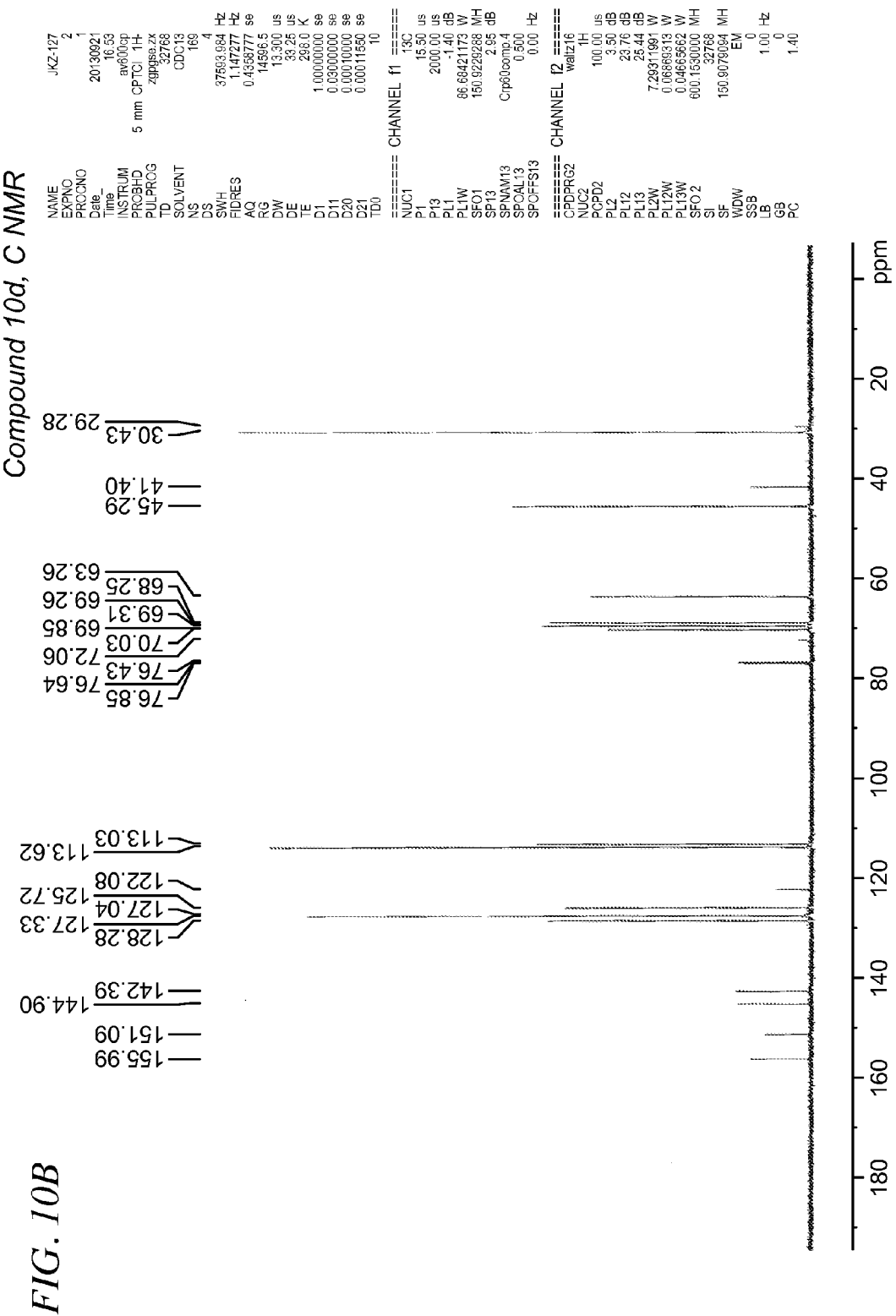
Figure 11:
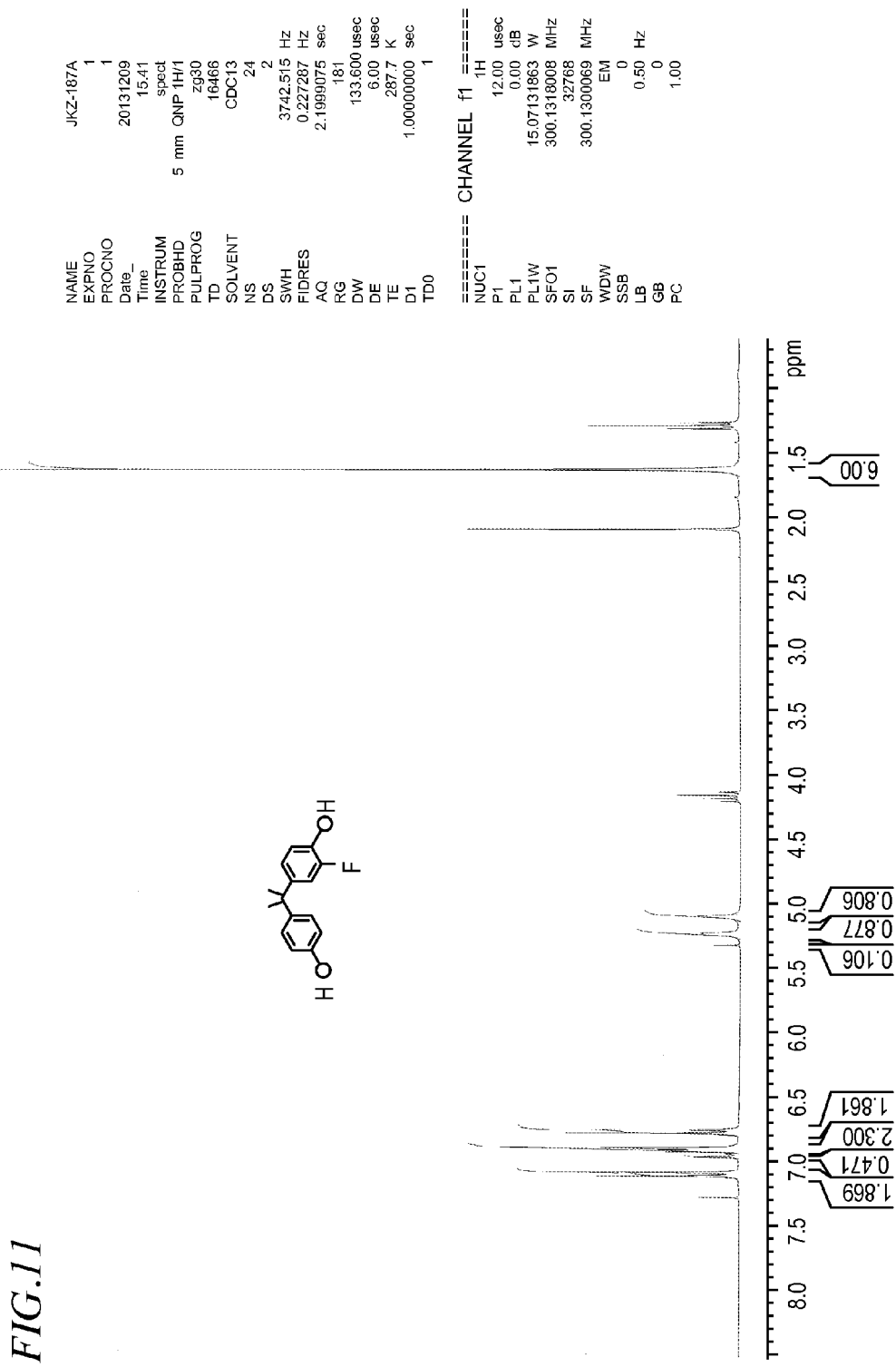
FIG. 11 shows the characterization data for compound v-F.
Figure 12B:
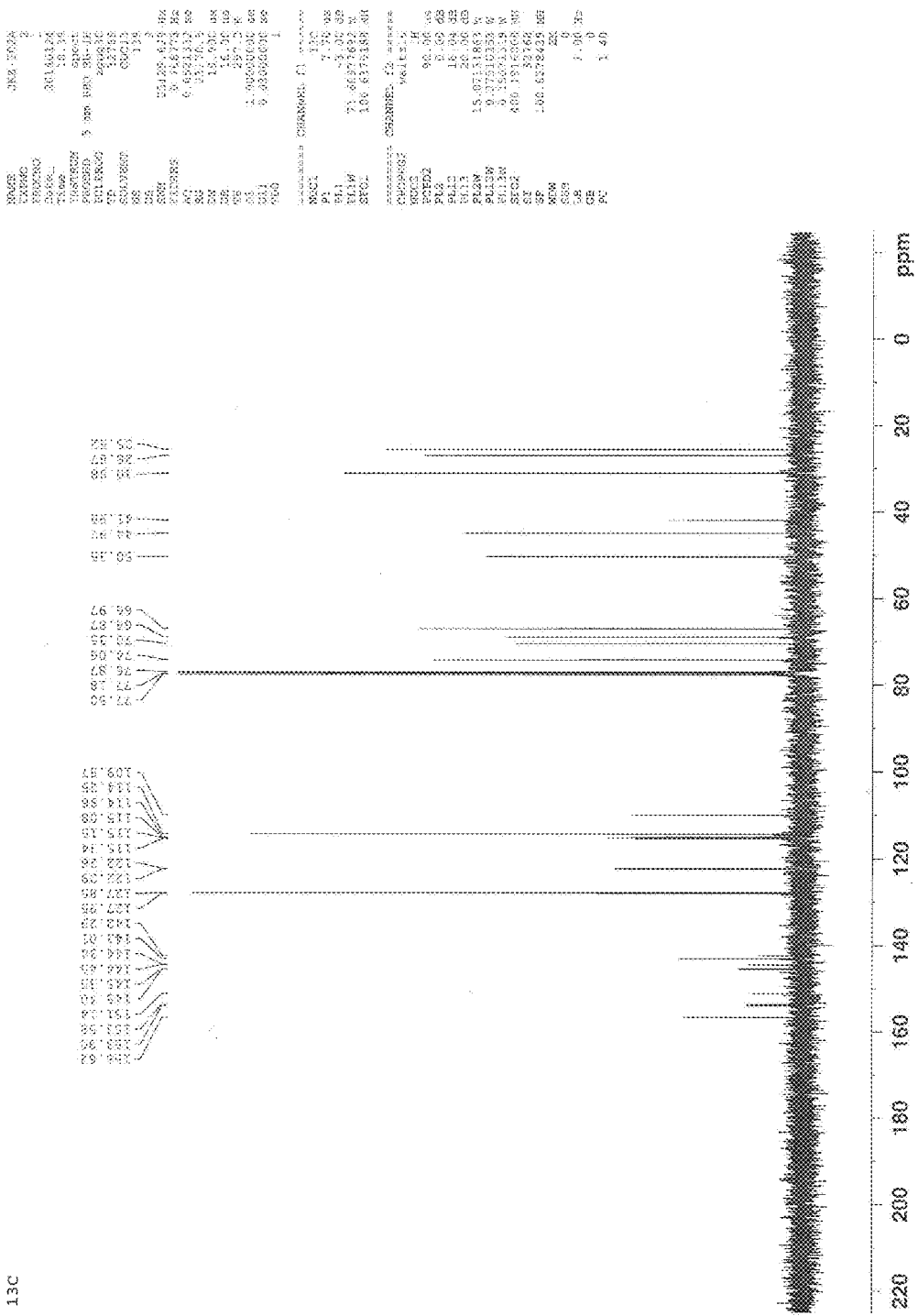
Figure 13A:
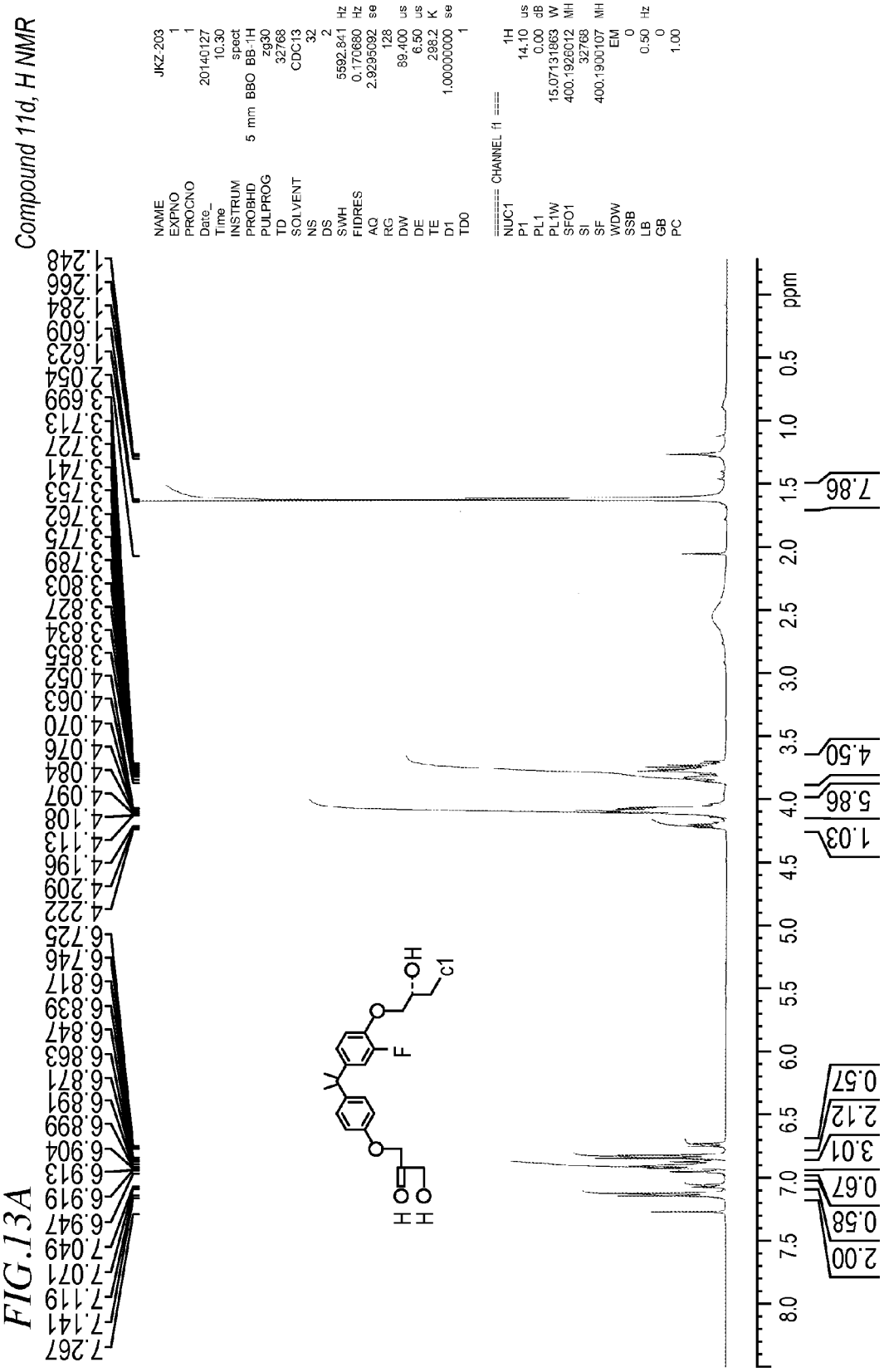
Figure 14A:
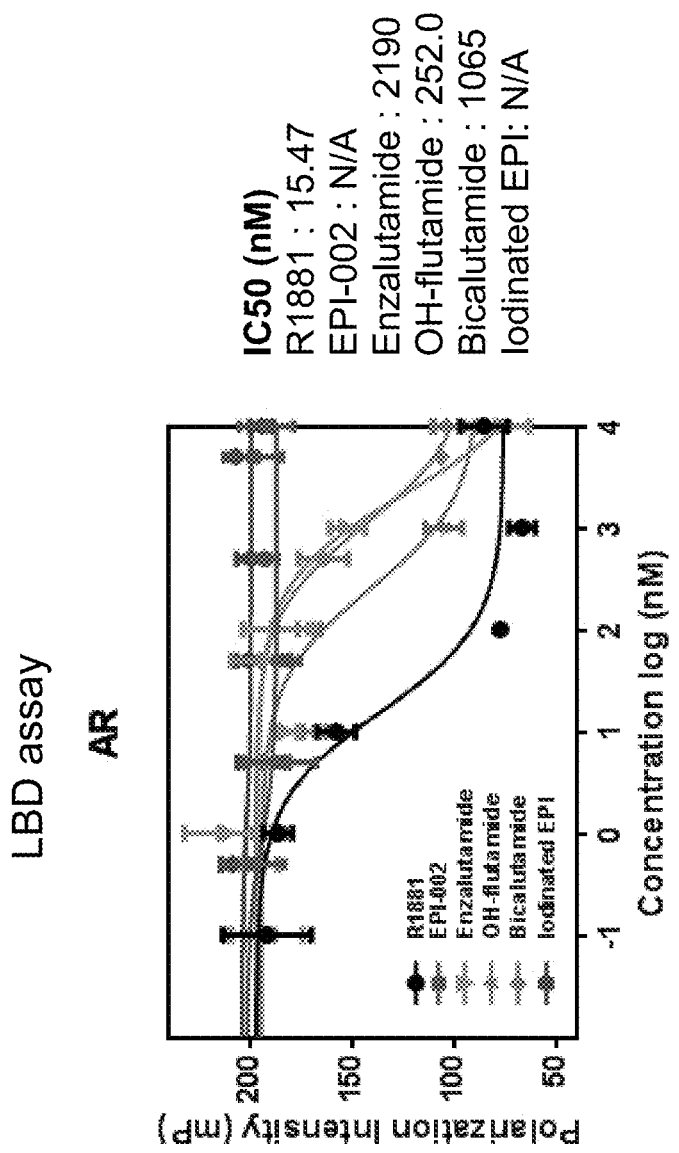
Figures 14D, 14E:
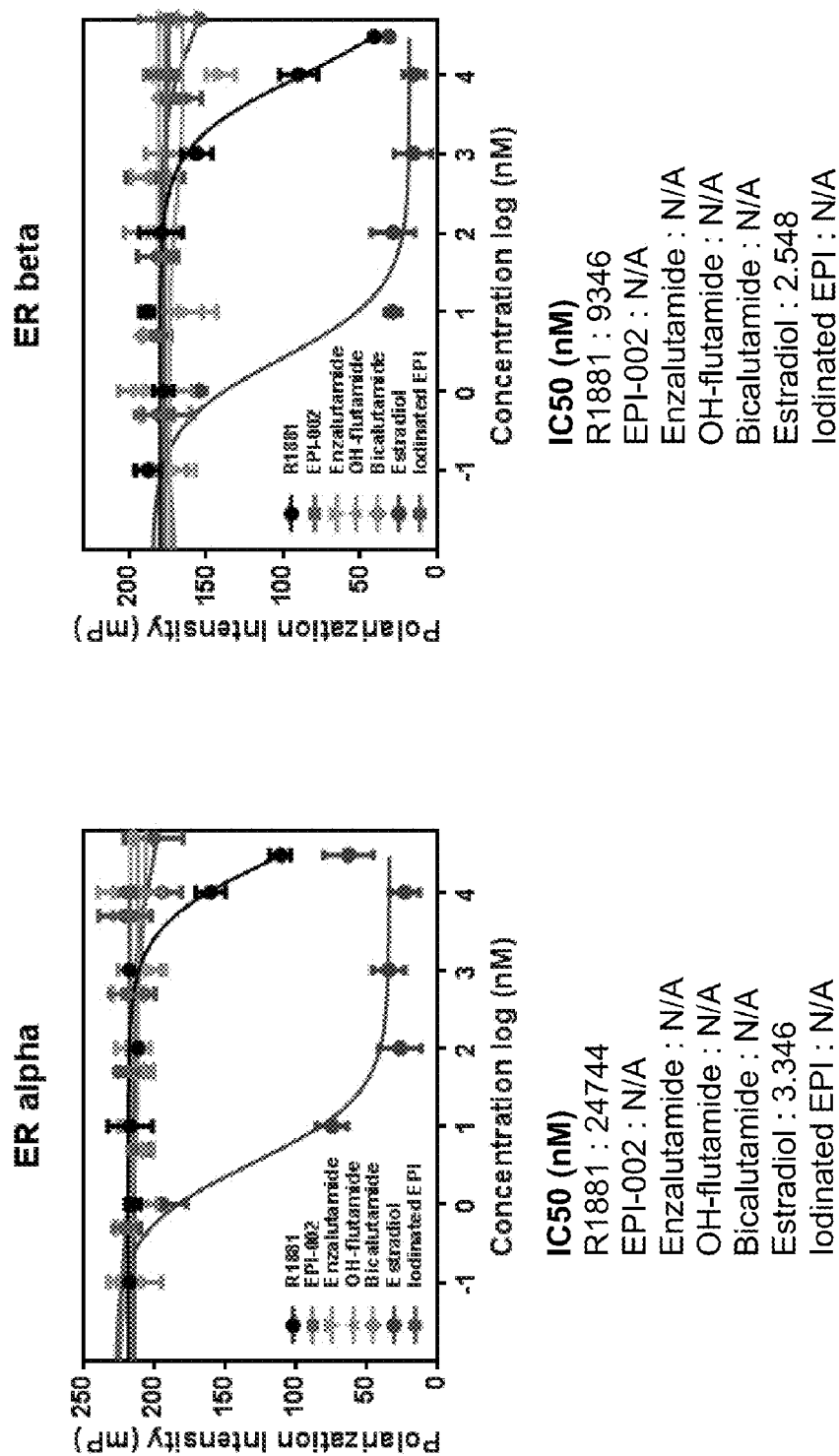

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the $-NH_2$ radical.

"Cyano" refers to the $-CN$ radical.

"Halo" or "halogen" refers to bromo, chloro, fluoro or iodo.

"Hydroxy" or "hydroxyl" refers to the $-OH$ radical.

"Imino" refers to the $=NH$ substituent.

"Nitro" refers to the $-NO_2$ radical.

"Oxo" refers to the $=O$ substituent.

"Thioxo" refers to the $=S$ substituent.

"Alkyl" refers to a straight or branched hydrocarbon chain radical which is saturated or unsaturated (i.e., contains one or more double and/or triple bonds), having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl) and includes, for example, and without limitation, saturated $C_1$-$C_5$ alkyl, $C_2$-$C_5$ alkenyl and $C_2$-$C_5$ alkynyl. Non-limiting examples of saturated $C_1$-$C_5$ alkyl include methyl, ethyl, n-propyl, i-propyl, sec-propyl, n-butyl, i-butyl, sec-butyl, t-butyl and n-pentyl. Non-limiting examples of $C_2$-$C_5$ alkenyl include vinyl, allyl, isopropenyl, 1-propene-2-yl, 1-butene-1-yl, 1-butene-2-yl, 1-butene-3-yl, 2-butene-1-yl, 2-butene-2-yl, penteneyl and the like. Non-limiting examples of $C_2$-$C_5$ alkynyl include ethynyl, propynyl, butynyl, pentynyl and the like. A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Unless stated otherwise specifically in the specification, an alkyl group may be optionally substituted. "Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula $-OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Alkylcarbonyl" refers to the —C(=O)Ra moiety, wherein Ra is an alkyl radical as defined above. A non-limiting example of an alkyl carbonyl is the methyl carbonyl ("acetal") moiety. Unless stated otherwise specifically in the specification, an alkyl carbonyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Carbocyclyl" or "carbocyclic ring" refers to a rings structure, wherein the the atoms which form the ring are each carbon. Carbocyclic rings may comprise from 3 to 18 carbon atoms in the ring. Carbocyclic rings include aryls and cycloalkyls as defined herein. Unless stated otherwise specifically in the specification, a carbocyclyl group may be optionally substituted.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group may be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$, where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$— where $R_b$ is an alkylene chain as defined above and $R_f$ is a heteroaryl radical as defined above. Unless stated otherwise specifically in the specification, a heteroarylalkyl group may be optionally substituted.

"$^{123}$I" refers to the radioactive isotope of iodine having atomic mass 123. The compounds of structure (I) comprise at least one $^{123}$I moiety. Throughout the present application, where structures depict a $^{123}$I moiety at a certain position it is meant that the I moiety at this position is enriched for $^{123}$I. In other words, the compounds contain more than the natural abundance of $^{123}$I at the indicated position(s). It is not required that the compounds comprise 100% $^{123}$I at the indicated positions, provided $^{123}$I is present in more than the natural abundance. Typically the $^{123}$I isotope is enriched to greater than 50%, greater than 60%, greater than 70%, greater than, 80% or greater than 90%, relative to $^{127}$I.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

The term "substituted" used herein means any of the above groups (i.e., alkyl, alkylene, alkoxy, alkylamino, alkylcarbonyl, thioalkyl, aryl, aralkyl, carbocyclyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)N\ R_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

As used herein, the symbol "⫲" (hereinafter may be referred to as "a point of attachment bond") denotes a bond that is a point of attachment between two chemical entities, one of which is depicted as being attached to the point of attachment bond and the other of which is not depicted as being attached to the point of attachment bond. For example, "XY⫲" indicates that the chemical entity "XY" is bonded to another chemical entity via the point of attachment bond. Furthermore, the specific point of attachment to the non-depicted chemical entity may be specified by inference. For example, the compound $CH_3$—$R^3$, wherein $R^3$ is H or "XY⫲" infers that when $R^3$ is "XY", the point of attachment bond is the same bond as the bond by which $R^3$ is depicted as being bonded to $CH_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)-for amino acids. The present invention is meant to include all such possible isomers, as well as their racemic and optically pure forms whether or not they are specifically depicted herein. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

II. Compounds and Methods

As noted above, the presently disclosed compounds find utility in a number of medical imaging application, including imaging of the prostate. Many currently available imaging agents tend to accumulate in the bladder, which decreases their effectiveness as imaging tools specifically for the prostate. While not wishing to be bound by theory, the present applicants believe the disclosed compounds are unexpectedly effective for imaging of the prostate due to their ability to accumulate in the prostate, rather than the bladder, allowing the prostate gland to be seen. Accordingly, the compounds may be used in methods for imaging the prostate, for example to image benign prostate diseases. In other embodiments, the compounds may be used in methods to image cancerous prostate diseases, such as tumors of the prostate.

Androgen ablation therapy causes a temporary reduction in prostate cancer tumor burden, but the malignancy will begin to grow again in the absence of testicular androgens to form castrate resistant prostate cancer (CRPC). A rising titer of serum prostate-specific antigen (PSA) after androgen ablation therapy indicates biochemical failure, the emergence of CRPC, and re-initiation of an androgen receptor (AR) transcription program. Most patients succumb to CRPC within two years of biochemical failure.

AR is a transcription factor and a validated target for prostate cancer therapy. Current therapies include androgen ablation and administration of antiandrogens. Most CRPC is suspected to be AR-dependent. AR has distinct functional domains that include the C-terminus ligand-binding domain (LBD), a DNA-binding domain (DBD), and an amino-terminal domain (NTD). AR NTD contains the activation function-1 (AF-1) that contributes most of the activity to the AR. Recently, splice variants of the AR that lack the LBD have been reported in prostate cancer cell lines (VCaP and 22Rv1), and in CRPC tissues. To date more than 20 splice variants of AR have been detected. Splice variants V7 and V567es are clinically relevant with levels of expression correlated to poor survival and CRPC. AR V567es is solely expressed in 20% of metastases. Abiraterone resistance is associated with expression of AR splice variants. Enzalutamide also increases levels of expression of these constitutively active AR splice variants. These splice variants lack LBD and thereby would not be inhibited by current therapies that target the AR LBD such as antiandrogens or androgen ablation therapy. A single patient with advanced prostate cancer can have many lesions throughout the body and skeleton and each tumor can have differing levels of expression of AR.

Biopsy of metastatic tumors in a patient to determine AR species is not widely accessible nor feasible to sample tumours in a patient that may have multiple metastases. Thus it is essential to develop approaches to detect the expression of all AR species for the molecular classification of tumors based on the level and extent of expression of AR splice variants, or other AR species that cannot be detected using an imaging agent that interacts with the LBD, to identify patients with potentially aggressive disease and poor prognosis, or to identify patients that will not respond to hormone therapies that target the AR LBD. Accordingly, certain embodiments of the present invention provide a AR NTD-targeted molecular imaging probe (e.g., compound of formula I) which can be used to monitor response to therapy and provide insight into the role of AR in resistance mechanisms.

One current approach to image AR in prostate cancer uses positron emission tomography (PET) with 16β-[$^{18}$F]-fluoro-5α dihydrotestosterone ($^{18}$F-FDHT) that binds to AR LBD. Unfortunately this imaging agent cannot detect splice variants lacking LBD. In some embodiments, the invention employs sequential imaging with $^{18}$F-FDHT to detect full-length AR and gamma radiation emitting probes to specifically detect the AR NTD which would be the sum of both full-length AR and variant AR. In other embodiments, the invention employs sequential imaging with two different PET imaging agents to detects only full-length AR and another to specifically detect the AR NTD which would be the sum of both full-length AR and variant AR. Together these data reveal patients with tumors that express variant AR (NTD of variant plus full-length AR detected with NTD isotope minus full-length AR detected with $^{18}$F-FDHT). By using sequential imaging, a discordant distribution or discordant level of uptake between $^{18}$F-FDHT and a radiolabeled compound of this invention (i.e., compound of structure (I)) indicates the presence of overexpression of splice variants lacking the LBD.

Accordingly, certain embodiments of the present invention are directed to compounds that bind to the AR NTD and are useful for imaging of tumors with splice variants using SPECT and/or methods of modulating AR NTD activity. Other embodiments are directed to compound and methods useful for imaging and/or treating benign prostate conditions or diseases. In one embodiment, the present disclosure provides a compound having a structure of Formula I:

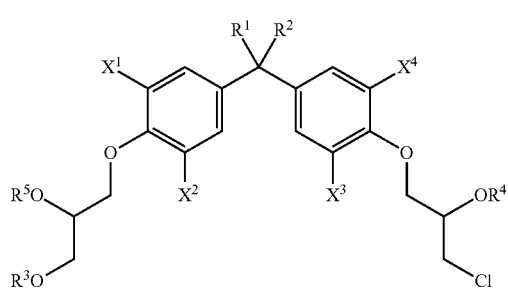

or a pharmaceutically acceptable salt, tautomer or stereoisomer thereof, wherein:

$R^1$ and $R^2$ are each independently H or $C_1$-$C_{10}$ alkyl, or $R^1$ and $R^2$, together with the carbon atom to which they are bound, are taken together to form a carbocyclic or heterocyclic ring;

$R^3$, $R^4$ and $R^5$ are each independently H, $C_1$-$C_{10}$ alkyl or $C_1$-$C_{10}$ alkylcarbonyl; and $X^1$, $X^2$, $X^3$ and $X^4$ are each independently H, F, Cl, Br, I or $^{123}$I, wherein at least one of $X^1$, $X^2$, $X^3$ or $X^4$ is F, Cl, Br, I or $^{123}$I.

In various embodiments, different stereoisomers of the compound of structure (I) are provided, for example in some embodiments the compound has one of the following structures (Ia), (Ib), (Ic) or (Id):

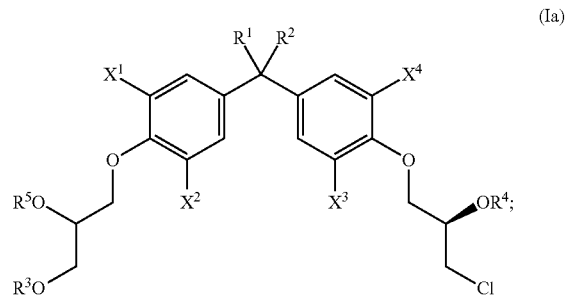

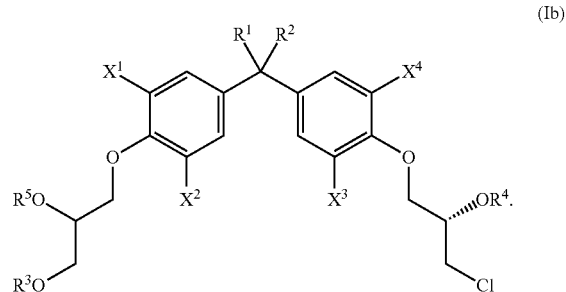

-continued (Ic)
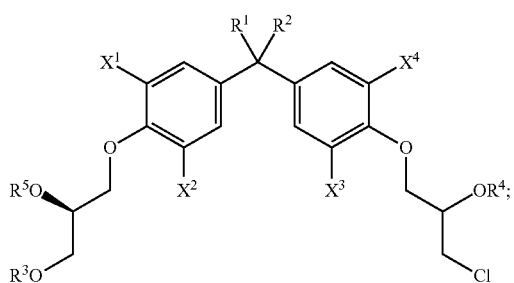

(Id)
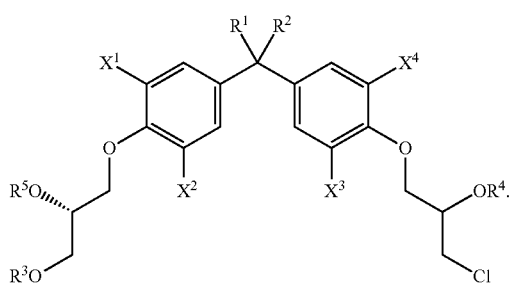

In still other embodiments, the compound has one of the following structures (Ie), (If), (Ig) or (Ih):

(Ie)
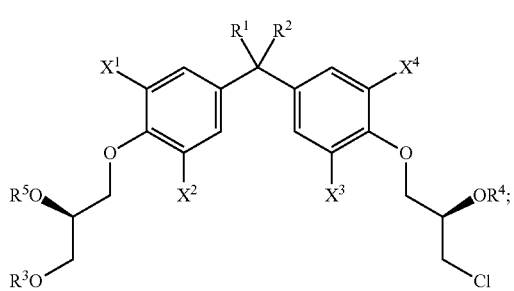

(If)
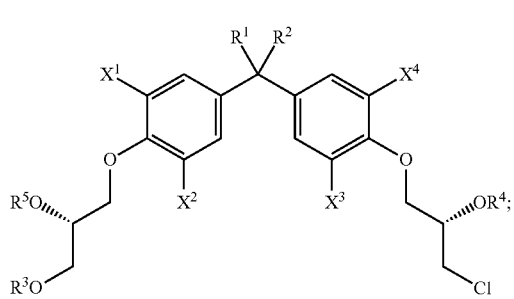

(Ig)
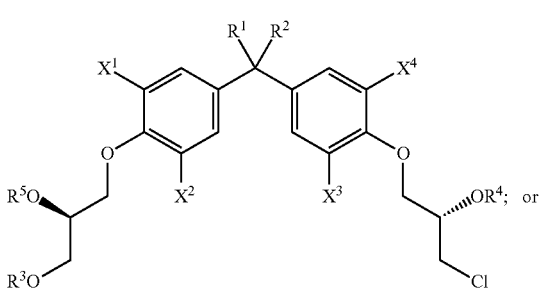

(Ih)
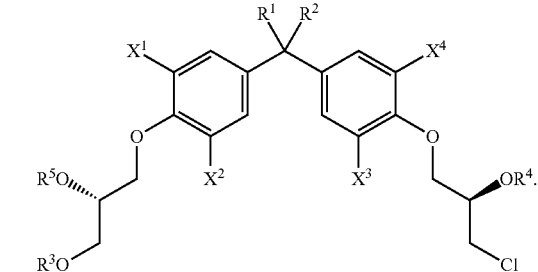

The compounds contain at least one F, Cl. Br, I or $^{123}$I substitution for use in the imaging and treatment methods described herein. In some embodiments, the compounds comprise one F, Cl. Br, I or $^{123}$I substitution, for example in certain other embodiments, three of $X^1$, $X^2$, $X^3$ and $X^4$ are H, and the remaining $X^1$, $X^2$, $X^3$ or $X^4$ is F, Cl. Br, I or $^{123}$I. In some embodiments, the compounds comprise two F, Cl. Br, I or $^{123}$I substitutions (i.e., two of $X^1$, $X^2$, $X^3$ and $X^4$ are H, and the other two of $X^1$, $X^2$, $X^3$ or $X^4$ are F, Cl. Br, I or $^{123}$I). In other embodiments, the compounds comprise three F, Cl. Br, I or $^{123}$I substitutions (i.e., one of $X^1$, $X^2$, $X^3$ and $X^4$ is H, and the remaining $X^1$, $X^2$, $X^3$ or $X^4$ is F, Cl. Br, I or $^{123}$I) and in other embodiments the compounds comprise four F, Cl, Br, I or $^{123}$I substitutions (i.e., each of $X^1$, $X^2$, $X^3$ and $X^4$ are F, Cl. Br, I or $^{123}$I).

Favorable imaging and/or AR NTD modulating results are obtained by substitution with F, Cl. Br, I or $^{123}$I at any of the "X" positions. In some of the foregoing embodiments, $X^1$ is $^{123}$I. In other of the $X^3$ is $^{123}$I.

In various embodiments of any of the foregoing, at least one of $R^1$ or $R^2$ is H. For example, in some embodiments $R^1$ and $R^2$ are each H.

In other embodiments of the foregoing, at least one of $R^1$ or $R^2$ is $C_1$-$C_{10}$ alkyl. For example, in some embodiments $R^1$ and $R^2$ are each $C_1$-$C_{10}$ alkyl. In some of these embodiments $C_1$-$C_{10}$ alkyl is $C_1$-$C_{10}$ saturated alky such as methyl.

In other embodiments, Each $R^1$ may independently be $C_1$-$C_5$ alkyl. Each $R^1$ may independently be $C_1$-$C_4$ alkyl. Each $R^1$ may independently be $C_1$-$C_3$ alkyl. Each $R^1$ may independently be $C_1$-$C_2$ alkyl. Each $R^1$ may independently be methyl. Each $R^1$ may independently be $C_2$ alkyl. Each $R^1$ may independently be $C_3$ alkyl. Each $R^1$ may independently be $C_4$ alkyl. Each $R^1$ may independently be $C_5$ alkyl.

In other embodiments, Each $R^2$ may independently be $C_1$-$C_5$ alkyl. Each $R^2$ may independently be $C_1$-$C_4$ alkyl. Each $R^2$ may independently be $C_1$-$C_3$ alkyl. Each $R^2$ may independently be $C_1$-$C_2$ alkyl. Each $R^2$ may independently be methyl. Each $R^2$ may independently be $C_2$ alkyl. Each $R^2$ may independently be $C_3$ alkyl. Each $R^2$ may independently be $C_4$ alkyl. Each $R^2$ may independently be $C_5$ alkyl.

In certain of the foregoing embodiments, at least one of $R^3$, $R^4$ or $R^5$ is H. In certain embodiments, two of $R^3$, $R^4$ and $R^5$ are H. In other embodiments, $R^3$, $R^4$ and $R^5$ are each H.

In still other embodiments of the foregoing compounds of structure (I), at least one of $R^3$, $R^4$ or $R^5$ is $C_1$-$C_{10}$ alkyl. For example, in some embodiments two of $R^3$, $R^4$ and $R^5$ are $C_1$-$C_{10}$ alkyl. In other embodiments, $R^3$, $R^4$ and $R^5$ are each $C_1$-$C_{10}$ alkyl. In certain of the foregoing embodiments, $C_1$-$C_{10}$ alkyl is saturated $C_1$-$C_{10}$ alkyl. For example, in some embodiments the saturated $C_1$-$C_{10}$ alkyl is methyl, isopropyl or n-butyl. In some different embodiments, the $C_1$-$C_{10}$ alkyl is unsaturated $C_1$-$C_{10}$ alkyl, for example propargyl.

In other embodiments, Each $R^3$ may independently be $C_1$-$C_5$ alkyl. Each $R^3$ may independently be $C_1$-$C_4$ alkyl. Each $R^3$ may independently be $C_1$-$C_3$ alkyl. Each $R^3$ may independently be $C_1$-$C_2$ alkyl. Each $R^3$ may independently be methyl. Each $R^3$ may independently be $C_2$ alkyl. Each $R^3$ may independently be $C_3$ alkyl. Each $R^3$ may independently be $C_4$ alkyl. Each $R^3$ may independently be $C_5$ alkyl.

In other embodiments, Each $R^4$ may independently be $C_1$-$C_5$ alkyl. Each $R^4$ may independently be $C_1$-$C_4$ alkyl. Each $R^4$ may independently be $C_1$-$C_3$ alkyl. Each $R^4$ may independently be $C_1$-$C_2$ alkyl. Each $R^4$ may independently be methyl. Each $R^4$ may independently be $C_2$ alkyl. Each $R^4$ may independently be $C_3$ alkyl. Each $R^4$ may independently be $C_4$ alkyl. Each $R^4$ may independently be $C_5$ alkyl.

In other embodiments, Each $R^5$ may independently be $C_1$-$C_5$ alkyl. Each $R^5$ may independently be $C_1$-$C_4$ alkyl. Each $R^5$ may independently be $C_1$-$C_3$ alkyl. Each $R^5$ may independently be $C_1$-$C_2$ alkyl. Each $R^5$ may independently be methyl. Each $R^5$ may independently be $C_2$ alkyl. Each $R^5$ may independently be $C_3$ alkyl. Each $R^5$ may independently be $C_4$ alkyl. Each $R^5$ may independently be $C_5$ alkyl.

In still other embodiments of some of the foregoing embodiments of the compound of structure (I), at least one of $R^3$, $R^4$ or $R^5$ is $C_1$-$C_{10}$ alkylcarbonyl. In some of these embodiments, two of $R^3$, $R^4$ and $R^5$ are $C_1$-$C_{10}$ alkylcarbonyl. In other of these embodiments, $R^3$, $R^4$ and $R^5$ are each $C_1$-$C_{10}$ alkylcarbonyl. In some more specific embodiments, the $C_1$-$C_{10}$ alkylcarbonyl is methyl carbonyl (acetal).

In other embodiments, Each $R^3$ may independently be $C_1$-$C_5$ alkylcarbonyl. Each $R^3$ may independently be $C_1$-$C_4$ alkylcarbonyl. Each $R^3$ may independently be $C_1$-$C_3$ alkylcarbonyl. Each $R^3$ may independently be $C_1$-$C_2$ alkylcarbonyl. Each $R^3$ may independently be methylcarbonyl. Each $R^3$ may independently be $C_2$ alkylcarbonyl. Each $R^3$ may independently be $C_3$ alkylcarbonyl. Each $R^3$ may independently be $C_4$ alkylcarbonyl. Each $R^3$ may independently be $C_5$ alkylcarbonyl.

In other embodiments, Each $R^4$ may independently be $C_1$-$C_5$ alkylcarbonyl. Each $R^4$ may independently be $C_1$-$C_4$ alkylcarbonyl. Each $R^4$ may independently be $C_1$-$C_3$ alkylcarbonyl. Each $R^4$ may independently be $C_1$-$C_2$ alkylcarbonyl. Each $R^4$ may independently be methylcarbonyl. Each $R^4$ may independently be $C_2$ alkylcarbonyl. Each $R^4$ may independently be $C_3$ alkylcarbonyl. Each $R^4$ may independently be $C_4$ alkylcarbonyl. Each $R^4$ may independently be $C_5$ alkylcarbonyl.

In other embodiments, Each $R^5$ may independently be $C_1$-$C_5$ alkylcarbonyl. Each $R^5$ may independently be $C_1$-$C_4$ alkylcarbonyl. Each $R^5$ may independently be $C_1$-$C_3$ alkylcarbonyl. Each $R^5$ may independently be $C_1$-$C_2$ alkylcarbonyl. Each $R^5$ may independently be methylcarbonyl. Each $R^5$ may independently be $C_2$ alkylcarbonyl. Each $R^5$ may independently be $C_3$ alkylcarbonyl. Each $R^5$ may independently be $C_4$ alkylcarbonyl. Each $R^5$ may independently be $C_5$ alkylcarbonyl.

In some more specific embodiments of the compound of structure (I), the compound has one of the following structures from Table 1, or a pharmaceutically acceptable salt thereof:

TABLE 1

Representative $^{123}$I Compounds

| No. | Structure | Name |
| --- | --- | --- |
| 1 | 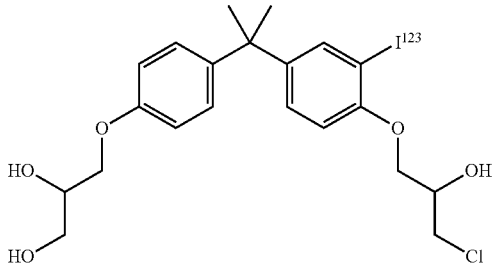 | 3-(4-(2-(4-(3-chloro-2-hydroxypropoxy)-3-$^{123}$iodophenyl)propan-2-yl)phenoxy)propane-1,2-diol |
| 1a | 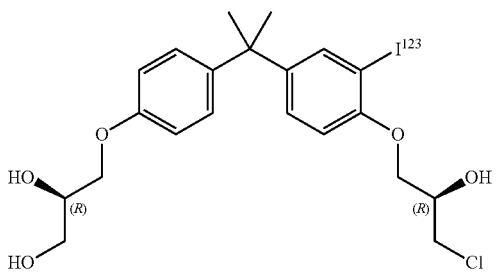 | (R)-3-(4-(2-(4-((R)-3-chloro-2-hydroxypropoxy)-3-$^{123}$iodophenyl)propan-2-yl)phenoxy)propane-1,2-diol |

TABLE 1-continued

Representative $^{123}$I Compounds

| No. | Structure | Name |
|---|---|---|
| 1b | 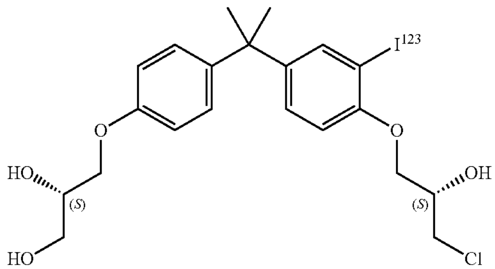 | (S)-3-(4-(2-(4-((S)-3-chloro-2-hydroxypropoxy)-3-$^{123}$iodophenyl)propan-2-yl)phenoxy)propane-1,2-diol |
| 1c | 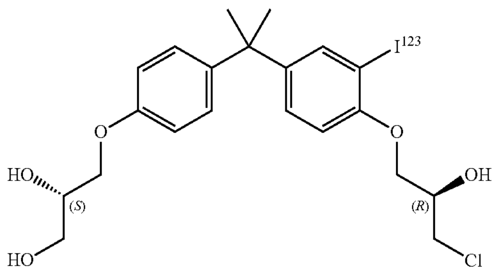 | (S)-3-(4-(2-(4-((R)-3-chloro-2-hydroxypropoxy)-3-$^{123}$iodophenyl)propan-2-yl)phenoxy)propane-1,2-diol |
| 1d | 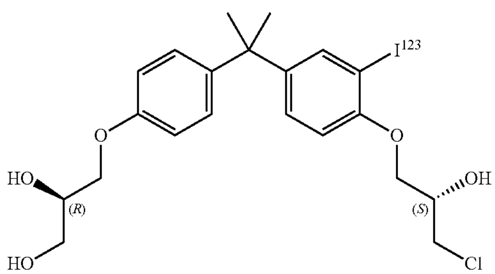 | (R)-3-(4-(2-(4-((S)-3-chloro-2-hydroxypropoxy)-3-$^{123}$iodophenyl)propan-2-yl)phenoxy)propane-1,2-diol |
| 2 | 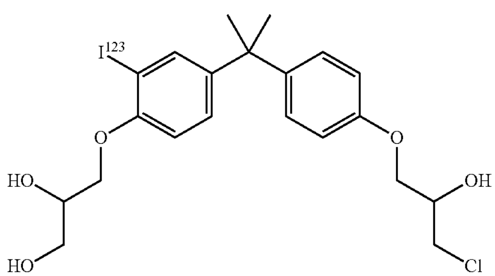 | 3-(4-(2-(4-(3-chloro-2-hydroxypropoxy)phenyl)propan-2-yl)-2-$^{123}$iodophenoxy)propane-1,2-diol |
| 2a | 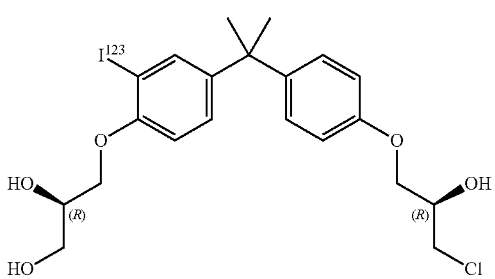 | (R)-3-(4-(2-(4-((R)-3-chloro-2-hydroxypropoxy)phenyl)propan-2-yl)-2-$^{123}$iodophenoxy)propane-1,2-diol |

TABLE 1-continued

Representative $^{123}$I Compounds

| No. | Structure | Name |
| --- | --- | --- |
| 2b | 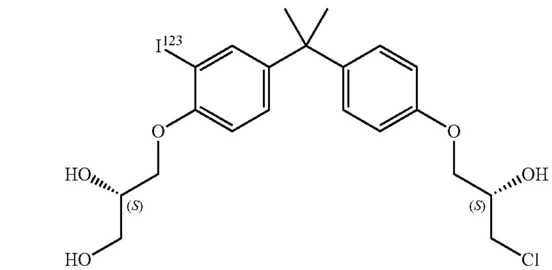 | (S)-3-(4-(2-(4-((S)-3-chloro-2-hydroxypropoxy)phenyl)propan-2-yl)-2-$^{123}$iodophenoxy)propane-1,2-diol |
| 2c | 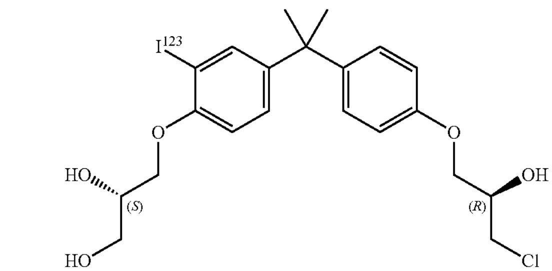 | (S)-3-(4-(2-(4-((R)-3-chloro-2-hydroxypropoxy)phenyl)propan-2-yl)-2-$^{123}$iodophenoxy)propane-1,2-diol |
| 2d | 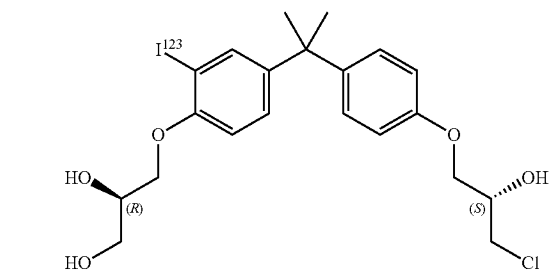 | (R)-3-(4-(2-(4-((S)-3-chloro-2-hydroxypropoxy)phenyl)propan-2-yl)-2-$^{123}$iodophenoxy)propane-1,2-diol |
| 3 | 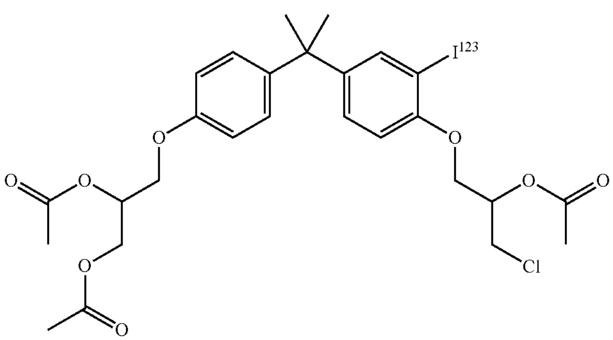 | 3-(4-(2-(4-(2-acetoxy-3-chloropropoxy)-3-$^{123}$iodophenyl)propan-2-yl)phenoxy)propane-1,2-diyl diacetate |
| 3a | 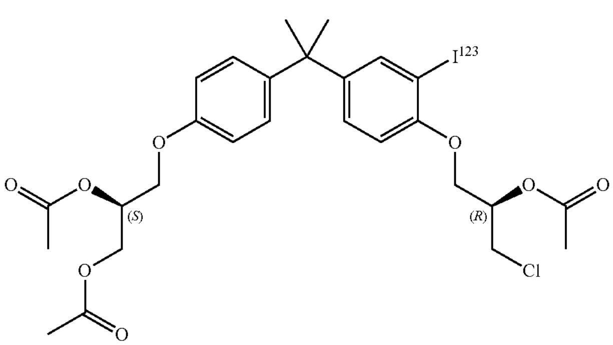 | (S)-3-(4-(2-(4-((R)-2-acetoxy-3-chloropropoxy)-3-$^{123}$iodophenyl)propan-2-yl)phenoxy)propane-1,2-diyl diacetate |

TABLE 1-continued

Representative $^{123}$I Compounds

| No. | Structure | Name |
|---|---|---|
| 3b | 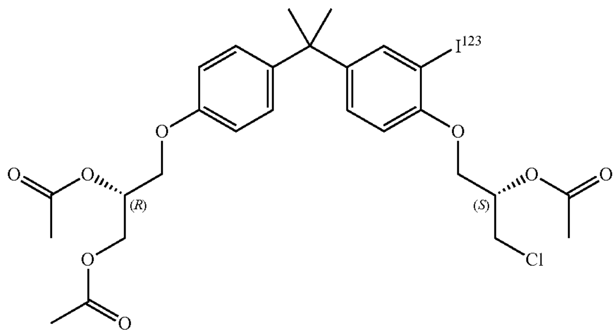 | (R)-3-(4-(2-(4-((S)-2-acetoxy-3-chloropropoxy)-3-$^{123}$iodophenyl)propan-2-yl)phenoxy)propane-1,2-diyl diacetate |
| 3c | 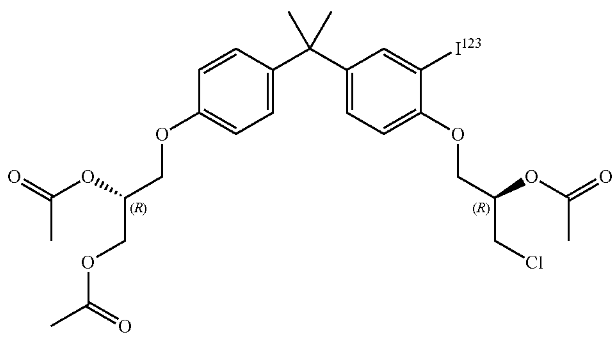 | (R)-3-(4-(2-(4-((R)-2-acetoxy-3-chloropropoxy)-3-$^{123}$iodophenyl)propan-2-yl)phenoxy)propane-1,2-diyl diacetate |
| 3d | 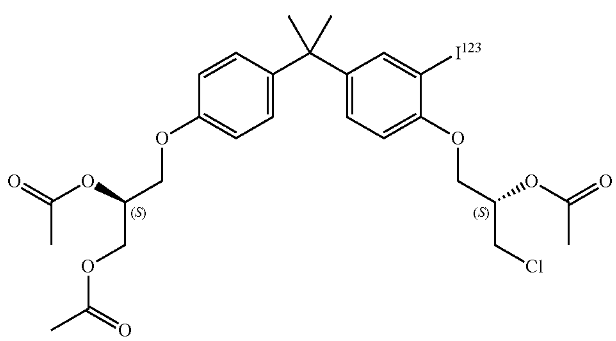 | (S)-3-(4-(2-(4-((S)-2-acetoxy-3-chloropropoxy)-3-$^{123}$iodophenyl)propan-2-yl)phenoxy)propane-1,2-diyl diacetate |
| 4 | 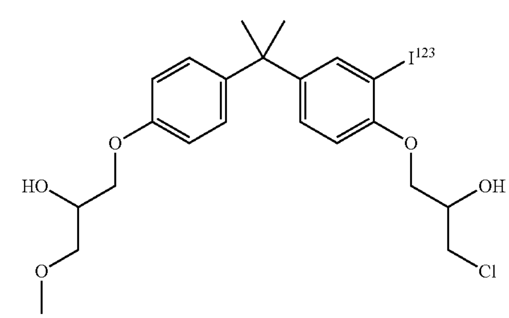 | 1-chloro-3-(4-(2-(4-(2-hydroxy-3-methoxypropoxy)phenyl)propan-2-yl)-2-$^{123}$iodophenoxy)propan-2-ol |

TABLE 1-continued

Representative $^{123}$I Compounds

| No. | Structure | Name |
|---|---|---|
| 4a | 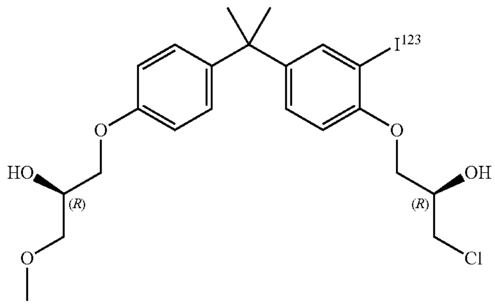 | (R)-1-chloro-3-(4-(2-(4-((R)-2-hydroxy-3-methoxypropoxy)phenyl)propan-2-yl)-2-$^{123}$iodophenoxy)propan-2-ol |
| 4b | 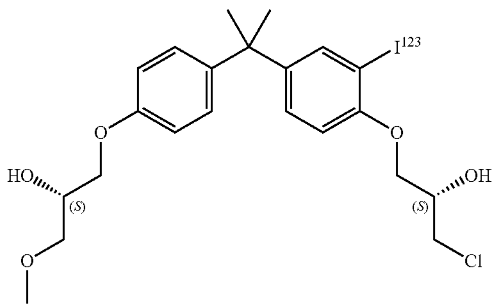 | (S)-1-chloro-3-(4-(2-(4-((S)-2-hydroxy-3-methoxypropoxy)phenyl)propan-2-yl)-2-$^{123}$iodophenoxy)propan-2-ol |
| 4c | 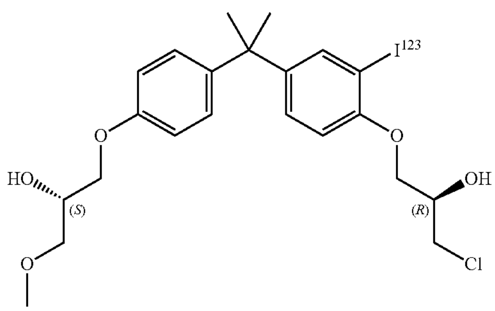 | (R)-1-chloro-3-(4-(2-(4-((S)-2-hydroxy-3-methoxypropoxy)phenyl)propan-2-yl)-2-$^{123}$iodophenoxy)propan-2-ol |
| 4d | 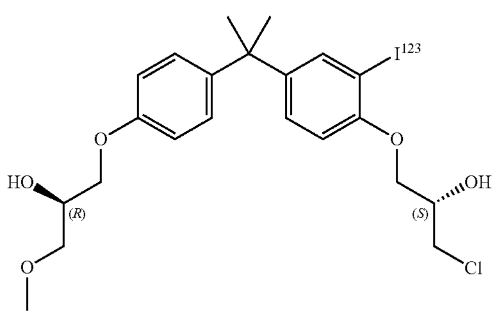 | (S)-1-chloro-3-(4-(2-(4-((R)-2-hydroxy-3-methoxypropoxy)phenyl)propan-2-yl)-2-$^{123}$iodophenoxy)propan-2-ol |
| 5 | 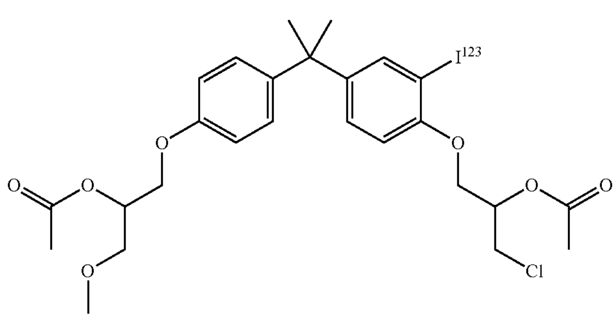 | 1-(4-(2-(4-(2-acetoxy-3-chloropropoxy)-3-$^{123}$iodophenyl)propan-2-yl)phenoxy)-3-methoxypropan-2-yl acetate |

TABLE 1-continued

Representative $^{123}$I Compounds

| No. | Structure | Name |
|---|---|---|
| 5a | 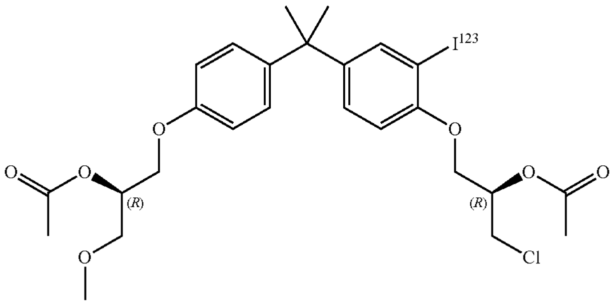 | (R)-1-(4-(2-(4-((R)-2-acetoxy-3-chloropropoxy)-3-$^{123}$iodophenyl)propan-2-yl)phenoxy)-3-methoxypropan-2-yl acetate |
| 5b | 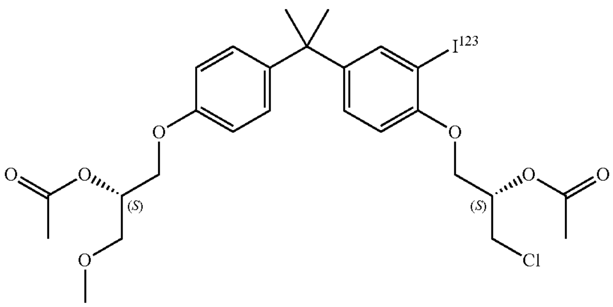 | (S)-1-(4-(2-(4-((S)-2-acetoxy-3-chloropropoxy)-3-$^{123}$iodophenyl)propan-2-yl)phenoxy)-3-methoxypropan-2-yl acetate |
| 5c | 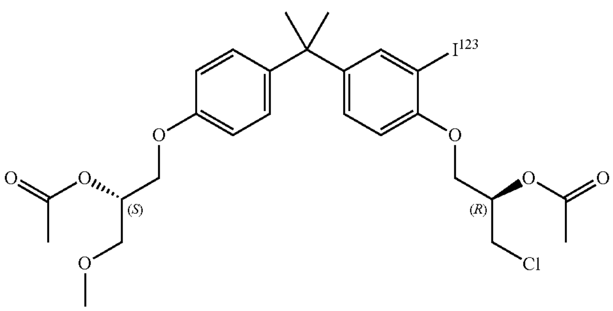 | (S)-1-(4-(2-(4-((R)-2-acetoxy-3-chloropropoxy)-3-$^{123}$iodophenyl)propan-2-yl)phenoxy)-3-methoxypropan-2-yl acetate |
| 5d | 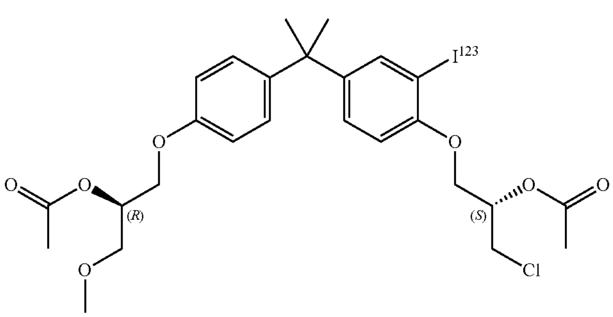 | (R)-1-(4-(2-(4-((S)-2-acetoxy-3-chloropropoxy)-3-$^{123}$iodophenyl)propan-2-yl)phenoxy)-3-methoxypropan-2-yl acetate |

TABLE 1-continued

Representative $^{123}$I Compounds

| No. | Structure | Name |
|---|---|---|
| 6 | 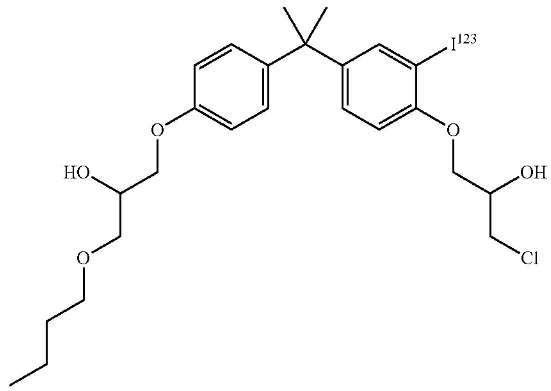 | 1-butoxy-3-(4-(2-(4-(3-chloro-2-hydroxypropoxy)-3-$^{123}$iodophenyl)propan-2-yl)phenoxy)propan-2-ol |
| 6a | 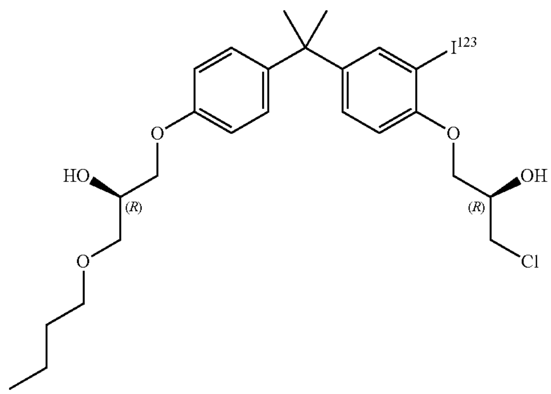 | (R)-1-butoxy-3-(4-(2-(4-((R)-3-chloro-2-hydroxypropoxy)-3-$^{123}$iodophenyl)propan-2-yl)phenoxy)propan-2-ol |
| 6b | 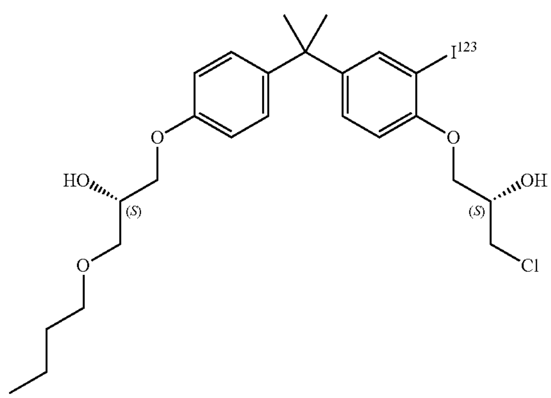 | (S)-1-butoxy-3-(4-(2-(4-((S)-3-chloro-2-hydroxypropoxy)-3-$^{123}$iodophenyl)propan-2-yl)phenoxy)propan-2-ol |
| 6c | 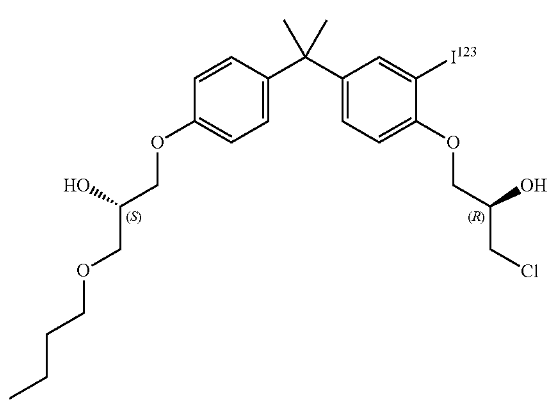 | (S)-1-butoxy-3-(4-(2-(4-((R)-3-chloro-2-hydroxypropoxy)-3-$^{123}$iodophenyl)propan-2-yl)phenoxy)propan-2-ol |

TABLE 1-continued

Representative $^{123}$I Compounds

| No. | Structure | Name |
|---|---|---|
| 6d | 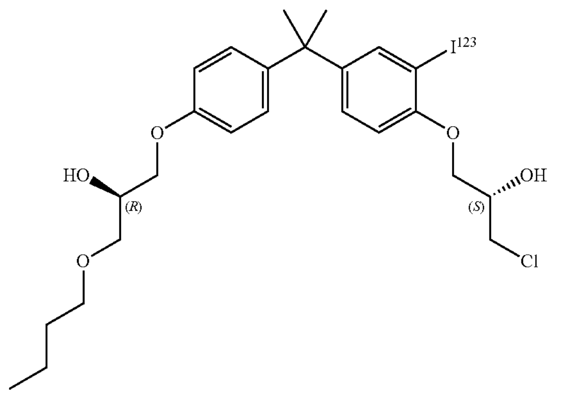 | (R)-1-butoxy-3-(4-(2-(4-((S)-3-chloro-2-hydroxypropoxy)-3-$^{123}$iodophenyl)propan-2-yl)phenoxy)propan-2-ol |
| 7 | 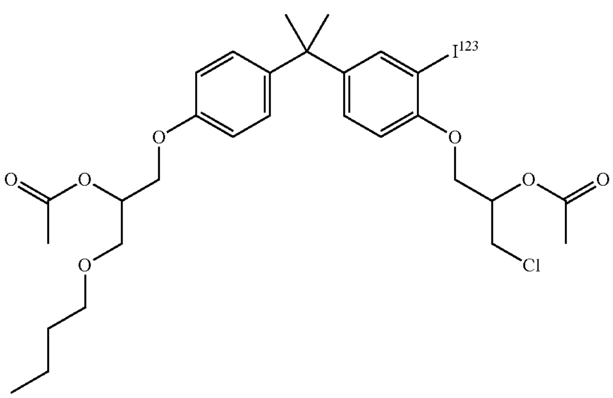 | 1-(4-(2-(4-(2-acetoxy-3-butoxypropoxy)phenyl)propan-2-yl)-2-$^{123}$iodophenoxy)-3-chloropropan-2-yl acetate |
| 7a | 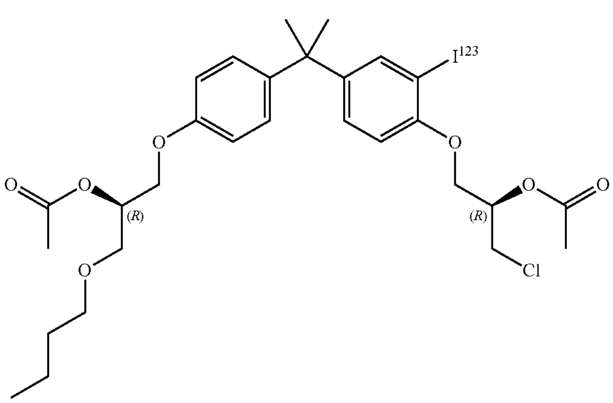 | (R)-1-(4-(2-(4-((R)-2-acetoxy-3-butoxypropoxy)phenyl)propan-2-yl)-2-$^{123}$iodophenoxy)-3-chloropropan-2-yl acetate |

TABLE 1-continued

Representative $^{123}$I Compounds

| No. | Structure | Name |
|---|---|---|
| 7b | 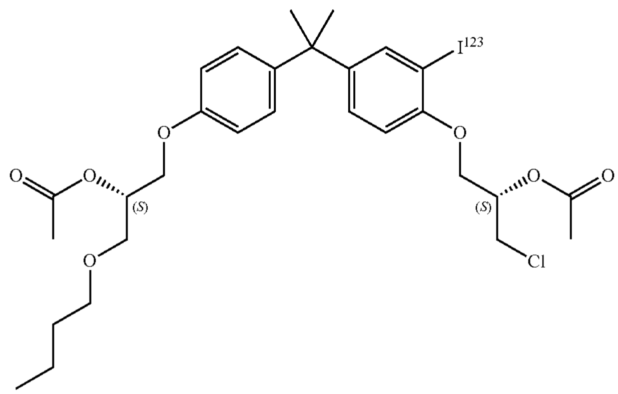 | (S)-1-(4-(2-(4-((S)-2-acetoxy-3-butoxypropoxy)phenyl)propan-2-yl)-2-$^{123}$iodophenoxy)-3-chloropropan-2-yl acetate |
| 7c | 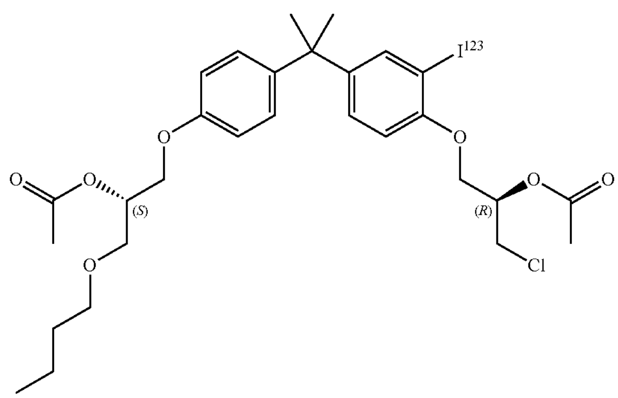 | (R)-1-(4-(2-(4-((S)-2-acetoxy-3-butoxypropoxy)phenyl)propan-2-yl)-2-$^{123}$iodophenoxy)-3-chloropropan-2-yl acetate |
| 7d | 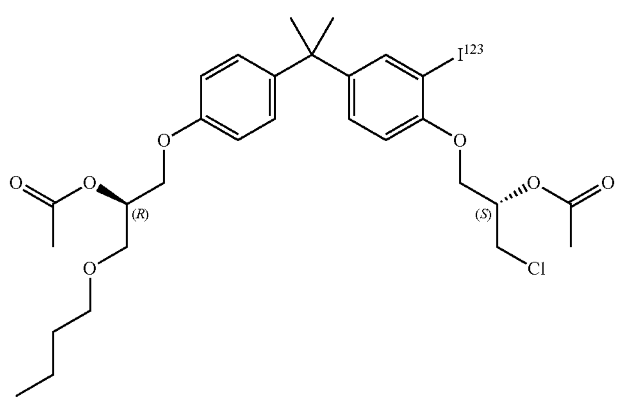 | (S)-1-(4-(2-(4-((R)-2-acetoxy-3-butoxypropoxy)phenyl)propan-2-yl)-2-$^{123}$iodophenoxy)-3-chloropropan-2-yl acetate |
| 8 | 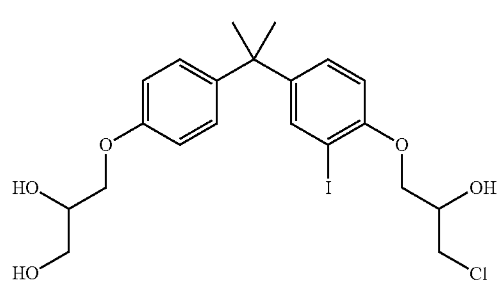 [SMILES: CC(C)(c1ccc(OCC(O)CO)cc1)c1ccc(OCC(O)CCl)c(I)c1] | 3-(4-(2-(4-(3-chloro-2-hydroxypropoxy)-3-iodophenyl)propan-2-yl)phenoxy)propane-1,2-diol |

TABLE 1-continued

Representative $^{123}$I Compounds

| No. | Structure | Name |
|---|---|---|
| 8a | 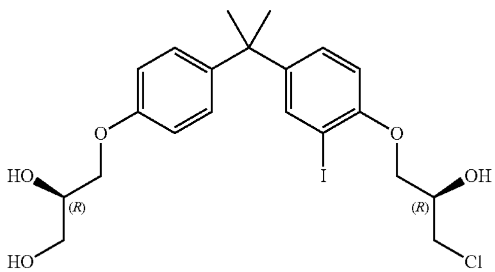 | (R)-3-(4-(2-(4-((R)-3-chloro-2-hydroxypropoxy)-3-iodophenyl)propan-2-yl)phenoxy)propane-1,2-diol |
| 8b | 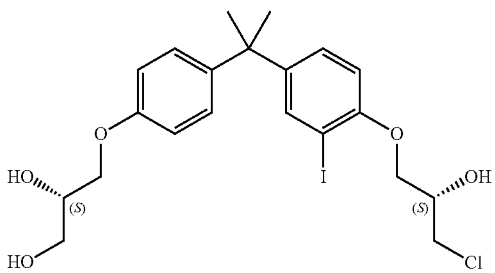 | (S)-3-(4-(2-(4-((S)-3-chloro-2-hydroxypropoxy)-3-iodophenyl)propan-2-yl)phenoxy)propane-1,2-diol |
| 8c | 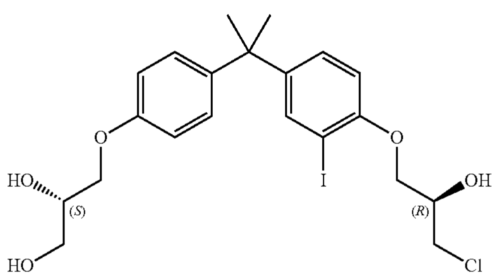 | (S)-3-(4-(2-(4-((R)-3-chloro-2-hydroxypropoxy)-3-iodophenyl)propan-2-yl)phenoxy)propane-1,2-diol |
| 8d | 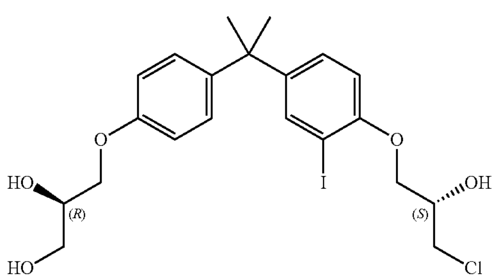 | (R)-3-(4-(2-(4-((S)-3-chloro-2-hydroxypropoxy)-3-iodophenyl)propan-2-yl)phenoxy)propane-1,2-diol |
| 9 | 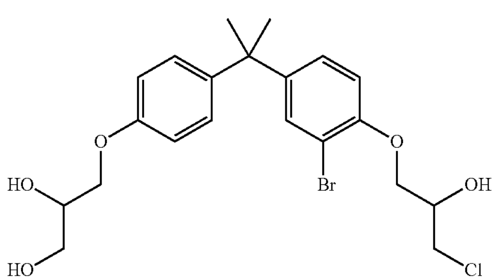 [SMILES: CC(C)(c1ccc(OCC(O)CO)cc1)c1ccc(OCC(O)CCl)c(Br)c1] | 3-(4-(2-(3-bromo-4-(3-chloro-2-hydroxypropoxy)phenyl)propan-2-yl)phenoxy)propane-1,2-diol |

TABLE 1-continued

Representative ¹²³I Compounds

| No. | Structure | Name |
|---|---|---|
| 9a | 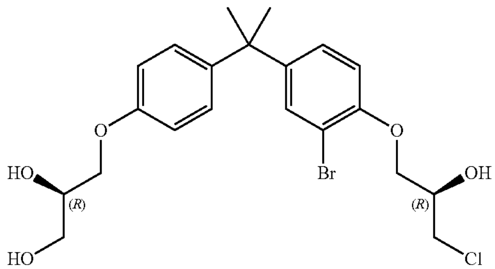 | (R)-3-(4-(2-(3-bromo-4-((R)-3-chloro-2-hydroxypropoxy)phenyl)propan-2-yl)phenoxy)propane-1,2-diol |
| 9b | 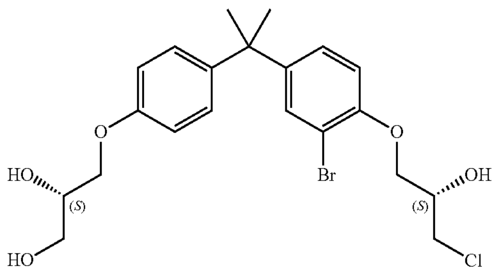 | (S)-3-(4-(2-(3-bromo-4-((S)-3-chloro-2-hydroxypropoxy)phenyl)propan-2-yl)phenoxy)propane-1,2-diol |
| 9c | 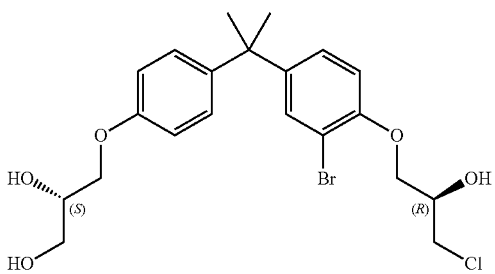 | (S)-3-(4-(2-(3-bromo-4-((R)-3-chloro-2-hydroxypropoxy)phenyl)propan-2-yl)phenoxy)propane-1,2-diol |
| 9d | 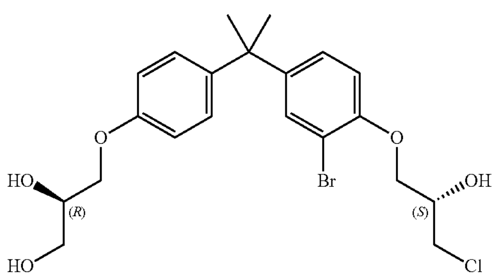 | (R)-3-(4-(2-(3-bromo-4-((S)-3-chloro-2-hydroxypropoxy)phenyl)propan-2-yl)phenoxy)propane-1,2-diol |
| 10 | 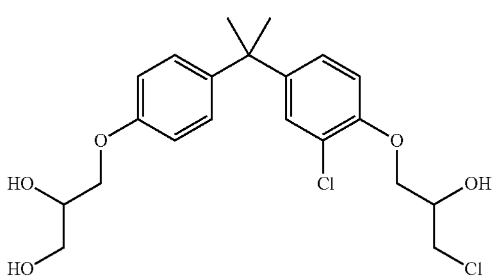 [SMILES: CC(C)(c1ccc(OCC(O)CO)cc1)c1ccc(OCC(O)CCl)c(Cl)c1] | 3-(4-(2-(3-chloro-4-(3-chloro-2-hydroxypropoxy)phenyl)propan-2-yl)phenoxy)propane-1,2-diol |

TABLE 1-continued

Representative $^{123}$I Compounds

| No. | Structure | Name |
|---|---|---|
| 10a | 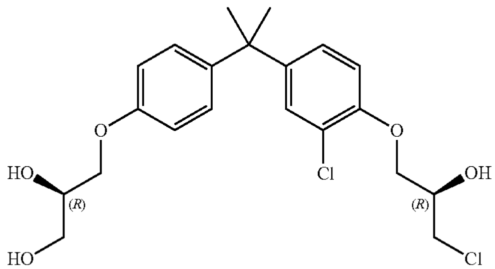 | (R)-3-(4-(2-(3-chloro-4-((R)-3-chloro-2-hydroxypropoxy)phenyl)propan-2-yl)phenoxy)propane-1,2-diol |
| 10b | 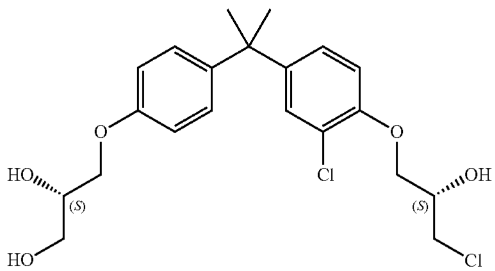 | (S)-3-(4-(2-(3-chloro-4-((S)-3-chloro-2-hydroxypropoxy)phenyl)propan-2-yl)phenoxy)propane-1,2-diol |
| 10c | 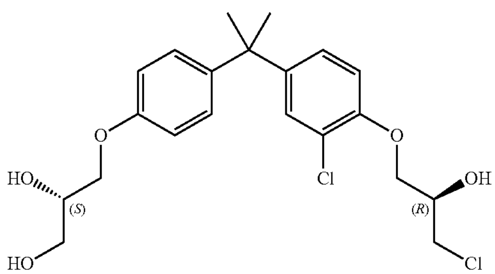 | (S)-3-(4-(2-(3-chloro-4-((R)-3-chloro-2-hydroxypropoxy)phenyl)propan-2-yl)phenoxy)propane-1,2-diol |
| 10d | 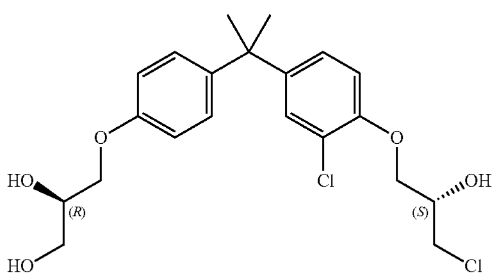 | (R)-3-(4-(2-(3-chloro-4-((S)-3-chloro-2-hydroxypropoxy)phenyl)propan-2-yl)phenoxy)propane-1,2-diol |
| 11 | 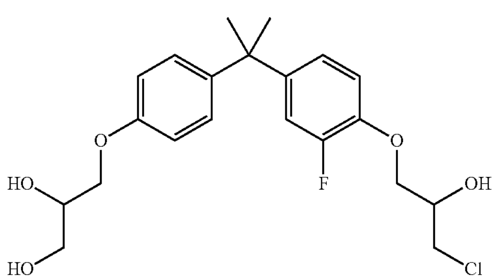 | 3-(4-(2-(4-(3-chloro-2-hydroxypropoxy)-3-fluorophenyl)propan-2-yl)phenoxy)propane-1,2-diol |

TABLE 1-continued

Representative $^{123}$I Compounds

| No. | Structure | Name |
|---|---|---|
| 11a | 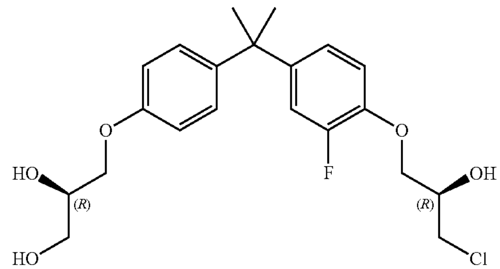 | (R)-3-(4-(2-(4-((R)-3-chloro-2-hydroxypropoxy)-3-fluorophenyl)propan-2-yl)phenoxy)propane-1,2-diol |
| 11b | 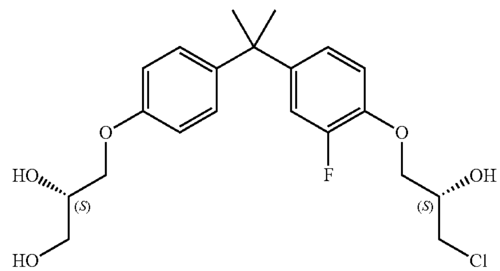 | (S)-3-(4-(2-(4-((S)-3-chloro-2-hydroxypropoxy)-3-fluorophenyl)propan-2-yl)phenoxy)propane-1,2-diol |
| 11c | 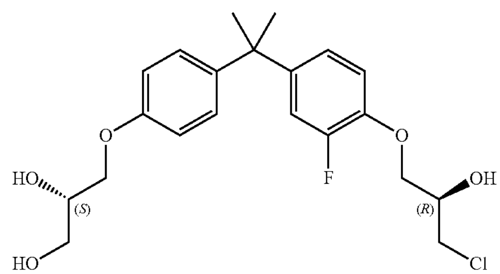 | (S)-3-(4-(2-(4-((R)-3-chloro-2-hydroxypropoxy)-3-fluorophenyl)propan-2-yl)phenoxy)propane-1,2-diol |
| 11d | 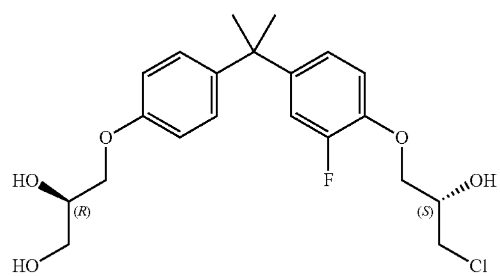 | (R)-3-(4-(2-(4-((S)-3-chloro-2-hydroxypropoxy)-3-fluorophenyl)propan-2-yl)phenoxy)propane-1,2-diol |

In some embodiments, compounds of structure I which result in unstable structures and/or unsatisfied valences are not included within the scope of the invention.

In another embodiment, the present disclosure provides a pharmaceutical composition comprising any of the foregoing compounds of structure (I) and a pharmaceutically acceptable carrier.

Compounds as described herein may be in the free form or in the form of a salt thereof. In some embodiments, compounds as described herein may be in the form of a pharmaceutically acceptable salt, which are known in the art (Berge et al., *J. Pharm. Sci.* 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-naphalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, pharmaceutical compositions in accordance with this invention may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition according to the invention includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to lethal CRPC. Typically, a prophylactic dose is used in subjects prior to or at an earlier stage of disease, so that a prophylactically effective amount may be less than a therapeutically effective amount.

It is to be noted that dosage values may vary with the exact imaging protocol. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum imaging result. For example, a single bolus may be administered, several divided doses may be administered over time or the dose may be proportionally reduced or increased as indicated by the imaging results. It may be advantageous to formulate parenteral compositions in dosage unit form for ease of administration and uniformity of dosage.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances, such as in severe disease conditions, substantial excesses of the compositions may be administered for therapeutic effects. Some compounds of this invention may be toxic at some concentrations. Titration studies may be used to determine toxic and non-toxic concentrations. Toxicity may be evaluated by examining a particular compound's or composition's specificity across cell lines using PC3 or DU145 cells as possible negative controls since these cells do not express functional AR. Animal studies may be used to provide an indication if the compound has any effects on other tissues. Systemic therapy that targets the AR will not likely cause major problems to other tissues since antiandrogens and androgen insensitivity syndrome are not fatal.

Compounds as described herein may be administered to a subject. As used herein, a "subject" may be a human, non-human primate, mammal, rat, mouse, cow, horse, pig, sheep, goat, dog, cat and the like. The subject may be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

Compounds for use in the present invention may be obtained from medical sources or modified using known methodologies from naturally occurring compounds. In addition, methods of preparing or synthesizing compounds of the present invention will be understood by a person of skill in the art having reference to known chemical synthesis principles. For example, Auzou et al 1974 *European Journal of Medicinal Chemistry* 9(5), 548-554 describes suitable synthetic procedures that may be considered and suitably adapted for preparing compounds of any one of the compounds of structure (I) as set out above. Other references that may be helpful include: Debasish Das, Jyh-Fu Lee and Soofin Cheng "Sulfonic acid functionalized mesoporous MCM-41 silica as a convenient catalyst for Bisphenol-A synthesis" Chemical Communications, (2001) 2178-2179; U.S. Pat. No. 2,571,217 Davis, Orris L.; Knight, Horace S.; Skinner, John R. (Shell Development Co.) "Halohydrin ethers of phenols." (1951); and Rokicki, G.; Pawlicki, J.; Kuran, W. "Reactions of 4-chloromethyl-1,3-dioxolan-2-one with phenols as a new route to polyols and cyclic carbonates." Journal fuer Praktische Chemie (Leipzig) (1985) 327, 718-722.

For example, exemplary compounds of the present invention may be prepared with reference to the following General Reaction Scheme I, wherein $R^1$ and $R^2$ are as described above and $L^1$ and $L^2$ are independently a leacing group:

General Reaction Scheme I

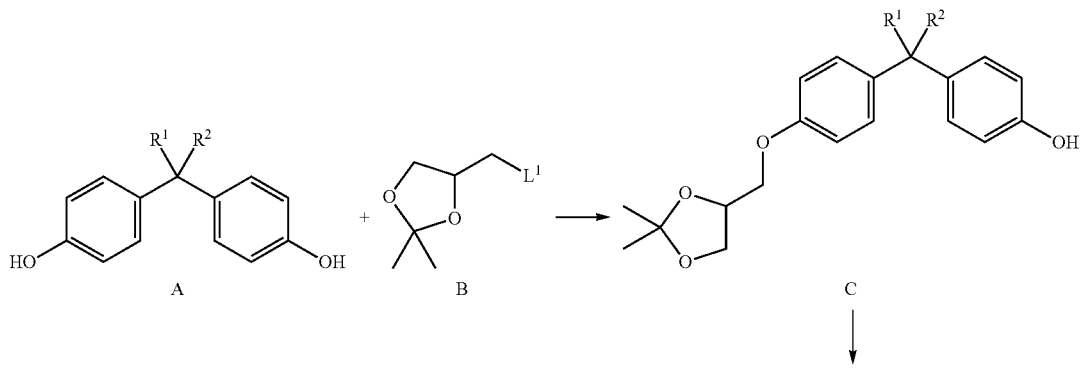

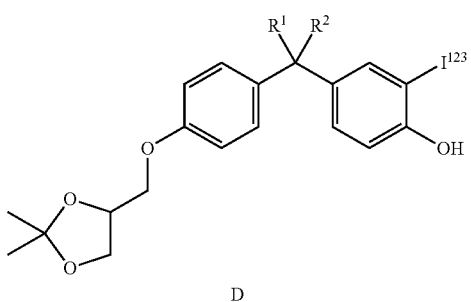
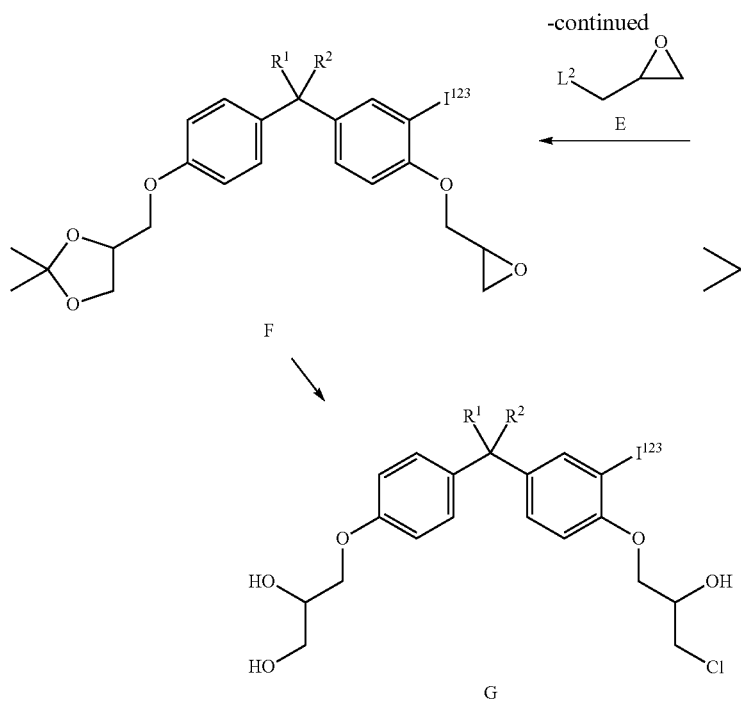

Referring to General Reaction Scheme I, bisphenol compounds of structure A can be purchased from commercial sources or prepared according to methods well-known to those of ordinary skill in the art. Compounds of structure A can be reacted with compounds of structure B under basic conditions (e.g., NaH) to yield compounds of structure C. In this regard, particularily useful leaving groups ($L^1$) include p-toulenesulfonates ("tosyl"), which can be prepared by reaction of the corresponding alcohol with tosyl chloride. Further, various stereoisomers of compound B can be used depending on the desired stereochemistry of the final product. Various stereoisomer of B can be purchased or prepared according to methods known in the art. The radioactive iodine moiety ($^{123}I$) can be installed by reaction of C with an appropriate iodinating reagent, for example $Na^{123}I$ and a suitable oxidant (e.g., NaClO) to yield D. It should be noted that, although General Reaction Scheme I depicts iodination at only one position, other compounds of structure (I) with $^{123}I$ at different positions and/or multiple $^{123}I$ substitutions can be prepared according to analogous methods known to those of ordinary skill in the art.

Reaction of D with epoxide E under basic conditions (e.g., NaH) yields compounds of structure F. Again, tosyl leaving groups have been fond to be particularly useful as the $L^2$ moiety, and various stereoisomers of compound F can be used depending on the desired stereochemistry of the final product. Finally, reaction of F with an appropriate reagent, such as $CeCl3.7H_2O$ yields G. Other compounds of structure (I) wherein $R^3$, $R^4$ and/or $R^5$ are moieties other than H can be prepared by further modification of compound G. For example alkylation with common alkylating reagents (e.g., methyl idodide) and/or acylation with common acylating reagents (e.g., acetyl chloride) yields compounds of structure (I) wherein $R^3$, $R^4$ and/or $R^5$ are $C_1$-$C_{10}$ alkyl or $C_1$-$C_{10}$ alkylcarbonyl, respectively.

One skilled in the art will recognize that variations to the order of the steps and reagents discussed in reference to the above General Synthetic Scheme I are possible. For example, epoxidation may precede dioxalone formation. Further, $^{123}I$ atoms may be introduced via any number of reagents, and iodination is not limited to those methods depicted or described above. Methods for such iodination are well known in the art. Methodologies for preparation of specific exemplary compounds of structure I are described in more detail in the following examples.

In addition, protecting group strategies may be employed for preparation of the compounds disclosed herein. Such strategies are well known to those of skill in the art. Exemplary protecting groups and related strategies are disclosed in Greene's Protective Groups in Organic Synthesis, Wiley-Interscience; 4 edition (Oct. 30, 2006), which is hereby incorporated by reference in its entirety. In certain embodiments, a protecting group is used to mask an alcohol moiety while performing other chemical transformations. After removal of the protecting group, the free hydroxyl is obtained. Such protecting groups and strategies are well known in the art.

The present compounds find particular utility in methods for imaging the prostate. In some embodiments, a method for imaging benign conditions of the prostate (e.g., benign prostatic hyperplasia), comprising administering any of the foregoing pharmaceutical compositions to a subject and detecting the prostate, is provided. Accordingly, in another embodiment, the present disclosure provides a method of imaging cancer, the method comprising administering the foregoing pharmaceutical composition to a subject and detecting the presence or absence of cancer by use of SPECT.

In certain embodiments, the method identifies the presence or absence of a tumor. For example, some embodiments the method identifies the location of a tumor. In certain embodiments, the cancer is prostate cancer, for example, castration resistant prostate cancer. In other embodiments, the prostate cancer is androgen-dependent prostate cancer. In some embodiments, the subject is a mammal such as a human.

In some other embodiments, the method is useful for detecting the presence of AR splice variants or other AR species that cannot be detected by imaging agents that interact with the AR LBD (i.e., mutations, truncations). Without wishing to be bound by any particular theory, since the present compounds bind to the AR N-terminal domain (NTD), even mutants or variants which lack the AR LBD can be imaged employing the present compounds. Thus, the present methods may be useful for detecting AR species, including mutants and variants, which lack the LBD or have LBD mutations, but do comprise the AR NTD. In other embodiments the method detects the presence or overexpression of AR splice variants lacking the ligand binding domain. For example, the method may include sequential imaging with $^{18}$F-FDHT and a compound of the invention and a discordant distribution or discordant level of uptake between $^{18}$F-FDHT and the compound of the invention indicates the presence or overexpression of splice variants lacking the ligan binding domain.

In other embodiments, the compounds of the invention are used in single photon emission computed tomography methods to monitor a patient's response to therapy. In other embodiments, the methods comprise use of a compound of the invention to detect the AR NTD.

In another embodiment, the present disclosure provides the use of any one of the foregoing compounds of Formula (I) for imaging cancer. For example in some embodiments, the imaging is in a human patient.

In another embodiment, the present disclosure provides the use of any one of the foregoing compounds of Formula (I) for imaging the prostate. For example in some embodiments, the imaging is in a human patient.

In accordance with another embodiment, there is provided a use of the compounds of Formula (I) as described anywhere herein for preparation of a medicament for imaging the prostate. The imaging may be for imaging of benign postate conditions of for imaging cancer (e.g., tumors), for example prostate cancer. The imaging may be by SPECT.

The imaging may be in a mammalian cell. The imaging may be in a mammal. The mammal may be a human.

Alternatively, the compounds may be administered to a mammal for imaging purposes. The administering and imaging may be to a mammal in need of diagnosis of at least one indication selected from the group consisting of: prostate cancer, breast cancer, ovarian cancer, endometrial cancer, salivary gland carcinoma, benign prostatic hyperplasia, hair loss, acne, hirsutism, ovarian cysts, polycystic ovary disease, precocious puberty, spinal and bulbar muscular atrophy (e.g., Kennedy's disease), and age-related macular degeneration. The mammalian cell may be a human cell. The imaging may be for imaging AR splice variants, mutants or other AR species which comprise the AR NTD.

In some embodiments, the compounds as described herein or pharmaceutically acceptable salts thereof may be used for imaging and diagnosis of at least one indication selected from the group consisting of: prostate cancer, breast cancer, ovarian cancer, endometrial cancer, salivary gland carcinoma, benign prostatic hyperplasia, hair loss, acne, hirsutism, ovarian cysts, polycystic ovary disease, precocious puberty, spinal and bulbar muscular atrophy, and age-related macular degeneration. In some embodiments, the compounds as described herein or acceptable salts thereof above may be used in the preparation of a medicament or a composition for imaging the prostate, for example for imaging benign prostate conditions or for imaging prostate cancer in a subject in need of such imaging (for example for diagnosis and/or location of prostate tumors).

Some aspects of this invention, make use of compositions comprising a compound described herein and a pharmaceutically acceptable excipients or carrier. In some embodiments, the prostate cancer is castration-resistant prostate cancer (also referred to as hormone refractory, androgen-independent, androgen deprivation resistant, androgen ablation resistant, androgen depletion-independent, castration-recurrent, anti-androgen-recurrent). In some embodiments the prostate cancer is androgen-dependent or androgen-sensitive. In other embodiments, the imaging is for imaging a benign prostate conditions such as benign prostatic hyperplasia. Methods of imaging any of the indications described herein are also provided. Such methods may include administering a compound as described herein or a composition of a compound as described herein, or an effective amount of a compound as described herein or composition of a compound as described herein to a subject in need thereof.

In other embodiments, the present disclosure provides a method for modulating androgen receptor (AR) activity, the method comprising administering to a mammalian cell one or more of the present compounds. In some embodiments the modulating of androgen receptor (AR) activity is in a mammalian cell.

In certain embodiments, the method for modulating androgen receptor (AR) activity is for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age related macular degeneration. In ceretain embodiments, the indication is prostate cancer. In certain embodiments, the prostate cancer is castration resistant prostate cancer. In other embodiments, the prostate cancer is androgen dependent prostate cancer. In certain embodiments, the spinal and bulbar muscular atrophy is Kennedy's disease.

In another aspect, the present disclosure provides a method of modulating androgen receptor (AR) activity, the method comprising administering a pharmaceutical composition comprising a compound as described herein to a subject in need thereof.

In another aspect, the present disclosure provides a pharmaceutical composition comprising a compound as described herein, and an additional therapeutic agent and a pharmaceutically acceptable carrier. In some embodiments, the additional therapeutic agent is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy or age related macular degeneration. In other embodiments, the additional therapeutic agent is enzalutamide, galeterone, ARN-509, ODN-201 abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX 427, OGX 011, finasteride, dutasteride, turosteride, bexlosteride, izonsteride, FCE 28260, SKF105,111 or related compounds thereof.

In an exemplary embodiment for imaging the prostate, a dose of the disclosed compounds in solution (typically 5 to 10 millicuries or 200 to 400 MBq) is typically injected rapidly into a saline drip running into a vein, in a patient. Then, the patient is placed in the SPECT for a series of one or more scans which may take from 20 minutes to as long as an hour (often, only about one quarter of the body length may be imaged at a time). Methods for SPECT scanning are well known in the art.

EXAMPLES

All non-aqueous reactions were performed in flame-dried round bottomed flasks. The flasks were fitted with rubber septa and reactions were conducted under a positive pressure of argon unless otherwise specified. Stainless steel syringes were used to transfer air- and moisture-sensitive liquids. Flash column chromatography was performed as described by Still et al. (Still, W. C.; Kahn, M.; Mitra, A. *J. Org. Chem.* 1978, 43, 2923) using 230-400 mesh silica gel. Thin-layer chromatography was performed using aluminum plates pre-coated with 0.25 mm 230-400 mesh silica gel impregnated with a fluorescent indicator (254 nm). Thin-layer chromatography plates were visualized by exposure to ultraviolet light and a "Seebach" staining solution (700 mL water, 10.5 g Cerium (IV) sulphate tetrahydrate, 15.0 g molybdato phosphoric acid, 17.5 g sulphuric acid) followed by heating (~1 min) with a heating gun (~250° C.). Organic solutions were concentrated on Büchi R-114 rotatory evaporators at reduced pressure (15-30 torr, house vacuum) at 25-40° C.

Commercial regents and solvents were used as received. All solvents used for extraction and chromatography were HPLC grade. Normal-phase Si gel Sep Paks™ were purchased from waters, Inc. Thin-layer chromatography plates were Kieselgel 60F$_{254}$. All synthetic reagents were purchased from Sigma Aldrich and Fisher Scientific Canada.

Example 1

Synthesis of (R)-3-(4-(2-(4-((S)-3-Chloro-2-Hydroxypropoxy)-3-$^{123}$Iodophenyl)Propan-2-Yl)Phenoxy)Propane-1,2-Diol (1d)

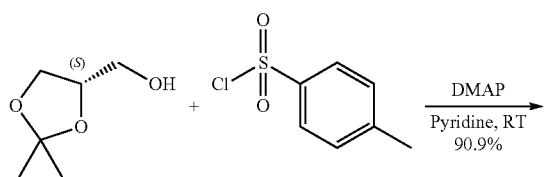

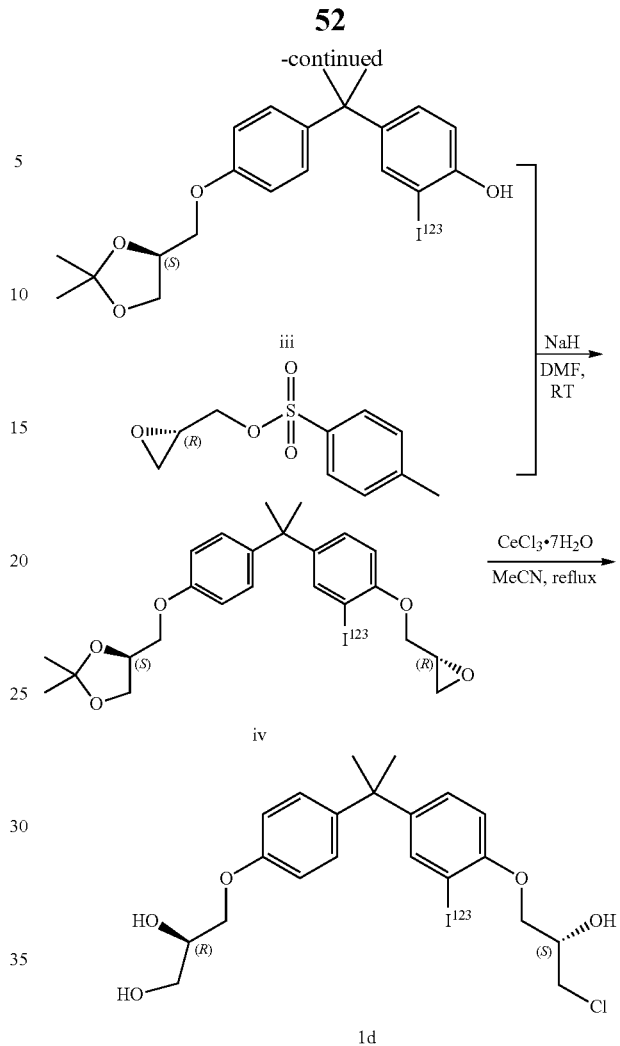

Compound i p-Toluenesulfonyl chloride (6.5 g, 34.1 mmol) was added portionwise over a period of 10 min to a solution of (S)-(+)-1,2-isopropylideneglycerol (3.0 g, 22.7 mmol) and DMAP (30 mg, 0.25 mmol) in anhydrous pyridine (30 mL) in a water bath. The resulting solution was stirred overnight. The pyridine was removed under reduced pressure, and the residue was diluted with ethyl acetate (50 mL), washed subsequently with water (2×40 mL), cold aqueous 1 M HCl (40 mL), saturated NaHCO$_3$ (40 mL) and water (40 mL). The organic layer was dried over Mg$_2$SO$_4$, filtered and concentrated to give a light yellow oil. The crude product was purified by column chromatography (eluent: 10% ethyl acetate in hexane to 30% ethyl acetate in hexane) to afford (R)-2,2-Dimethyl-1,3-dioxolane-4-methanol p-toluenesulfonate i (5.91 g, 90.9% yield) as a colorless viscous oil.

Compound ii

Sodium hydride (60% dispersion in mineral oil, 2.27 g, 56.66 mmol, 2.0 equiv) was added slowly to a stirred solution of Bisphenol A (12.94 g, 56.66 mmol, 2 equiv) in anhydrous dimethyl formamide (60 mL), at room temperature, and the contents were stirred under an atmosphere of argon for 20 min. Compound i (8.53 g, 28.33 mmol, 1.0 equiv) was added, and the mixture was allowed to react at 50-60° C. for 16 h. Next, the reaction was quenched by the addition of a saturated solution of ammonium chloride (10 mL), and the mixture was extracted with ethyl acetate (3×50 mL). The organic layer was washed with deionized water (3×40 mL), dried over anhydrous magnesium sulfate, filtered, and then concentrated under reduced pressure. The resulting residue was purified by flash column chromatography on silica gel (eluent: 5% ethyl acetate in hexane to 10% ethyl acetate in hexane) to provide the title compound (8.10 g, 83.5%) as a sticky oil.

Compound iii

Compound ii (200 mg, 0.58 mmol) was dissolved in 4 mL of methanol. One equivalent of sodium $^{123}$iodide (85 mg, 0.58 mmol) and 1.5 equiv of sodium hydroxide (35 mg, 0.88 mmol) were added and the solution was cooled to 0° C. Aqueous sodium hypochlorite (800 mg, 1 equiv, 0.58 mmol of sodium hypochlorite) was then added dropwise over 2 min at 0-3° C. The pH was kept to 6-7 by adding 10% HCl. The mixture was extracted with dichloromethane (2×20 mL). The organic layer was washed with deionized water (2×20 mL), was dried over anhydrous magnesium sulfate, was filtered, and was concentrated under reduced pressure to provide the title compound as a sticky oil.

Compound iv

Sodium hydride (60% dispersion in mineral oil, 41.6 mg, 1.04 mmol, 2.0 equiv) was added slowly to a stirred solution of compound iii in anhydrous dimethyl formamide (3 mL), at room temperature, and the contents were stirred under an atmosphere of argon for 10 min. A solution of (2R)-(−)-glycidyl tosylate 98% (142 mg, 0.62 mmol, 1.5 equiv) in anhydrous dimethyl formamide (2 mL) was added via syringe, and the mixture was allowed to react at 65-70° C. for 40 min. Next, the reaction was quenched by the addition of a saturated solution of ammonium chloride (1 mL), and the mixture was extracted with dichloromethane (2×20 mL). The organic layer was washed with deionized water (2×20 mL), dried over anhydrous magnesium sulfate, filtered and then concentrated under reduced pressure to provide a compound iv.

Compound 1d

To a solution of compound iv in acetonitrile (15 mL) was added CeCl$_3$.7H$_2$O (391 mg, 1.05 mmol, 2.5 equiv) and the mixture was refluxed for 1 h. The resulting white paste was filtered and washed with dichloromethane, and the clear suspension was concentrated under reduced pressure. The resulting residue was purified by flash column chromatography on silica gel (eluent: 25% ethyl acetate in hexane to 70% ethyl acetate in hexane) to provide compound 1d (59 mg, 19.6% total yield from compound ii) as a sticky oil.

Example 2

Synthesis of (R)-3-(4-(2-(4-((S)-3-Chloro-2-Hydroxypropoxy)-3-Iodophenyl)Propan-2-Yl)Phenoxy)Propane-1,2-Diol (8d)

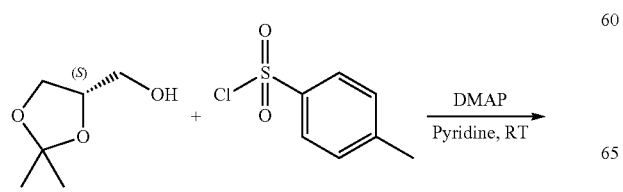

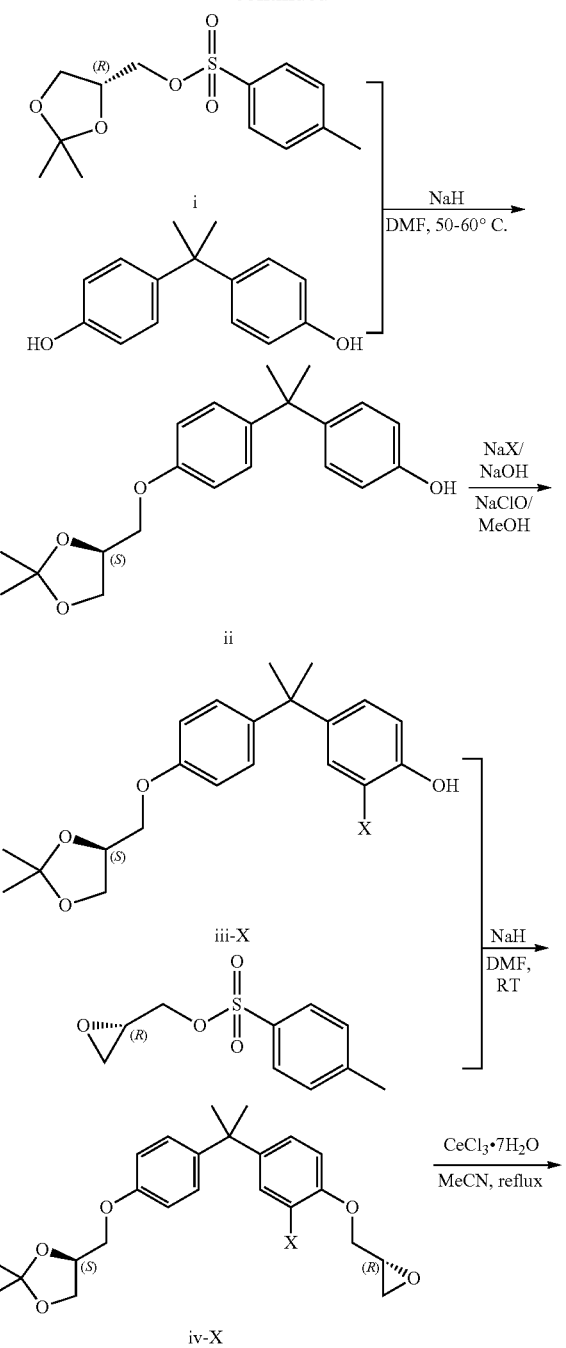

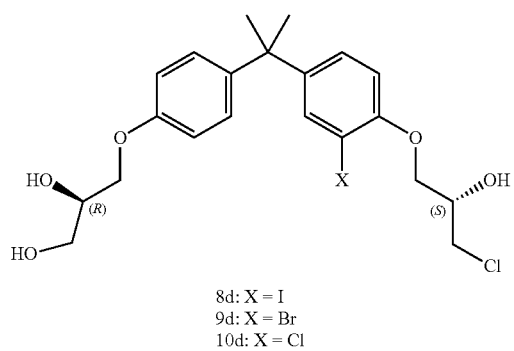

8d: X = I
9d: X = Br
10d: X = Cl

Compound iii-I

Compound ii (400 mg, 1.17 mmol, 1.0 equiv), synthesized according to Example 1, was dissolved in 8 mL of methanol. Sodium iodide (157.4 mg, 1.05 mmol, 0.9 equiv) and sodium hydroxide (70.4 mg, 1.76 mmol, 1.5 equiv) were added and the solution was cooled to 0° C. A 5.4% aqueous sodium hypochlorite (1612.9 mg, 1.17 mmol, 1 equiv) was then added dropwise over 5 min at 0-3° C. After 30 min, the pH was kept to 6-7 by adding 10% HCl. The mixture was extracted with ethyl acetate (2×30 mL). The organic layer was washed with deionized water (2×30 mL), dried over anhydrous magnesium sulfate, filtered, and concentrated under reduced pressure to provide the title compound (S)-4-(2-(4-((2,2-dimethyl-1,3-dioxolan-4-yl)methoxy)phenyl)propan-2-yl)-2-iodophenol (460 mg, 84%) as an oil.

Compound iv-I

Sodium hydride (60% dispersion in mineral oil, 12.8 mg, 0.32 mmol, 1.5 equiv) was added slowly to a stirred solution of compound iii-I (100 mg, 0.21 mmol, 1.0 equiv) in anhydrous dimethyl formamide (2 mL), at room temperature, and the contents were stirred under an atmosphere of argon for 10 min. A solution of (2R)-(−)-glycidyl tosylate 98% (73 mg, 0.32 mmol, 1.5 equiv) in anhydrous dimethyl formamide (1 mL) was added via syringe, and the mixture was allowed to react at room temperature for 16 h. Next, the reaction was quenched by the addition of a saturated solution of ammonium chloride (10 mL), and the mixture was extracted with ethyl acetate (2×20 mL). The organic layer was washed with deionized water (2×20 mL), dried over anhydrous magnesium sulfate, filtered and concentrated under reduced pressure. The resulting residue was purified by flash column chromatography on silica gel (eluent: 20% ethyl acetate in hexane to 40% ethyl acetate in hexane) to provide the title compound (S)-4-((4-(2-(3-iodo-4-(((R)-oxiran-2-yl)methoxy)phenyl)propan-2-yl)phenoxy)methyl)-2,2-dimethyl-1,3-dioxolane (106 mg, 94.6%) as a cream foam.

Compound 8d

To a solution of compound iv (130 mg, 0.25 mmol, 1.0 equiv) in acetonitrile (10 mL) was added CeCl₃·7H₂O (235 mg, 0.63 mmol, 2.5 equiv) and the mixture was refluxed for 16 h. The resulting white paste was filtered and washed with ethyl acetate, and the clear suspension was concentrated under reduced pressure. The resulting residue was purified by flash column chromatography on silica gel (eluent: 25% ethyl acetate in hexane to 70% ethyl acetate in hexane) to provide the title compound 8d (110 mg, 84.6%) as a transparent oil.

Example 3

Synthesis of (R)-3-(4-(2-(4-((S)-3-Chloro-2-Hydroxypropoxy)-3-Fluorophenyl)Propan-2-Yl)Phenoxy)Propane-1,2-Diol (11d)

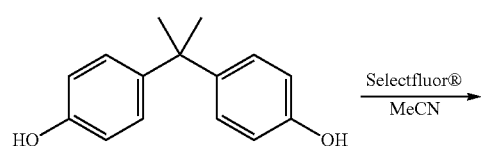

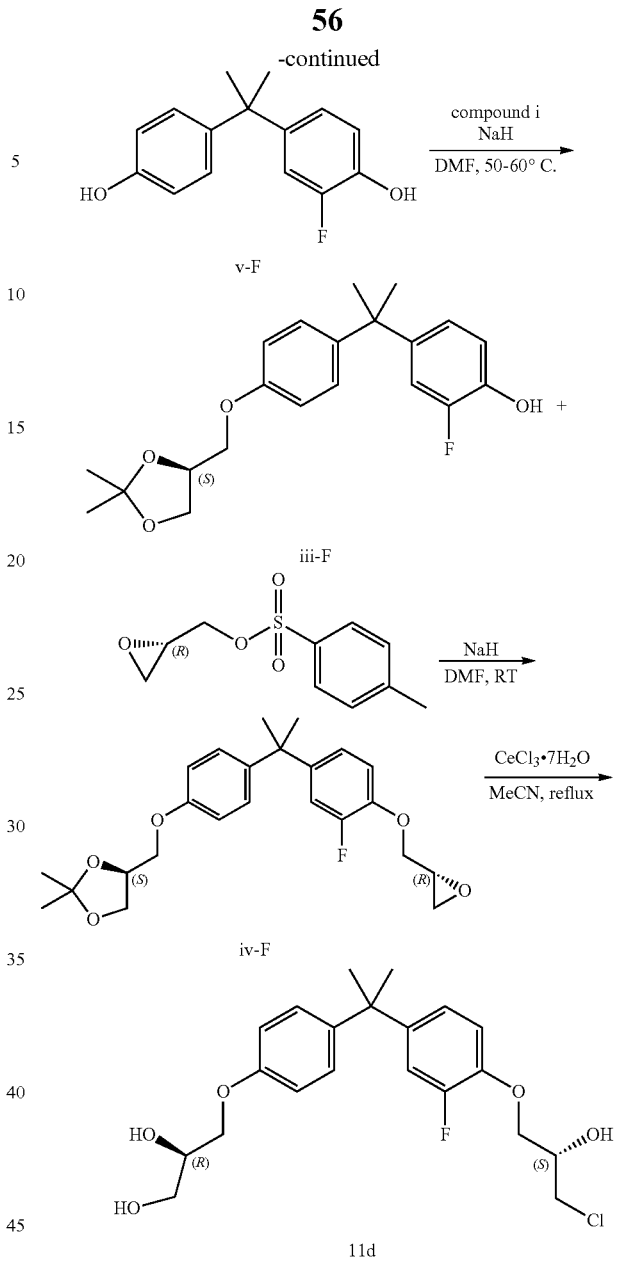

Compound v-F

Selectfluor® (736.9 mg, 2.08 mmol, 0.95 equiv) was added slowly to a stirred solution of Bisphenol A (500 mg, 2.19 mmol, 1.0 equiv) in anhydrous acetonitrile (12 mL), at room temperature, and the contents were stirred under an atmosphere of argon for 16 h. Then, the reaction was quenched by the addition of water (10 mL), and the mixture was extracted with ethyl acetate (2×20 mL). The organic layer was washed with deionized water (2×20 mL), dried over anhydrous magnesium sulfate, filtered, and concentrated under reduced pressure. The resulting residue was purified by flash column chromatography on silica gel (eluent: 1% ethyl acetate in dichloromethane to 5% ethyl acetate in dichloromethane) to provide the title compound (300 mg, 55.7%).

Compound iii-F

Sodium hydride (60% dispersion in mineral oil, 32.4 mg, 0.81 mmol, 1.0 equiv) was added slowly to a stirred solution of compound v-F (200 mg, 0.81 mmol, 1.0 equiv) in anhydrous dimethyl formamide (8 mL), at room temperature, and the contents were stirred under an atmosphere of argon for 20 min. Compound i (232 mg, 0.81 mmol, 1.0 equiv) was added, and the mixture was allowed to react at 50-60° C. for 16 h. Next, the reaction was quenched by the addition of a saturated solution of ammonium chloride (10 mL), and the mixture was extracted with ethyl acetate (2×20 mL). The organic layer was washed with deionized water (2×20 mL), dried over anhydrous magnesium sulfate, filtered, and then concentrated under reduced pressure. The resulting residue was purified by flash column chromatography on silica gel (eluent: 5% ethyl acetate in hexane to 10% ethyl acetate in hexane) to provide the title compound (130 mg, 44.5%) as an oil.

Compound iv-F

Sodium hydride (60% dispersion in mineral oil, 20.4 mg, 0.51 mmol, 1.5 equiv) was added slowly to a stirred solution of compound ii-F (124 mg, 0.34 mmol, 1.0 equiv) in anhydrous dimethyl formamide (2 mL), at room temperature, and the contents were stirred under an atmosphere of argon for 10 min. A solution of (2R)-(–)-glycidyl tosylate 98% (116.4 mg, 0.51 mmol, 1.5 equiv) in anhydrous dimethyl formamide (1 mL) was added via syringe, and the mixture was allowed to react at room temperature for 16 h. Next, the reaction was quenched by the addition of a saturated solution of ammonium chloride (10 mL), and the mixture was extracted with ethyl acetate (2×20 mL). The organic layer was washed with deionized water (2×20 mL), dried over anhydrous magnesium sulfate, filtered and concentrated under reduced pressure. The resulting residue was purified by flash column chromatography on silica gel (eluent: 20% ethyl acetate in hexane to 40% ethyl acetate in hexane) to provide the title compound (70 mg, 49.4%) as a clear foam.

Compound 11d

To a solution of compound iv-F (70 mg, 0.17 mmol, 1.0 equiv) in acetonitrile (5 mL) was added $CeCl_3 \cdot 7H_2O$ (160.2 mg, 0.43 mmol, 2.5 equiv) and the mixture was refluxed for 16 h. The resulting white paste was filtered and washed with ethyl acetate, and the clear suspension was concentrated under reduced pressure. The resulting residue was purified by flash column chromatography on silica gel (eluent: 25% ethyl acetate in hexane to 70% ethyl acetate in hexane) to provide the title compound 11d (43 mg, 61.3%) as a transparent oil.

Example 4

FIGS. 1 and 2

Compound Activity

The PSA-luciferase (6.1 kb) reporter contains functional AREs to which AR binds in response to androgen to induce luciferase activity. LNCaP cells were transfected with the PSA(6.1 kb)-luciferase reporter for 24 h, and then treated with indicated concentration of 8d (also referred as EPI-iodide or iodinated EPI) with synthetic androgen, R1881 (1 nM) for 24 h. After 24 h of incubation with R1881, the cells were harvested, and relative luciferase activities were determined (FIG. 1A). To determine the $IC_{50}$, treatments were normalized to the predicted maximal activity induction (in the absence of test compounds, vehicle only) (FIG. 1B). From a representative experiment, it was determined that the 8d has an $IC_{50}$ of 1.17±0.22 µM for inhibition of AR transcriptional activity.

To assess specificity for the AR, parallel experiments were performed in LNCaP cells with endogenous AR and ectopic expression of other closely related human hormone receptors such as the progesterone receptor-beta (PRβ), glucocorticoid receptor (GR) and estrogen receptor-α (ER).

To measure effect on AR, after the LNCaP cells were transfected with the PSA(6.1 kb)-luciferase reporter for 24 h, they were then treated with DMSO, 5 µM MDV3100, 25 µM Z (also referred to as EPI-002 or EPI), or 1.9 µM 8d with or without 1 nM R1881 for 24 h (FIG. 2A). Compound 8d strongly inhibited androgen-induced PSA luciferase activity.

LNCaP cells were cotransfected with the expression plasmids for full-length human PRβ and the relative reporter (PRE-luciferase) for 24 h, and then treated with DMSO, 5 µM MDV3100, 25 µM Z, or 1.9 µM 8d with or without 10 nM progesterone for 24 h (FIG. 2B). Compound 8d had no effect on the transcriptional activity of closely related PRβ.

FIG. 2C shows GRE-luciferase activity where LNCaP cells were cotransfected with the expression plasmids for full-length human GR and the relative reporter (GRE-luciferase) for 24 h, and then treated with DMSO, 5 µM MDV3100, 25 µM Z, or 1.9 µM 8d with or without 10 nM dexamethasone for 48 h.

FIG. 2D shows ERE-luciferase activity where LNCaP cells were cotransfected with the expression plasmids for full-length human ERα and the relative reporter for 24 h, and then treated with DMSO, 5 µM MDV3100, 25 µM Z, or 1.9 µM 8d with or without 10 nM E2 (estradiol) for 24 h. For 8d, 1 µg/mL=1.9 µM in FIGS. 2A-2D.

Under conditions where compound 8d strongly inhibited AR-driven PSA-luciferase activity (FIG. 2A), PR-b, GR, or ERα activity were not inhibited (FIGS. 2B-2D). These data support that compound 8d has specificity for the AR.

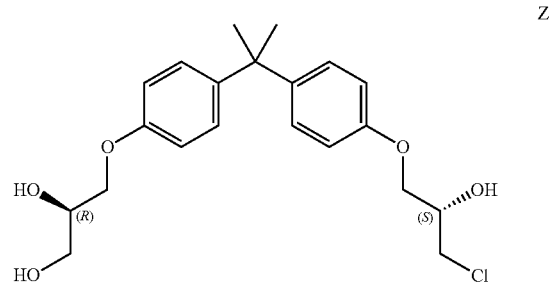

Z

Example 5

FIG. 14

Compound Activity

Competitive ligand-binding assays to detect the displacement of fluorescently labeled ligand from recombinant LBDs (ligand binding domains) of AR, PR, GR and estrogen receptor (ER) by R1881, MDV3100, Z (also referred to as EPI-002 or EPI) or 8d (also referred to as iodinated EPI) were performed. FIGS. 14A-14E display competitive ligand-binding curves to indicate whether R1881, Z, antiandrogens (enzalutamide, hydroxyflutamide, bicalutamide) or 8d can displace 1 nM fluorescently labeled cognant ligand from recombinant LBDs of steroid hormone receptors by using fluorescent polarization (mP). Serial dilution was performed for each test compound. Mixtures were incubated for 5 h before measurement of fluorescent polarization. The data shows 8d does not bind to LBDs of AR, PR, GR, and ER.

Example 6

FIG. 15

Compound Activity

Figure 15:
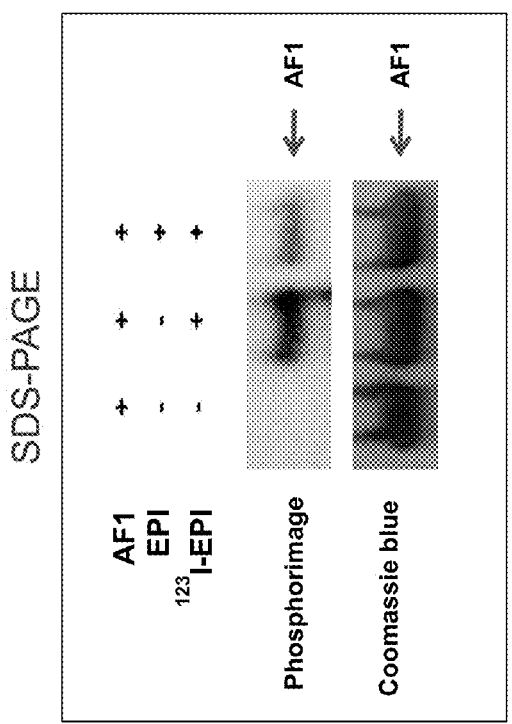
FIG. 15 shows binding experiment of 1d.

Covalent binding experiments of 1d (also referred to as $^{123}$I-EPI) to recombinant protein AR activation function-1 (AF1) was evaluated by SDS-PAGE (FIG. 15). After 6 h incubation at room temperature, 1d bound to the recombinant protein AR AF1. Less binding of 1d was observed when AR AF1 was pre-incubated with cold Z which is thought to bind to the same site as 1d. The SDS-PAGE gel was stained with Coomassie blue for loading control of the amount of AF1 protein. The data demonstrates that 1d binds to AF1 in the AR NTD.

Example 7

FIG. 16

Compound Activity

Figure 16:
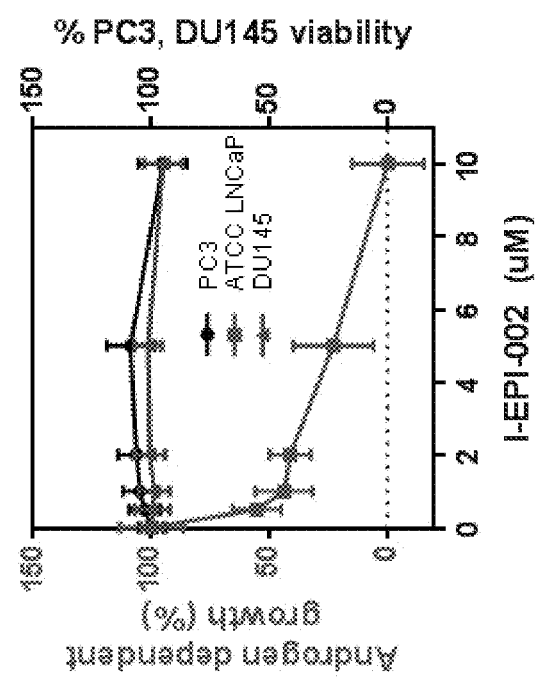
FIG. 16 shows cell viability and proliferation assay of 8d.

Effects of 8d (also referred to as I-EPI-002) on androgen-dependent proliferation of LNCaP cells treated with R1881 were compared with PC3 and DU145 cell viability by alamarBlue Cell Viability Assay (FIG. 16). 8d had no effect on the viability of PC3 and DU145 prostate cancer cells that do not express functional AR, at concentrations that reduced AR-dependent proliferation of LNCaP cells. FIG. 16 shows PC3 at day 3, LNCaP at day 4, and DU145 at day 3.

Example 8

Compound Activity

LNCaP cells were transiently transfected with PSA (6.1 kb)-luciferase for 24 h prior to pre-treatment with compounds of the invention (e.g., compounds 9d, 10d, 11d) ranging in concentration from 62.5 ng/ml to 1.5 ug/ml for 1 hour before the addition of vehicle, or synthetic androgen, R1881 (1 nM) to induce luciferase production. After 24 h of incubation with R1881, the cells were harvested, and relative luciferase activities were determined. To determine the IC$_{50}$, treatments were normalized to the predicted maximal activity induction (in the absence of test compounds, vehicle only) (FIG. 1B).

TABLE 1

| IC$_{50}$ values for 9d, 10d, and 11d (μM) | | | | | |
|---|---|---|---|---|---|
| Compound | Trial 1 | Trial 2 | Trial 3 | Trial 4 | Average |
| 9d | 2.07 | 2.74 | 2.96 | 3.36 | 2.78 +/− 0.47 |
| 10d | 2.53 | 2.30 | 2.81 | 2.84 | 2.62 +/− 0.22 |
| 11d | 5.95 | 3.60 | 7.33 | 5.40 | 5.57 +/− 1.34 |

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

The invention claimed is:

1. A compound having a structure of Formula I:

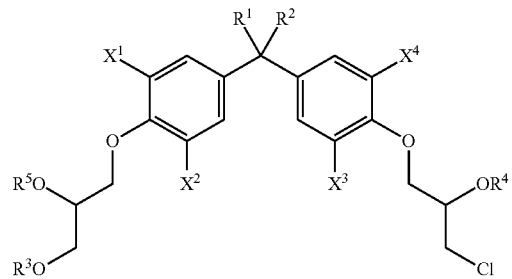

or a pharmaceutically acceptable salt, tautomer or stereoisomer thereof, wherein:

$R^1$ and $R^2$ are each independently H or $C_1$-$C_{10}$ alkyl, or $R^1$ and $R^2$, together with the carbon atom to which they are bound, are taken together to form a carbocyclic or heterocyclic ring;

$R^3$ is H or $C_1$-$C_{10}$ alkylcarboyl;

$R^4$ and $R^5$ are each independently H, $C_1$-$C_{10}$ alkyl or $C_1$-$C_{10}$ alkylcarbonyl; and $X^1$, $X^2$, $X^3$ and $X^4$ are each independently H, F, Cl, Br, I or $^{123}$I, wherein at least one of $X^1$, $X^2$, $X^3$ or $X^4$ is $^{123}$I.

2. The compound of claim 1, wherein the compound has one of the following structures (Ia), (Ib), (Ic), (Id), (Ie), (If), (Ig) or (Ih):

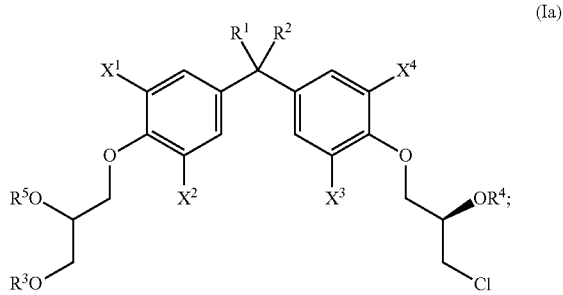

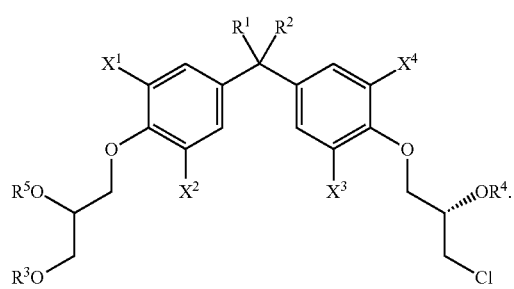
(Ib)

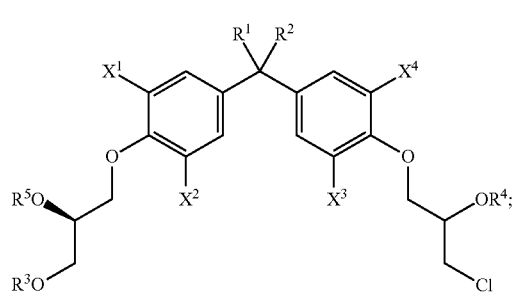
(Ic)

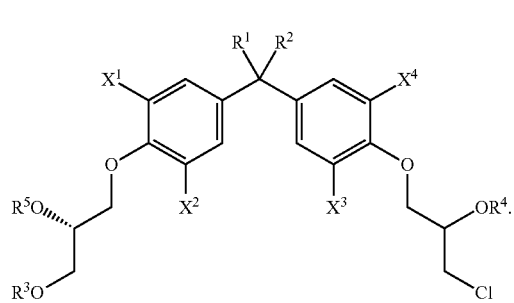
(Id)

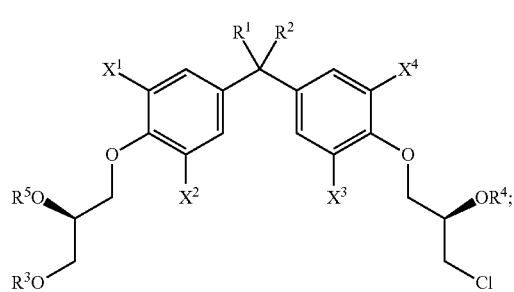
(Ie)

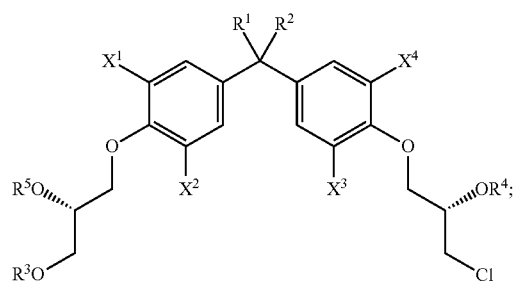
(If)

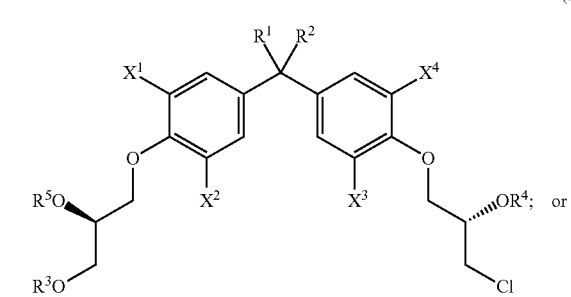
(Ig)

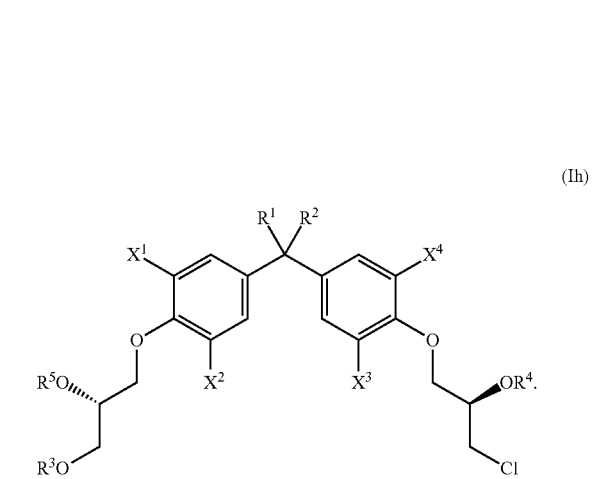
(Ih)

3. The compound of claim 1, wherein three of $X^1$, $X^2$, $X^3$ and $X^4$ are H, and the remaining $X^1$, $X^2$, $X^3$ or $X^4$ is $^{123}$I.

4. The compound of claim 1, wherein $X^1$ is F, Cl, Br or I or $^{123}$I.

5. The compound of claim 1, wherein $X^3$ is F, Cl, Br or I or $^{123}$I.

6. The compound of claim 1, wherein $R^1$ and $R^2$ are each $C_1$-$C_{10}$ alkyl.

7. The compound of claim 6, wherein $C_1$-$C_{10}$ alkyl is methyl.

8. The compound of claim 1, wherein at least one of $R^3$, $R^4$ or $R^5$ is H.

9. The compound of claim 1, wherein $R^3$, $R^4$ and $R^5$ are each H.

10. The compound of claim 1, wherein at least one of $R^4$ or $R^5$ is $C_1$-$C_{10}$ alkyl.

11. The compound of claim 1, wherein $R^4$ and $R^5$ are each $C_1$-$C_{10}$ alkyl.

12. The compound of claim 11, wherein $C_1$-$C_{10}$ alkyl is methyl, isopropyl or n-butyl.

13. The compound of claim 1, wherein at least one of $R^3$, $R^4$ or $R^5$ is $C_1$-$C_{10}$ alkylcarbonyl.

14. The compound of claim 1, wherein $R^3$, $R^4$ and $R^5$ are each $C_1$-$C_{10}$ alkylcarbonyl.

15. The compound of claim 14, wherein $C_1$-$C_{10}$ alkylcarbonyl is methyl carbonyl.

16. The compound of claim 1, wherein the compound has one of the following Structures:

63
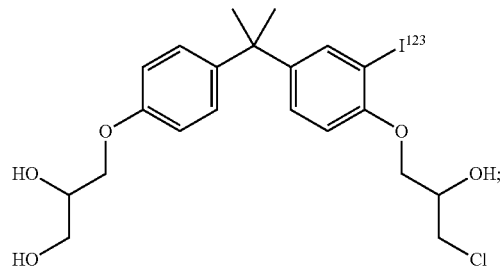
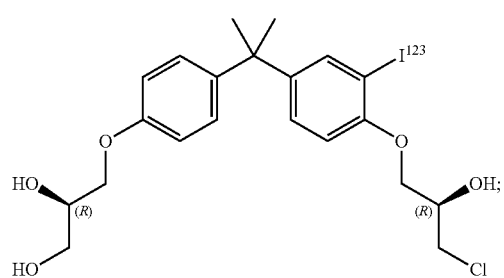
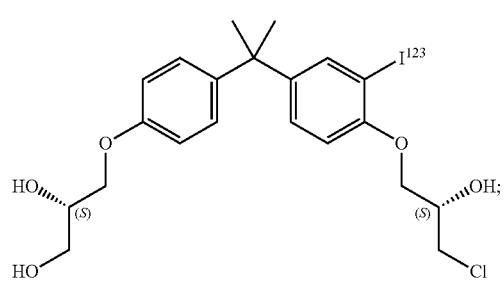
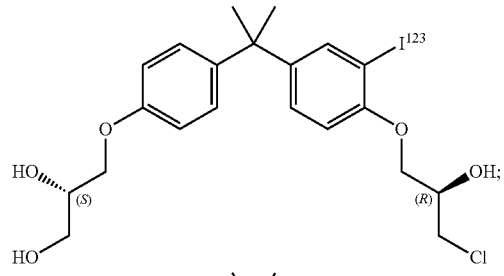
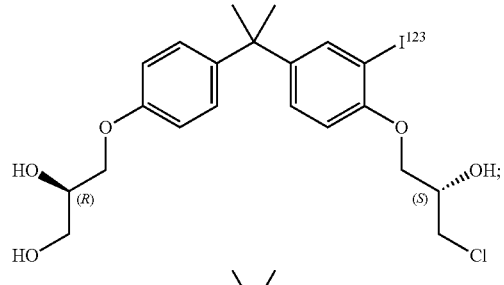
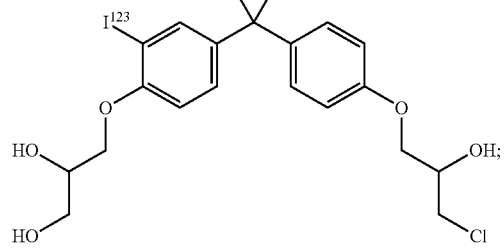
64
-continued
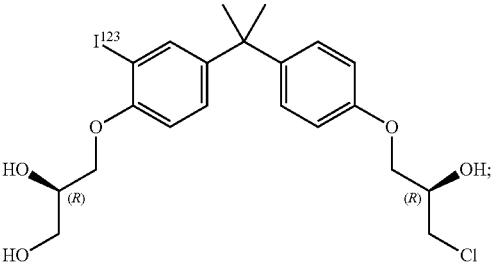
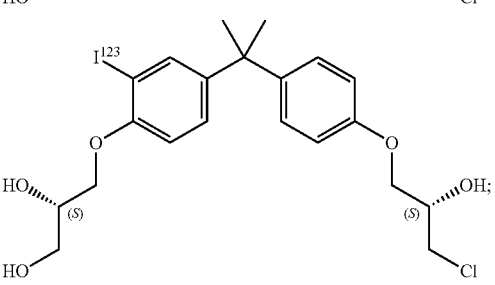
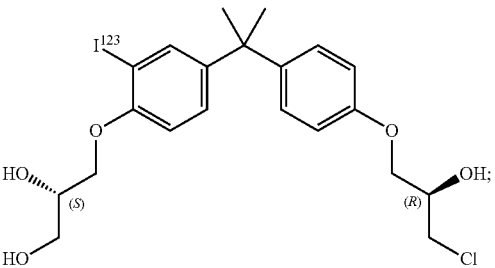
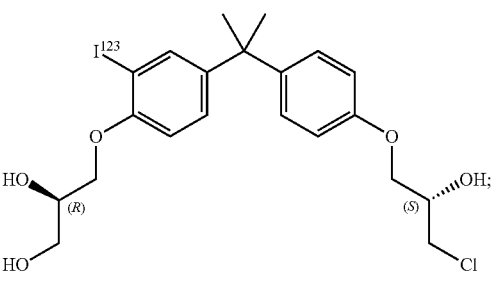
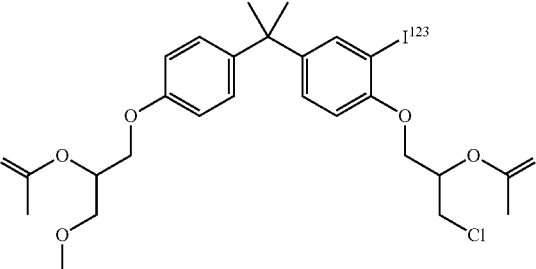
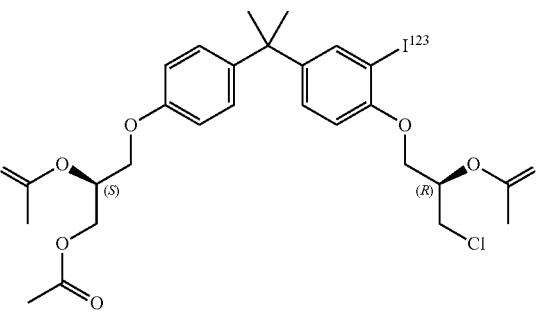

-continued

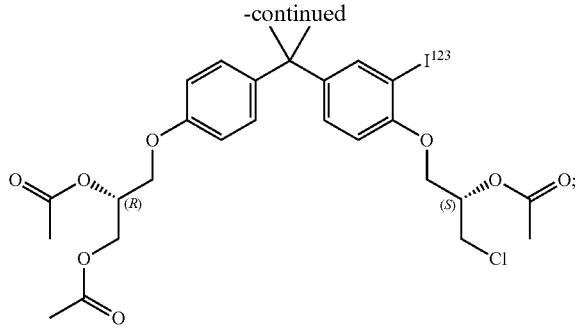
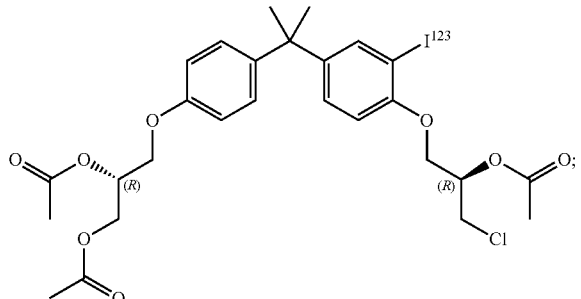
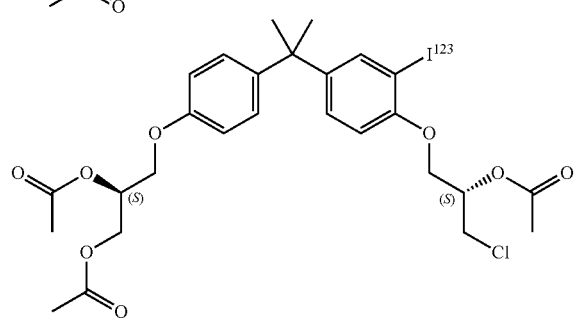

or a pharmaceutically acceptable salt or stereoisomer thereof.

17. A pharmaceutical composition comprising a compound of claim 1, and a pharmaceutically acceptable carrier.

18. A method of imaging cancer, the method comprising administering a compound of claim 1 to a subject and detecting the presence or absence of cancer by use of SPECT or PET.

19. The method of claim 18, wherein the method identifies the presence or absence of a tumor.

20. The method of claim 18, wherein the method identifies the location of a tumor.

21. The method of claim 18, wherein the cancer is prostate cancer.

22. A pharmaceutical composition comprising a compound of claim 1, an additional therapeutic agent and a pharmaceutically acceptable carrier, wherein the additional therapeutic agent is enzalutamide, galeterone, ODM-201, ARN-509, abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX 427, OGX 011, finasteride, dutasteride, turosteride, bexlosteride, izonsteride, FCE 28260, SKF105,111 or related compounds thereof.

23. A method of imaging cancer, the method comprising administering the pharmaceutical composition of claim 17 to a subject and detecting the presence or absence of cancer by use of SPECT or PET.

* * * * *